United States Patent
Aronin et al.

(10) Patent No.: US 8,987,222 B2
(45) Date of Patent: Mar. 24, 2015

(54) SINGLE NUCLEOTIDE POLYMORPHISM (SNP) TARGETING THERAPIES FOR THE TREATMENT OF HUNTINGTON'S DISEASE

(75) Inventors: Neil Aronin, Newtonville, MA (US); Edith Pfister, Boxborough, MA (US); Phillip D. Zamore, Northboro, MA (US)

(73) Assignee: University of Massachusetts, Boston, MA (US)

( * ) Notice: Subject to any disclaimer, the term of this patent is extended or adjusted under 35 U.S.C. 154(b) by 8 days.

(21) Appl. No.: 13/263,961

(22) PCT Filed: Apr. 8, 2010

(86) PCT No.: PCT/US2010/030438
§ 371 (c)(1),
(2), (4) Date: Jan. 30, 2012

(87) PCT Pub. No.: WO2010/118263
PCT Pub. Date: Oct. 14, 2010

(65) Prior Publication Data
US 2012/0136039 A1    May 31, 2012

Related U.S. Application Data

(60) Provisional application No. 61/167,861, filed on Apr. 8, 2009.

(51) Int. Cl.
| | |
|---|---|
| *A61K 48/00* | (2006.01) |
| *C07H 21/02* | (2006.01) |
| *C07H 21/04* | (2006.01) |
| *A61K 31/713* | (2006.01) |
| *C12N 15/113* | (2010.01) |

(52) U.S. Cl.
CPC ............ *C12N 15/113* (2013.01); *A61K 31/713* (2013.01); *C12N 2310/11* (2013.01); *C12N 2310/14* (2013.01); *C12N 2320/34* (2013.01)
USPC ........ 514/44; 536/23.1; 536/24.31; 536/24.3; 536/24.33; 536/24.5

(58) Field of Classification Search
None
See application file for complete search history.

(56) References Cited

U.S. PATENT DOCUMENTS

2005/0096284 A1    5/2005  McSwiggen

FOREIGN PATENT DOCUMENTS

| WO | 2008/005562 A2 | 1/2008 |
| WO | 2008/147887 A1 | 12/2008 |

OTHER PUBLICATIONS

Lombardi, Maria Stella et al., "A majority of Huntington's disease patients may be treatable by individualized allele-specific RNA interference," Experimental Neurology, vol. 217:312-319 (2009).
Ohnishi, Yusuke et al., "Enhancement of Allele Discrimination by Introduction of Nucleotide Mismatches into siRNA in Allele-Specific Gene Silencing by RNAi," PLoS One, vol. 3(5):e2248 (2008).
Pfister, Edith L. et al., "Five siRNAs Targeting Three SNPs May Provide Therapy for Three-Quarters of Huntington's Disease Patients," Current Biology, vol. 19:774-778 (2009).
Van Bilsen, P.H.J. et al., "Identification and Allele-Specific Silencing of the Mutant Huntingtin Allele in Huntington's Disease Patient-Derived Fibroblasts," Human Gene Therapy, vol. 19:710-718 (2008).
Warby, Simon C. et al., "CAG Expansion in the Huntington Disease Gene Is Associated with a Specific and Targetable Predisposing Haplogroup," The American Journal of Human Genetics, vol. 84:351-366 (2009).
International Preliminary Report on Patentability and Written Opinion for Application No. PCT/US2010/030438, dated Oct. 11, 2011.

*Primary Examiner* — Amy Bowman
(74) *Attorney, Agent, or Firm* — McCarter & English, LLP; Briana M. Erikson

(57) ABSTRACT

The present invention relates to the discovery of (SNPs) significantly associated with Huntington's disease (HD). The present invention utilizes RNA silencing technology (e.g. RNAi) against such SNPs optimally combined with select additional SNP targeting silencing agents, thereby resulting in an effective treatment of significantly-sized patient populations. Silencing agents having enhanced discriminatory properties are also featured.

21 Claims, 29 Drawing Sheets

```
3'-GAGCGCAACUUCAUGACAGGG-5' (SEQ ID NO: 1)
   5'-AGCGUUGAAGUACUGUCCCCA-3' (SEQ ID NO: 2)
      |||||||||||||||||||||
3'-acacaagaagaucgcaacuucaugacaggggguagagaauug-5' (SEQ ID NO: 3)
3'-GAGCGCAACUUAAUGACAGGG-5' (SEQ ID NO: 4)
   5'-AGCGUUGAAUUACUGUCCCCA-3' (SEQ ID NO: 5)
      |||||||||  |||||||||
3'-acacaagaagaucgcaacuucaugacaggggguagagaauug-5' (SEQ ID NO: 3)
```
Fig. 2A
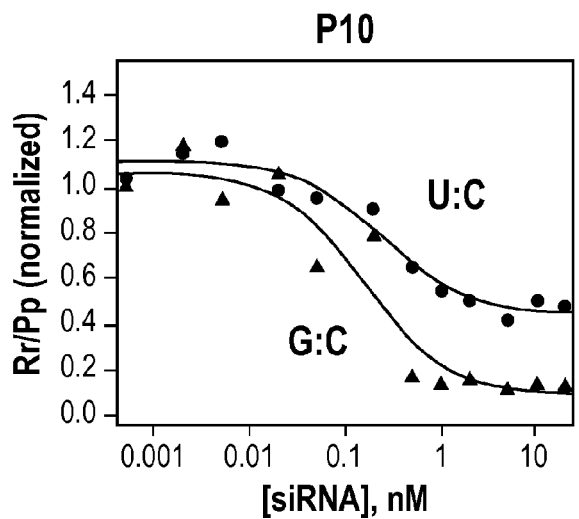
Fig. 2B
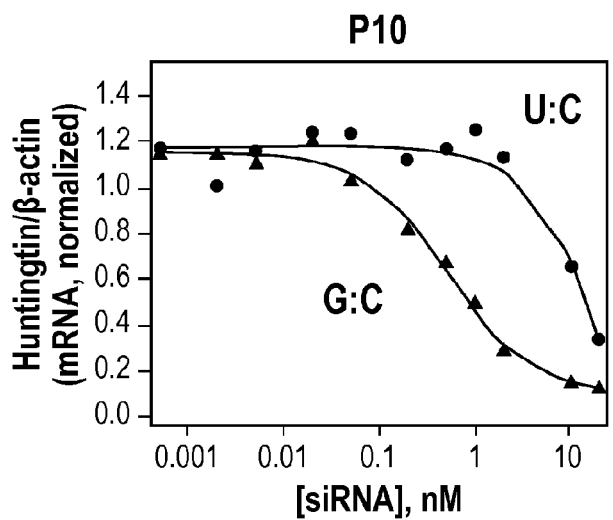
Fig. 2C

3'-CCCUGUUCCCGUGUCUGAAGG-5'  (SEQ ID NO: 6)
5'-pUACAAGGGCACAGACUUCCAA-3' (SEQ ID NO: 7)

3'-UCCGUCCCGUGUUCCCGUGUC-5'  (SEQ ID NO:12)
5'-pUCAGGGCACAAGGGCACAGAC-3' (SEQ ID NO:13)

3'-CCUCGUUCCCGUGUCUGAAGG-5'  (SEQ ID NO: 8)
5'-pCGCAAGGGCACAGACUUCCAA-3'  (SEQ ID NO: 9)

3'-CCUUAUUCCCGUGUCUGAAGG-5'  (SEQ ID NO:10)
5'-pCAUAAGGGCACAGACUUCCAA-3'  (SEQ ID NO:11)

3'-CCUUGGUCCCGUGUCUGAAGG-5'  (SEQ ID NO:14)
5'-pCACCAGGGCACAGACUUCCAA-3'  (SEQ ID NO:15)

3'-CCUUGUGCCCGUGUCUGAAGG-5'  (SEQ ID NO:16)
5'-pCACAC̲GGGCA̲CAGACUUCCAA-3'  (SEQ ID NO:17)

3'-CCUUGUUACCGUGUCUGAAGG-5'  (SEQ ID NO:20)
5'-pCACAAU̲GGCA̲CAGACUUCCAA-3'  (SEQ ID NO:21)

3'-CCUUGUUCACGUGUCUGAAGG-5'  (SEQ ID NO:22)
5'-pCACAAGU̲GCA̲CAGACUUCCAA-3'  (SEQ ID NO:23)

3'-GAGCGCAACUUAAUGACAGGG-5' (SEQ ID NO:32)
5'-AGCGUUGAA‌UUACUGUCCCCA-3' (SEQ ID NO:33)

3'-GAGCGCAACUUCAUGACAGGG-5' (SEQ ID NO:34)
5'-AGCGUUGAA‌GUACUGUCCCCA-3' (SEQ ID NO:35)

```
   1 TTGCTGTGTG AGGCAGAACC TGCGGGGGCA GGGGCGGGCT GGTTCCCTGG CCAGCCATTG
  61 GCAGAGTCCG CAGGCTAGGG CTGTCAATCA TGCTGGCCGG CGTGCCCCCG CCTCCGCCGG
 121 CGCGGCCCCG CCTCCGCCGG CGCACGTCTG GGACGCAAGG CGCCGTGGGG GCTGCCGGGA
 181 CGGGTCCAAG ATGGACGGCC GCTCAGGTTC TGCTTTTACC TGCGGCCCAG AGCCCCATTC
 241 ATTGCCCCGG TGCTGAGCGG CGCCGCGAGT CGGCCCGAGG CCTCCGGGGA CTGCCGTGCC
 301 GGGCGGGAGA CCGCCATGGC GACCCTGGAA AAGCTGATGA AGGCCTTCGA GTCCCTCAAG
 361 TCCTTCCAGC AGCAGCAGCA GCAGCAGCAG CAGCAGCAGC AGCAGCAGCA GCAGCAGCAG
 421 CAGCAGCAGC AACAGCCGCC ACCGCCGCCG CCGCCGCCGC CGCCTCCTCA GCTTCCTCAG
 481 CCGCCGCCGC AGGCACAGCC GCTGCTGCCT CAGCCGCAGC CGCCCCCGCC GCCGCCCCCG
 541 CCGCCACCCG GCCCGGCTGT GGCTGAGGAG CCGCTGCACC GACCAAAGAA AGAACTTTCA
 601 GCTACCAAGA AAGACCGTGT GAATCATTGT CTGACAATAT GTGAAAACAT AGTGGCACAG
 661 TCTGTCAGAA ATTCTCCAGA ATTTCAGAAA CTTCTGGGCA TCGCTATGGA ACTTTTTCTG
 721 CTGTGCAGTG ATGACGCAGA GTCAGATGTC AGGATGGTGG CTGACGAATG CCTCAACAAA
 781 GTTATCAAAG CTTTGATGGA TTCTAATCTT CCAAGGTTAC AGCTCGAGCT CTATAAGGAA
 841 ATTAAAAAGA ATGGTGCCCC TCGGAGTTTG CGTGCTGCCC TGTGGAGGTT TGCTGAGCTG
 901 GCTCACCTGG TTCGGCCTCA GAAATGCAGG CCTTACCTGG TGAACCTTCT GCCGTGCCTG
 961 ACTCGAACAA GCAAGAGACC CGAAGAATCA GTCCAGGAGA CCTTGGCTGC AGCTGTTCCC
1021 AAAATTATGG CTTCTTTTGG CAATTTTGCA AATGACAATG AAATAAGGT TTTGTTAAAG
1081 GCCTTCATAG CGAACCTGAA GTCAAGCTCC CCCACCATTC GGCGGACAGC GGCTGGATCA
1141 GCAGTGAGCA TCTGCCAGCA CTCAAGAAGG ACACAATATT CTATAGTTG GCTACTAAAT
1201 GTGCTCTTAG GCTTACTCGT TCCTGTCGAG GATGAACACT CCACTCTGCT GATTCTTGGC
```

*Fig. 12A*

```
1261 GTGCTGCTCA CCCTGAGGTA TTTGGTGCCC TTGCTGCAGC AGCAGGTCAA GGACACAAGC
1321 CTGAAAGGCA GCTTCGGAGT GACAAGGAAA GAAATGGAAG TCTCTCCTTC TGCAGAGCAG
1381 CTTGTCCAGG TTTATGAACT GACGTTACAT CATACACAGC ACCAAGACCA CAATGTTGTG
1441 ACCGGAGCCC TGGAGCTGTT GCAGCAGCTC TTCAGAACGC CTCCACCCGA GCTTCTGCAA
1501 ACCCTGACCG CAGTCGGGGG CATTGGGCAG CTCACCGCTG CTAAGGAGGA GTCTGGTGGC
1561 CGAAGCCGTA GTGGGAGTAT TGTGGAACTT ATAGCTGGAG GGGGTTCCTC ATGCAGCCCT
1621 GTCCTTTCAA GAAAACAAAA AGGCAAAGTG CTCTTAGGAG AAGAAGAAGC CTTGGAGGAT
1681 GACTCTGAAT CGAGATCGGA TGTCAGCAGC TCTGCCTTAA CAGCCTCAGT GAAGGATGAG
1741 ATCAGTGGAG AGCTGGCTGC TTCTTCAGGG GTTTCCACTC CAGGGTCAGC AGGTCATGAC
1801 ATCATCACAG AACAGCCACG GTCACAGCAC ACACTGCAGG CGGACTCAGT GGATCTGGCC
1861 AGCTGTGACT TGACAAGCTC TGCCACTGAT GGGGATGAGG AGGATATCTT GAGCCACAGC
1921 TCCAGCCAGG TCAGCGCCGT CCCATCTGAC CCTGCCATGG ACCTGAATGA TGGGACCCAG
1981 GCCTCGTCGC CCATCAGCGA CAGCTCCCAG ACCACCACCG AAGGGCCTGA TTCAGCTGTT
2041 ACCCCTTCAG ACAGTTCTGA AATTGTGTTA GACGGTACCG ACAACCAGTA TTTGGGCCTG
2101 CAGATTGGAC AGCCCCAGGA TGAAGATGAG GAAGCCACAG GTATTCTTCC TGATGAAGCC
2161 TCGGAGGCCT TCAGGAACTC TTCCATGGCC CTTCAACAGG CACATTTATT GAAAACATG
2221 AGTCACTGCA GGCAGCCTTC TGACAGCAGT GTTGATAAAT TTGTGTTGAG AGATGAAGCT
2281 ACTGAACCGG GTGATCAAGA AAACAAGCCT TGCCGCATCA AGGTGACAT TGGACAGTCC
2341 ACTGATGATG ACTCTGCACC TCTTGTCCAT GTGTCCGCC TTTTATCTGC TTCGTTTTTG
2401 CTAACAGGGG GAAAAAATGT GCTGGTTCCG GACAGGGATG TGAGGGTCAG CGTGAAGGCC
2461 CTGGCCCTCA GCTGTGTGGG AGCAGCTGTG GCCCTCCACC CGGAATCTTT CTTCAGCAAA
```

*Fig. 12B*

2521 CTCTATAAAG TTCCTCTTGA CACCACGGAA TACCCTGAGG AACAGTATGT CTCAGACATC
2581 TTGAACTACA TCGATCATGG AGACCCACAG GTTCGAGGAG CCACTGCCAT TCTCTGTGGG
2641 ACCCTCATCT GCTCCATCCT CAGCAGGTCC CGCTTCCACG TGGGAGATTG GATGGGCACC
2701 ATTAGAACCC TCACAGGAAA TACATTTTCT TTGGCGGATT GCATTCCTTT GCTGCGGAAA
2761 ACACTGAAGG ATGAGTCTTC TGTTACTTGC AAGTTAGCTT GTACAGCTGT GAGGAACTGT
2821 GTCATGAGTC TCTGCAGCAG CAGCTACAGT GAGTTAGGAC TGCAGCTGAT CATCGATGTG
2881 CTGACTCTGA GGAACAGTTC CTATTGGCTG GTGAGGACAG AGCTTCTGGA AACCCTTGCA
2941 GAGATTGACT TCAGGCTGGT GAGCTTTTTG GAGGCAAAAG CAGAAAACTT ACACAGAGGG
3001 GCTCATCATT ATACAGGGCT TTTAAAACTG CAAGAACGAG TGCTCAATAA TGTTGTCATC
3061 CATTTGCTTG GAGATGAAGA CCCCAGGGTG CGACATGTTG CCGCAGCATC ACTAATTAGG
3121 CTTGTCCCAA AGCTGTTTTA TAAATGTGAC CAAGGACAAG CTGATCCAGT AGTGGCCGTG
3181 GCAAGAGATC AAAGCAGTGT TTACCTGAAA CTTCTCATGC ATGAGACGCA GCCTCCATCT
3241 CATTTCTCCG TCAGCACAAT AACCAGAATA TATAGAGGCT ATAACCTACT ACCAAGCATA
3301 ACAGACGTCA CTATGGAAAA TAACCTTTCA AGAGTTATTG CAGCAGTTTC TCATGAACTA
3361 ATCACATCAA CCACCAGAGC ACTCACATTT GGATGCTGTG AAGCTTTGTG TCTTCTTTCC
3421 ACTGCCTTCC CAGTTTGCAT TTGGAGTTTA GGTTGGCACT GTGGAGTGCC TCCACTGAGT
3481 GCCTCAGATG AGTCTAGGAA GAGCTGTACC GTTGGGATGG CCACAATGAT TCTGACCCTG
3541 CTCTCGTCAG CTTGGTTCCC ATTGGATCTC TCAGCCCATC AAGATGCTTT GATTTTGGCC
3601 GGAAACTTGC TTGCAGCCAG TGCTCCCAAA TCTCTGAGAA GTTCATGGGC CTCTGAAGAA
3661 GAAGCCAACC CAGCAGCCAC CAAGCAAGAG GAGGTCTGGC CAGCCCTGGG GGACCGGGCC
3721 CTGGTGCCCA TGGTGGAGCA GCTCTTCTCT CACCTGCTGA AGGTGATTAA CATTTGTGCC

*Fig. 12C*

```
3781 CACGTCCTGG ATGACGTGGC TCCTGGACCC GCAATAAAGG CAGCCTTGCC TTCTCTAACA
3841 AACCCCCCTT CTCTAAGTCC CATCCGACGA AAGGGGAAGG AGAAAGAACC AGGAGAACAA
3901 GCATCTGTAC CGTTGAGTCC CAAGAAAGGC AGTGAGGCCA GTGCAGCTTC TAGACAATCT
3961 GATACCTCAG GTCCTGTTAC AACAAGTAAA TCCTCATCAC TGGGGAGTTT CTATCATCTT
4021 CCTTCATACC TCAAACTGCA TGATGTCCTG AAAGCTACAC ACGCTAACTA CAAGGTCACG
4081 CTGGATCTTC AGAACAGCAC GGAAAAGTTT GGAGGGTTTC TCCGCTCAGC CTTGGATGTT
4141 CTTTCTCAGA TACTAGAGCT GGCCACACTG CAGGACATTG GGAAGTGTGT TGAAGAGATC
4201 CTAGGATACC TGAAATCCTG CTTTAGTCGA GAACCAATGA TGGCAACTGT TTGTGTTCAA
4261 CAATTGTTGA AGACTCTCTT TGGCACAAAC TTGGCCTCCC AGTTTGATGG CTTATCTTCC
4321 AACCCCAGCA AGTCACAAGG CCGAGCACAG CGCCTTGGCT CCTCCAGTGT GAGGCCAGGC
4381 TTGTACCACT ACTGCTTCAT GGCCCCGTAC ACCCACTTCA CCCAGGCCCT CGCTGACGCC
4441 AGCCTGAGGA ACATGGTGCA GGCGGAGCAG GAGAACGACA CCTCGGGATG GTTTGATGTC
4501 CTCCAGAAAG TGTCTACCCA GTTGAAGACA AACCTCACGA GTGTCACAAA GAACCGTGCA
4561 GATAAGAATG CTATTCATAA TCACATTCGT TTGTTTGAAC CTCTTGTTAT AAAAGCTTTA
4621 AAACAGTACA CGACTACAAC ATGTGTGCAG TTACAGAAGC AGGTTTTAGA TTTGCTGGCG
4681 CAGCTGGTTC AGTTACGGGT TAATTACTGT CTTCTGGATT CAGATCAGGT GTTTATTGGC
4741 TTTGTATTGA AACAGTTTGA ATACATTGAA GTGGGCCAGT TCAGGGAATC AGAGGCAATC
4801 ATTCCAAACA TCTTTTTCTT CTTGGTATTA CTATCTTATG AACGCTATCA TTCAAAACAG
4861 ATCATTGGAA TTCCTAAAAT CATTCAGCTC TGTGATGGCA TCATGGCCAG TGGAAGGAAG
4921 GCTGTGACAC ATGCCATACC GGCTCTGCAG CCCATAGTCC ACGACCTCTT TGTATTAAGA
4981 GGAACAAATA AAGCTGATGC AGGAAAAGAG CTTGAAACCC AAAAAGAGGT GGTGGTGTCA
```

Fig. 12D

```
5041 ATGTTACTGA GACTCATCCA GTACCATCAG GTGTTGGAGA TGTICATTCT TGTCCTGCAG
5101 CAGTGCCACA AGGAGAATGA AGACAAGTGG AAGCGACTGT CTCGACAGAT AGCTGACATC
5161 ATCCTCCCAA TGTTAGCCAA ACAGCAGATG CACATTGACT CTCATGAAGC CCTTGGAGTG
5221 TTAAATACAT TATTTGAGAT TTTGGCCCCT TCCTCCCTCC GTCCGGTAGA CATGCTTTTA
5281 CGGAGTATGT TCGTCACTCC AAACACAATG GCGTCCGTGA GCACTGTTCA ACTGTGGATA
5341 TCGGAATTC TGGCCATTTT GAGGGTTCTG ATTTCCCAGT CAACTGAAGA TATTGTTCTT
5401 TCTCGTATTC AGGAGCTCTC CTTCTCTCCG TATTTAATCT CCTGTACAGT AATTAATAGG
5461 TTAAGAGATG GGACAGTAC TTCAACGCTA GAAGAACACA GTGAAGGGAA ACAAATAAAG
5521 AAITTGCCAG AAGAAACATT TTCAAGGTTT CTATTACAAC TGGITGGTAT TCTTTTAGAA
5581 GACATTGTTA CAAACAGCT GAAGGTGGAA ATGAGTGAGC AGCAACATAC TTTCTATTGC
5641 CAGGAACTAG GCACACTGCT AATGTGTCTG ATCCACATCT TCAAGTCTGG AATGTTCCGG
5701 AGAATCACAG CAGCTGCCAC TAGGCTGTTC CGCAGTGATG GCTGTGGCGG CAGTTTCTAC
5761 ACCCTGGACA GCTTGAACTT GCGGGCTCGT TCCATGATCA CCACCCACCC GGCCCTGGTG
5821 CTGCTCTGGT GTCAGATACT GCTGCTTGTC AACCACACCG ACTACCGCTG GTGGGCAGAA
5881 GTGCAGCAGA CCCCGAAAAG ACACAGTCTG TCCAGCACAA AGTIACTTAG TCCCCAGATG
5941 TCTGGAGAAG AGGAGGATTC TGACTTGGCA GCCAAACTTG GAAIGTGCAA TAGAGAAATA
6001 GTACGAAGAG GGGCTCTCAT TCTCTTCTGT GATTATGTCT GTCAGAACCT CCATGACTCC
6061 GAGCACTTAA CGTGGCTCAT TGTAAATCAC ATTCAAGATC TGATCAGCCT TTCCCACGAG
6121 CCTCCAGTAC AGGACTTCAT CAGTGCCGTT CATCGGAACT CTGCTGCCAG CGGCCTGTTC
6181 ATCCAGGCAA TTCAGTCTCG TTGTGAAAAC CTTTCAACTC AACCATGCT GAAGAAAACT
6241 CTTCAGTGCT TGGAGGGGAT CCATCTCAGC CAGTCGGGAG CTGTGCTCAC GCTGTATGTG
```

*Fig. 12E*

```
6301 GACAGGCTTC TGTGCACCCC TTTCCGTGTG CTGGCTCGCA TGGTCGACAT CCTTGCTTGT
6361 CGCCGGGTAG AAATGCTTCT GGCTGCAAAT TTACAGAGCA GCATGGCCCA GTTGCCAATG
6421 GAAGAACTCA ACAGAATCCA GGAATACCTT CAGAGCAGCG GGCTCGCTCA GAGACACCAA
6481 AGGCTCTATT CCCTGCTGGA CAGGTTTCGT CTCTCCACCA TGCAAGACTC ACTTAGTCCC
6541 TCTCCTCCAG TCTCTTCCCA CCCGCTGGAC GGGGATGGGC ACGTGTCACT GGAAACAGTG
6601 AGTCCGGACA AGACTGGTA CGTTCATCTT GTCAAATCCC AGTGTTGGAC CAGGTCAGAT
6661 TCTGCACTGC TGGAAGGTGC AGAGCTGGTG AATCGGATTC CTGCTGAAGA TATGAATGCC
6721 TTCATGATGA ACTCGGAGTT CAACCTAAGC CTGCTAGCTC CATGCTTAAG CCTAGGGATG
6781 AGTGAAATTT CTGGTGGCCA AAGAGTGCC CTTTTTGAAG CAGCCCGTGA GGTGACTCTG
6841 GCCCGTGTGA GCGGCACCGT GCAGCAGCTC CCTGCTGTCC ATCATGTCTT CCAGCCCGAG
6901 CTGCCTGCAG AGCCGGCGGC CTACTGGAGC AAGTTGAATG ATCTGTTTGG GGATGCTGCA
6961 CTGTATCAGT CCCTGCCCAC TCTGGCCCGG GCCCTGGCAC AGTACCTGGT GGTGGTCTCC
7021 AAACTGCCCA GTCATTTGCA CCTTCCTCCT GAGAAAGAGA AGGACATTGT GAAATTCGTG
7081 GTGGCAACCC TTGAGGCCCT GTCCTGGCAT TTGATCCATG AGCAGATCCC GCTGAGTCTG
7141 GATCTCCAGG CAGGGCTGGA CTGCTGCTGC CTGGCCCTGC AGCTGCCTGG CCTCTGGAGC
7201 GTGGTCTCCT CCACAGAGTT TGTGACCCAC GCCTGCTCCC TCATCTACTG TGTGCACTTC
7261 ATCCTGGAGG CCGTTGCAGT GCAGCCTGGA GAGCAGCTTC TTAGTCCAGA AAGAAGGACA
7321 AATACCCCAA AAGCCATCAG CGAGGAGGAG GAGGAAGTAG ATCCAAACAC ACAGAATCCT
7381 AAGTATATCA CTGCAGCCTG TGAGATGGTG GCAGAAATGG TGGAGTCTCT GCAGTCGGTG
7441 TTGGCCTTGG GTCATAAAAG GAATAGCGGC GTGCCGGCGT TCTCACGCC ATTGCTCAGG
7501 AACATCATCA TCAGCCTGGC CCGCCTGCCC CTTGTCAACA GCTACACACG TGTGCCCCCA
```

Fig. 12F

```
7561 CTGGTGTGGA AGCTTGGATG GTCACCCAAA CCGGGAGGGG ATTTTGGCAC AGCATTCCCT
7621 GAGATCCCCG TGGAGTTCCT CCAGGAAAAG GAAGTCTTTA AGGAGTTCAT CTACCGCATC
7681 AACACACTAG GCTGGACCAG TCGTACTCAG TTTGAAGAAA CTTGGGCCAC CCTCCTTGGT
7741 GTCCTGGTGA CGCAGCCCCT CGTGATGGAG CAGGAGGAGA GCCCACCAGA AGAAGACACA
7801 GAGAGGACCC AGATCAACGT CCTGGCCGTG CAGGCCATCA CCTCACTGGT GCTCAGTGCA
7861 ATGACTGTGC CTGTGGCCGG CAACCCAGCT GTAAGCTGCT TGGAGCAGCA GCCCCGGAAC
7921 AAGCCTCTGA AAGCTCTCGA CACCAGGTTT GGGAGGAAGC TGAGCATTAT CAGAGGGATT
7981 GTGGAGCAAG AGATTCAAGC AATGGTTTCA AAGAGAGAGA ATATTGCCAC CCATCATTTA
8041 TATCAGGCAT GGGATCCTGT CCCTTCTCTG TCTCCGGCTA CTACAGGTGC CCTCATCAGC
8101 CACGAGAAGC TGCTGCTACA GATCAACCCC GAGCGGGAGC TGGGGAGCAT GAGCTACAAA
8161 CTCGGCCAGG TGTCCATACA CTCCGTGTGG CTGGGGAACA GCATCACACC CCTGAGGGAG
8221 GAGGAATGGG ACGAGGAAGA GGAGGAGGAG GCCGACGCCC TGCACCTTC GTCACCACCC
8281 ACGTCTCCAG TCAACTCCAG GAAACACCGG GCTGGAGTTG ACATCCACTC CTGTTCGCAG
8341 TTTTTGCTTG AGTTGTACAG CCGCTGGATC CTGCCGTCCA GCTCAGCCAG GAGGACCCCG
8401 GCCATCCTGA TCAGTGAGGT GGTCAGATCC CTTCTAGTGG TCTCAGACTT GTTCACCGAG
8461 CGCAACCAGT TTGAGCTGAT GTATGTGACG CTGACAGAAC TGCGAAGGGT GCACCCTTCA
8521 GAAGACGAGA TCCTCGCTCA GTACCTGGTG CCTGCCACCT GCAAGGCAGC TGCCGTCCTT
8581 GGGATGGACA AGGCCGTGGC GGAGCCTGTC AGCCGCCTGC TGGAGAGCAC GCTCAGGAGC
8641 AGCCACCTGC CCAGCAGGGT TGGAGCCCTG CACGGCGTCC TCTATGTGCT GGAGTGCGAC
8701 CTGCTGGACG ACACTGCCAA GCAGCTCATC CCGGTCATCA GCGACTATCT CCTCTCCAAC
8761 CTGAAAGGGA TCGCCCACTG CGTGAACATT CACAGCCAGC AGCACGTACT GGTCATGTGT
```

*Fig. 12G*

```
8821  GCCACTGCGT TTTACCTCAT TGAGAACTAT CCTCTGGACG TAGGGCCGGA ATTTTCAGCA
8881  TCAATAATAC AGATGTGTGG GGTGATGCTG TCTGGAAGTG AGGAGTCCAC CCCCTCCATC
8941  ATTTACCACT GTGCCCTCAG AGGCCTGGAG CGCCTCCTGC TCTCTGAGCA GCTCTCCCGC
9001  CTGGATGCAG AATCGCTGGT CAAGCTGAGT GTGGACAGAG TGAACGTGCA CAGCCCGCAC
9061  CGGGCCATGG CGGCTCTGGG CCTGATGCTC ACCTGCATGT ACACAGGAAA GGAGAAAGTC
9121  AGTCCGGGTA GAACTTCAGA CCCTAATCCT GCAGCCCCCG ACAGCGAGTC AGTGATTGTT
9181  GCTATGGAGC GGGTATCTGT TCTTTTTGAT AGGATCAGGA AAGGCTTTCC TTGTGAAGCC
9241  AGAGTGGTGG CCAGGATCCT GCCCCAGTTT CTAGACGACT TCTTCCCACC CCAGGACATC
9301  ATGAACAAAG TCATCGGAGA GTTTCTGTCC AACCAGCAGC ATACCCCCA GTTCATGGCC
9361  ACCGTGGTGT ATAAGGTGTT TCAGACTCTG CACAGCACCG GCAGTCGTC CATGGTCCGG
9421  GACTGGGTCA TGCTGTCCCT CTCCAACTTC ACGCAGAGGG CCCCGGTCGC CATGGCCACG
9481  TGGAGCCTCT CCTGCTTCTT TGTCAGCGCG TCCACCAGCC CGTGGGTCGC GGCGATCCTC
9541  CCACATGTCA TCAGCAGGAT GGGCAAGCTG GAGCAGGTGG ACGTGAACCT TTTCTGCCTG
9601  GTCGCCACAG ACTTCTACAG ACACCAGATA GAGGAGGAGC TCGACCGCAG GGCCTTCCAG
9661  TCTGTGCTTG AGGTGGTTGC AGCCCCAGGA AGCCCATATC ACCGGCTGCT GACTTGTTTA
9721  CGAAATGTCC ACAAGGTCAC CACCTGCTGA GCGCCATGGT GGGAGAGACT GTGAGGCGGC
9781  AGCTGGGGCC GGAGCCTTTG GAAGTCTGTG CCCTTGTGCC CTGCCTCCAC CGAGCCAGCT
9841  TGGTCCCTAT GGGCTTCCGC ACATGCCGCG GCGGCCAGG CAACGTGCGT GTCTCTGCCA
9901  TGTGGCAGAA GTGCTCTTTG TGGCAGTGGC CAGGCAGGGA GTGTCTGCAG TCCTGGTGGG
9961  GCTGAGCCTG AGGCCTTCCA GAAAGCAGGA GCAGCTGTGC TGCACCCCAT GTGGGTGACC
10021 AGGTCCTTTC TCCTGATAGT CACCTGCTGG TTGTTGCCAG GTTGCAGCTG CTCTTGCATC
```

*Fig. 12H*

```
10081 TGGGCCAGAA GTCCTCCCTC CTGCAGGCTG GCTGTTGGCC CCTCTGCTGT CCTGCAGTAG
10141 AAGGTGCCGT GAGCAGGCTT TGGGAACACT GGCCTGGGTC TCCCTGGTGG GGTGTGCATG
10201 CCACGCCCCG TGTCTGGATG CACAGATGCC ATGCCTGTG CTGGGCCAGT GGCTGGGGGT
10261 GCTAGACACC CGGCACCATT CTCCCTTCTC TCTTTTCTTC TCAGGATTTA AAATTTAATT
10321 ATATCAGTAA AGAGATTAAT TTTAACGAAC TCTTTCTATG CCCGTGTAAA GTATGTGAAT
10381 CGCAAGGCCT GTGCTGCATG CGACAGCGTC CGGGGTGGTG GACAGGGCCC CCGGCCACGC
10441 TCCCTCTCCT GTAGCCACTG GCATAGCCCT CCTGAGCACC CGCTGACATT TCCGTTGTAC
10501 ATGTTCCTGT TTATGCATTC ACAAGGTGAC TGGGATGTAG AGAGGCGTTA GTGGGCAGGT
10561 GGCCACAGCA GGACTGAGGA CAGGCCCCCA TTATCCTAGG GGTGCGCTCA ACTGCAGCCC
10621 CTCCTCCTCG GGCACAGACG ACTGTCGTTC TCCACCCACC AGTCAGGGAC AGCAGCCTCC
10681 CTGTCACTCA GCTGAGAAGG CCAGCCCTCC CTGGCTGTGA GCAGCCTCCA CTGTGTCCAG
10741 AGACATGGGC CTCCCACTCC TGTTCCTTGC TAGCCCTGGG GTGGCGTCTG CCTAGGAGCT
10801 GGCTGGCAGG TGTTGGGACC TGCTGCTCCA TGGATGCATG CCCTAAGAGT GTCACTGAGC
10861 TGTGTTTTGT CTGAGCCTCT CTCGGTCAAC AGCAAAGCTT GGTGTCTTGG CACTGTTAGT
10921 GACAGAGCCC AGCATCCCTT CTGCCCCCGT TCCAGCTGAC ATCTTGCACG GTGACCCCTT
10981 TTAGTCAGGA GAGTGCAGAT CTGTGCTCAT CGGAGACTGC CCCACGGCCC TGTCAGAGCC
11041 GCCACTCCTA TCCCCAGGAC AGGTCCCTGG ACCAGCCTCC TGTTTGCAGG CCCAGAGGAG
11101 CCAAGTCATT AAAATGGAAG TGGATTCTGG ATGGCCGGGC TGCTGCTGAT GTAGGAGCTG
11161 GATTTGGGAG CTCTGCTTGC CGACTGGCTG TGAGACGAGG CAGGGCTCT GCTTCCTCAG
11221 CCCTAGAGGC GAGCCAGGCA AGGTTGGCGA CTGTCATGTG GCTTGGTTTG GTCATGCCCG
11281 TCGATGTTTT GGGTATTGAA TGTGGTAAGT GGAGGAAATG TTGGAACTCT GTGCAGGTGC
```

*Fig. 12I*

```
11341 TGCCTTGAGA CCCCCAAGCT TCCACCTGTC CCTCTCCTAT GTGGCAGCTG GGGAGCAGCT
11401 GAGATGTGGA CTTGTATGCT GCCCACATAC GTGAGGGGGA GCTGAAAGGG AGCCCCTGCT
11461 CAAAGGGAGC CCCTCCTCTG AGCAGCCTCT GCCAGGCCTG TATGAGGCTT TTCCCACCAG
11521 CTCCCAACAG AGGCCTCCCC CAGCCAGGAC CACCTCGTCC TCGTGGCGGG GCAGCAGGAG
11581 CGGTAGAAAG GGGTCCGATG TTTGAGGAGG CCCTTAAGGG AAGCTACTGA ATTATAACAC
11641 GTAAGAAAAT CACCATTCTT CCGTATTGGT TGGGGGCTCC TGTTTCTCAT CCTAGCTTTT
11701 TCCTGGAAAA GCCCGCTAGA AGGTTTGGGA ACGAGGGGAA AGTTCTCAGA ACTGTTGCTG
11761 CTCCCCACCC GCCTCCCGCC TCCCCCGCAG GTTATGTCAG CAGCTCTGAG ACAGCAGTAT
11821 CACAGGCCAG ATGTTGTTCC TGGCTAGATG TTTACATTTG TAAGAAATAA CACTGTGAAT
11881 GTAAAACAGA GCCATTCCCT TGGAATGCAT ATCGCTGGGC TCAACATAGA GTTTGTCTTC
11941 CTCTTGTTTA CGACGTGATC TAAACCAGTC CTTAGCAAGG GGCTCAGAAC ACCCCGCTCT
12001 GGCAGTAGGT GTCCCCCACC CCCAAAGACC TGCCTGTGTG CTCCGGAGAT GAATATGAGC
12061 TCATTAGTAA AAATGACTTC ACCCACGCAT ATACATAAAG TATCCATGCA TGTGCATATA
12121 GACACATCTA TAATTTTACA CACACACCTC TCAAGACGGA GATGCATGGC CTCTAAGAGT
12181 GCCCGTGTCG GTTCTTCCTG GAAGTTGACT TTCCTTAGAC CCGCCAGGTC AAGTTAGCCG
12241 CGTGACGGAC ATCCAGGCGT GGGACGTGGT CAGGGCAGGG CTCATTCATT GCCCACTAGG
12301 ATCCCACTGG CGAAGATGGT CTCCATATCA GCTCTCTGCA GAAGGGAGGA AGACTTTATC
12361 ATGTTCCTAA AAATCTGTGG CAAGCACCCA TCGTATTATC CAAATTTTGT TGCAAATGTG
12421 ATTAATTTGG TTGTCAAGTT TTGGGGGTGG GCTGTGGGGA GATTGCTTTT GTTTTCCTGC
12481 TGGTAATATC GGGAAAGATT TTAATGAAAC CAGGGTAGAA TTGTTTGGCA ATGCACTGAA
12541 GCGTGTTTCT TTCCCAAAAT GTGCCTCCCT TCCGCTGCGG GCCCAGCTGA GTCTATGTAG
```

Fig. 12J

```
12601 GTGATGTTTC CAGCTGCCAA GTGCTCTTTG TTACTGTCCA CCCTCATTTC TGCCAGCGCA
12661 TGTGTCCTTT CAAGGGGAAA ATGTGAAGCT GAACCCCCTC CAGACACCCA GAATGTAGCA
12721 TCTGAGAAGG CCCTGTGCCC TAAAGGACAC CCCTCGCCCC CATCTTCATG GAGGGGGTCA
12781 TTTCAGAGCC CTCGGAGCCA ATGAACAGCT CCTCCTCTTG GAGCTGAGAT GAGCCCCACG
12841 TGGAGCTCGG GACGGATAGT AGACAGCAAT AACTCGGTGT GTGGCCGCCT GGCAGGTGGA
12901 ACTTCCTCCC GTTGCGGGGT GGAGTGAGGT TAGTTCTGTG TGTCTGGTGG GTGGAGTCAG
12961 GCTTCTCTTG CTACCTGTGA GCATCCTTCC CAGCAGACAT CCTCATCGGG CTTTGTCCCT
13021 CCCCCGCTTC CTCCCTCTGC GGGGAGGACC CGGGACCACA GCTGCTGGCC AGGGTAGACT
13081 TGGAGCTGTC CTCCAGAGGG GTCACGTGTA GGAGTGAGAA GAAGGAAGAT CTTGAGAGCT
13141 GCTGAGGGAC CTTGGAGAGC TCAGGATGGC TCAGACGAGG ACACTCGCTT GCCGGGCCTG
13201 GCCCTCCTGG GAAGGAGGGA GCTGCTCAGA ATGCCGCATG ACAACTGAAG GCAACCTGGA
13261 AGGTTCAGGG CCCGCTCTTC CCCCATGTGC CTGTCACGCT CTGGTGCAGT CAAAGGAACG
13321 CCTTCCCCTC AGTTGTTTCT AAGAGCAGAG TCTCCCGCTG CAATCTGGGT GGTAACTGCC
13381 AGCCTTGGAG GATCGTGGCC AACGTGGACC TGCCTACGGA GGGTGGGCTC TGACCCAAGT
13441 GGGGCCTCCT TGCCCAGGTC TCACTGCTTT GCACCGTGGT CAGAGGGACT GTCAGCTGAG
13501 CTTGAGCTCC CCTGGAGCCA GCAGGGCTGT GATGGGCGAG TCCCGGAGCC CCACCCAGAC
13561 CTGAATGCTT CTGAGAGCAA AGGGAAGGAC TGACGAGAGA TGTATATTTA ATTTTTTAAC
13621 TGCTGCAAAC ATTGTACATC CAAATTAAAG GGAAAAAATG GAAACCATCA AT
```

*Fig. 12K*

```
   1 matleklmka feslksfqqq qqqqqqqqqq qqqqqqqqqq pppppppppp pqlpqpppqa
  61 qpllpqpqpp ppppppppgp avaeeplhrp kkelsatkkd rvnhcltice nivaqsvrns
 121 pefqkllgia melfllcsdd aesdvrmvad eclnkvikal mdsnlprlql elykeikkng
 181 aprslraalw rfaelahlvr pqkcrpylvn llpcltrtsk rpeesvqetl aaavpkimas
 241 fgnfandnei kvllkafian lksssptirr taagsavsic qhsrrtqyfy swllnvllgl
 301 lvpvedehst llilgvlltl rylvpllqqq vkdtslkgsf gvtrkemevs psaeqlvqvy
 361 eltlhhtqhq dhnvvtgale llqqlfrtpp pellqtltav ggigqltaak eesggrsrsg
 421 siveliaggg sscspvlsrk qkgkvllqee ealeddsesr sdvsssalta svkdeisgel
 481 aassgvstpg saghdiiteq prsqhtlqad svdlascdlt ssatdgdeed ilshsssqvs
 541 avpsdpamdl ndgtqasspi sdssqttteg pdsavtpsds seivldgtdn qylglqigqp
 601 qdedeeatgi lpdeaseafr nssmalqqah llknmshcrq psdssvdkfv lrdeatepgd
 661 qenkpcrikg digqstddds aplvhcvrll sasflltggk nvlvpdrdvr vsvkalalsc
 721 vqaavalhpe sffsklykvp ldtteypeeq yvsdilnyid hgdpqvrgat ailcgtlics
 781 ilsrsrfhvg dwmgtirtlt qntfsladci pllrktlkde ssvtcklact avrncvmslc
 841 sssyselglq liidvltlrn ssywlvrtel letlaeidfr lvsfleakae nlhrgahhyt
 901 gllklqervl nnvvihllgd edprvrhvaa aslirlvpkl fykcdqgqad pvvavardqs
 961 svylkllmhe tqppshfsvs titriyrgyn llpsitdvtm ennlsrviaa vshelitstt
1021 raltfgccea lcllstafpv ciwslqwhcg vpplsasdes rksctvgmat miltllssaw
1081 fpldlsahqd alilagnlla asapkslrss waseeeanpa atkqeevwpa lgdralvpmv
1141 eqlfshllkv inicahvldd vapgpaikaa lpsltnppsl spirrkqkek epgeqasvpl
1201 spkkgseasa asrqsdtsgp vttsksssig sfyhlpsylk lhdvlkatha nykvtldlqn
1261 stekfggflr saldvlsqil elatlqdigk cveeilgylk scfsrepmma tvcvqqllkt
1321 lfgtnlasqf dglssnpsks qgraqrlgss svrpglyhyc fmapythftq aladaslrnm
1381 vqaeqendts gwfdvlqkvs tqlktnltsv tknradknai hnhirlfepl vikalkqytt
1441 ttcvqlqkqv ldllaqlvql rvnyclldsd qvfigfvlkq feyievgqfr eseaiipnif
1501 ffvllsyer yhskqiigip kiiqlcdgim asgrkavtha ipalqpivhd lfvlrgtnka
1561 dagkeletqk evvvsmllrl iqyhqvlenf ilvlqqchke nedkwkrlsr qiadiilpml
1621 akqqmhidsh ealgvlntlf eilapsslrp vdmllrsmfv tpntmasvst vqlwisqila
1681 ilrvlisqst edivlsriqe lsfspylisc tvinrlrdgd ststleehse gkqiknlpee
1741 tfsrfllqlv gilledivtk qlkvemseqq htfycqelgt llmclihifk sgmfrritaa
```

Fig. 13A

```
1801 atrlfrsdgc ggsfytldsl nlrarsmitt hpalvllwcq illlvnhtdy rwwaevqqtp
1861 krhslsstkl lspqmsgeee dsdlaaklgm cnreivrrga lilfcdyvcq nlhdsehltw
1921 livnhiqdli slsheppvqd fisavhrnsa asglfiqaiq srcenlstpt mlkktlqcle
1981 gihlsqsgav ltlyvdrllc tpfrvlarmv dilacrrvem llaanlqssm aqlpmeelnr
2041 iqeylqssgl aqrhqrlysl ldrfrlstmq dslspsppvs shpldgdghv sletvspdkd
2101 wyvhlvksqc wtrsdsalle gaelvnripa edmnafmmns efnlsllapc lslgmseisg
2161 gqksalfeaa revtlarvsg tvqqlpavhh vfqpelpaep aaywsklndl fgdaalyqsl
2221 ptlaralaqy lvvvsklpsh lhlppekekd ivkfvvatle alswhliheq iplsldlqag
2281 ldccclalql pglwsvvsst efvthacsli ycvhfileav avqpgeqlls perrtntpka
2341 iseeeeevdp ntqnpkyita acemvaemve slqsvlalgh krnsgvpafl tpllrniiis
2401 larlplvnsy trvpplvwkl gwspkpggdf gtafpeipve flqekevfke fiyrintlgw
2461 tsrtqfeetw atllgvlvtq plvmeqeesp peedtertqi nvlavqaits lvlsamtvpv
2521 agnpavscle qqprnkplka ldtrfgrkls iirgiveqei qamvskreni athhlyqawd
2581 pvpslspatt galishekll lqinperelg smsyklgqvs ihsvwlgnsi tplreeewde
2641 eeeeeadapa psspptspvn srkhragvdi hscsqfllel ysrwilpsss arrtpailis
2701 evvrsllvvs dlfternqfe lmyvtltelr rvhpsedeil aqylvpatck aaavlgmdka
2761 vaepvsrlle stlrsshlps rvgalhgvly vlecdllddt akqlipvisd yllsnlkgia
2821 hcvnihsqqh vlvmcatafy lienypldvg pefsasiiqm cgvmlsgsee stpsilyhca
2881 lrglerllls eqlsrldaes lvklsvdrvn vhsphramaa lglmltcmyt gkekvspgrt
2941 sdpnpaapds esvivamerv svlfdrirkg fpcearvvar ilpqflddff ppqdimnkvi
3001 geflsnqqpy pqfmatvvyk vfqtlhstgq ssmvrdwvml slsnftqrap vamatwslsc
3061 ffvsastspw vaailphvis rmgkleqvdv nlfclvatdf yrhqieeeld rrafqsvlev
3121 vaapgspyhr lltclrnvhk vttc
```

SINGLE NUCLEOTIDE POLYMORPHISM (SNP) TARGETING THERAPIES FOR THE TREATMENT OF HUNTINGTON'S DISEASE

RELATED APPLICATIONS

This application is a 35 U.S.C. 371 national stage filing of International Application No. PCT/US2010/030438 filed Apr. 8, 2010, which claims priority to U.S. Provisional Patent Application No. 61/167,861, filed Apr. 8, 2009. This application is related to U.S. patent application Ser. No. 10/571,705, filed Dec. 9, 2008, entitled "RNA interference for the treatment of gain-of-function disorders" and to U.S. patent application Ser. No. 12/348,794, filed Jan. 5, 2009, entitled "RNA silencing compositions and methods for the treatment of Huntington's disease".

The entire contents of the above identified applications are hereby incorporated by reference.

STATEMENT AS TO FEDERALLY FUNDED RESEARCH

This invention was made with government support under Grant No. NS038194, awarded by the National Institutes of Health. The government has certain rights in the invention.

BACKGROUND OF THE INVENTION

Among dominant neurodegenerative disorders, Huntington's disease (HD) is perhaps the best candidate for treatment with small interfering RNAs (siRNAs) (Xia et al., 2002, 2004, 2006; Machida et al., 2006; Wang et al., 2005; Harper et al., 2005; DiFiglia et al., 2007; Ralph et al., 2005; Raoul et al., 2005). Invariably fatal, HD is caused by expansion of a CAG repeat in the Huntingtin gene, creating an extended polyglutamine tract that makes the Huntingtin protein toxic (The Huntington's disease collaborative research group, 1993). Silencing mutant Huntingtin messenger RNA (mRNA) should provide therapeutic benefit, but normal Huntingtin likely contributes to neuronal function (Auerbach et al., 2001, Cattaneo, et al., 2005; Dragatsis et al., 2000). No siRNA strategy can yet distinguish among the normal and disease Huntingtin alleles and other mRNAs containing CAG repeats (Caplen et al., 2002). siRNAs targeting the disease isoform of a heterozygous single-nucleotide polymorphism (SNP) in Huntingtin provide an alternative (Schwarz et al., 2006; Ding et al., 2003; Dahlgren et al., 2008; Du et al., 2005; Miller et al., 2004).

SUMMARY OF THE INVENTION

The present invention is based, at least in part, on the discovery of single nucleotide polymorphism (SNP) sites in the Huntingtin (htt) gene which are preferred target sites for RNA silencing. The htt SNP sites of the invention are relatively prevalent within a sample population. In a particular embodiment, invention the htt SNPs targeted in the methods of the invention are linked with the expanded CAG repeat region of the HD-associated allele to form a HD-associated haplotype. Such HD-associated htt SNPs are attractive targets for therapeutic RNA silencing agents and circumvent complications associated with directly targeting the expanded CAG repeat region of htt.

In order to provide therapy for HD subjects in a HD population, subjects in the population can be treated with one or more RNA silencing agents based on the sequence of their htt mRNA at particular SNP loci. The instant inventors identified particular combinations of SNPs that provide coverage for a large percentage of subjects in a HD population. In particular embodiments, targeting a HD-associated SNP in combination with one or more SNPs having a high frequency of heterozygosity in the HD population allows for treatment of a large percentage of subjects in a HD population. In one embodiment set forth herein, targeting of a HD-associated SNP in combination with two other SNPs having a frequency of heterozygosity of 30% or more allows treatment of over 70% of the subjects in a HD population.

In one aspect, the invention is directed to a method of treating a subject having or at risk for Huntington's disease, comprising: administering to said subject an effective amount of a RNA silencing agent targeting a HD-associated htt single nucleotide polymorphism (SNP) within a target mRNA encoding a mutant huntingtin (htt) protein, such that RNA silencing of said mRNA occurs. Treating said disease in said subjects of an HD population is preferably achieved by targeting said HD-associated htt SNP in combination with one or more (e.g., two) other SNPs having an allelic frequency (i.e., a frequency of heterozygosity) of at least 10% (e.g., at least 15%, 20%, 25%, 30%, 35%, 40% or more) in a sample population.

In another aspect, the invention is directed to an RNA silencing agent comprising an antisense strand comprising about 16-25 nucleotides homologous to a region of an mRNA encoding a mutant huntingtin (htt) protein, said region comprising a heterozygous single nucleotide polymorphism (SNP) allele being associated with HD. In another aspect, the invention features siRNA agents homologous to a region of htt mRNA, said region comprising a heterogeneous SNP allele having a frequency of heterozygosity of at least 10% (e.g., at least 15%, 20%, 25%, 30%, 35%, 40% or more) in a sample population, wherein the RNA silencing agent is capable of directing RNA silencing of said mRNA. Such silencing agents are preferably used in combination such that at least 50%, preferably 55%, 60%, 65%, 70%, 75%, or more of a HD patient population is effected.

In one embodiment, the SNP allele is present at SNP target site RS362307. In a particular embodiment, the SNP allele is a U nucleotide.

In another embodiment, the SNP allele is present at SNP target site RS363125. In a particular embodiment, the SNP allele is an A nucleotide. In another particular embodiment, the SNP allele is a C nucleotide.

In preferred embodiments, the RNA silencing agent is capable of inducing discriminatory RNA silencing.

In one embodiment, the antisense strand of said RNA silencing agent is complementary to the SNP and wherein said RNA silencing agent is capable of substantially silencing the mutant huntingtin protein without substantially silencing the corresponding wild-type huntingtin protein.

In one aspect, the invention features a method of silencing mutant huntingtin (htt) mRNA in a HD patient population, comprising administering to said patient population an effective amount of a first RNA silencing agent targeting a HD-associated htt single nucleotide polymorphism (SNP) in combination with one or more RNA silencing agents targeting other htt SNPs, such that RNA silencing of said mRNA occurs, said one or more other htt SNPs having frequency of heterozygosity of at least 20%, 30%, 35% or more in a sample population. In one embodiment, the HD-associated htt SNP is present at genomic site RS362307. In another embodiment, the other htt SNPs are as set forth in any of Tables 1, 2, 5 and 6. In another embodiment, the other htt SNPs are selected from the group consisting of rs4690074, rs362336, rs362331, rs362373, rs362272, rs362306, rs362268, and rs362267. In one embodiment, the patient population is of US or Western European origin.

In another aspect, the invention features a method of silencing mutant htt mRNA in 70% or more HD patients in a HD patient population, comprising administering to said patients in the HD patient population one or more RNA silencing agents, wherein each RNA silencing agent targets a htt single nucleotide polymorphism (SNP) having a frequency of heterozygosity of at least 20% or more in a sample HD patient population, such that RNA silencing of said mRNA occurs in 70% or more patients in the HD patient population. In one embodiment the method further comprises identifying the sequence of the nucleotide located at one or more SNPs selected from the group consisting of rs362307, rs363125 and rs362273 in the mutant htt mRNA of the HD patients in the HD patient population. In one embodiment, the RNA silencing agents target SNP1, SNP2, and SNP3 as set forth in Table 2.

In another aspect, the invention features a method of silencing mutant huntingtin (htt) mRNA in 70% or more HD patients in a HD patient population, comprising administering to said patients in the HD patient population one or more RNA silencing agents, wherein each RNA silencing agent targets a htt single nucleotide polymorphism (SNP) selected from the group consisting of rs362307, rs363125 and rs362273, such that RNA silencing of said mRNA occurs in 70% or more patients in the HD patient population. In one embodiment of the foregoing aspects, the RNA silencing agent is a siRNA or a shRNA. In another embodiment, the foregoing method further comprises identifying the sequence of the nucleotide located at one or more SNPs selected from the group consisting of rs362307, rs363125 and rs362273 in the mutant htt mRNA of the HD patients in the HD patient population.

In one embodiment of the foregoing aspects, a nucleotide complementary to the SNP in the mutant htt mRNA is located at position 10 relative to the 5' end of the antisense strand of the RNA silencing agent. In one embodiment, the RNA silencing agent further comprises a mismatch with respect to both the mutant htt mRNA and the wild-type htt mRNA at one or more positions located within the seed sequence of the RNA silencing agent. In one embodiment said one or more positions are selected from the group consisting of position 2, position 3, position 4, position 5, position 6, and position 7 relative to the 5' end of the antisense strand of the RNA silencing agent, e.g., position 5 or position 6.

In another aspect, the invention features a method of silencing mutant huntingtin (htt) mRNA in 70% or more HD patients in a HD patient population, comprising administering to said patients in the HD patient population one or more siRNAs each comprising a guide strand and a complementary strand, wherein the guide strand is selected from the group consisting of SEQ ID NO:210, SEQ ID NO:211, SEQ ID NO:220, SEQ ID NO:230, and SEQ ID NO:233, such that RNA silencing of said mRNA occurs in 70% or more patients in the HD patient population.

In another aspect, the invention features a method of silencing mutant huntingtin (htt) mRNA in 70% or more HD patients in a HD patient population, comprising administering to said patients in the HD patient population one or more siRNAs each comprising a guide strand and a complementary strand, wherein the guide strand is selected from the group consisting of SEQ ID NO:210, SEQ ID NO:211, SEQ ID NO:219, SEQ ID NO:230, and SEQ ID NO:233, such that RNA silencing of said mRNA occurs in 70% or more patients in the HD patient population.

In another aspect, the invention features a siRNA comprising a guide strand and a complementary strand, wherein said guide strand has a nucleotide sequence set forth in Table 6 (SEQ ID NOs: 208-233). In another aspect, the invention features a siRNA comprising a guide strand and a complementary strand, wherein the guide strand has the nucleotide sequence of SEQ ID NO:219 or SEQ ID NO:220. In another aspect, the invention features a siRNA comprising a guide strand and a complementary strand, wherein the guide strand has the nucleotide sequence of SEQ ID NO:210 or SEQ ID NO:211. In another aspect, the invention features a siRNA comprising a guide strand and a complementary strand, wherein the guide strand has the nucleotide sequence of SEQ ID NO:230 or SEQ ID NO:228

In another aspect, the invention features a kit comprising a first RNA silencing agent targeting a HD-associated htt single nucleotide polymorphism (SNP); one or more additional RNA silencing agents targeting other htt SNPs having a frequency of heterozygosity of at least 20%, 30%, 35% or more in a sample population; and instructions for administration of one or more of the RNA silencing agents to a subject having Huntington's disease.

In another aspect, the invention features a kit comprising one or more siRNAs comprising a guide strand and a complementary strand, wherein said guide strand has a nucleotide sequence set forth in Table 6 (SEQ ID NOs:208-233); and instructions for use thereof for silencing mutant huntingtin (htt) mRNA in a subject having Huntington's disease. In one embodiment, the first silencing agent targets htt SNP rs362307, and the additional RNA silencing agents target htt SNPs rs363125 and rs362273.

Other features and advantages of the invention will be apparent from the following detailed description.

BRIEF DESCRIPTION OF THE DRAWINGS

FIG. 2: Repression of luciferase expression in reporter assays corresponds to depletion of endogenous Huntingtin mRNA. (A) Matched and mismatched siRNAs targeting the SNP rs363125 at nt 5,304 of Huntingtin mRNA. siRNAs are shown in capital letters with the passenger strand at top and the guide stranded paired to the mRNA, in lower case letters. The mismatch is at siRNA position 10. Dose-response analysis for these siRNAs includes (B) transfected plasmids expressing luciferase reporters and (C) quantitative RT-PCR assays measuring endogenous Huntingtin mRNA. Hela cells are homozygous for the C isoform of this SNP.

FIG. 12a-k: Human huntingtin gene, nucleotide sequence (SEQ ID NO:48).

FIG. 13a-b: Human huntingtin protein, amino acid sequence (SEQ ID NO:49).

DETAILED DESCRIPTION OF THE INVENTION

Figure 1A:
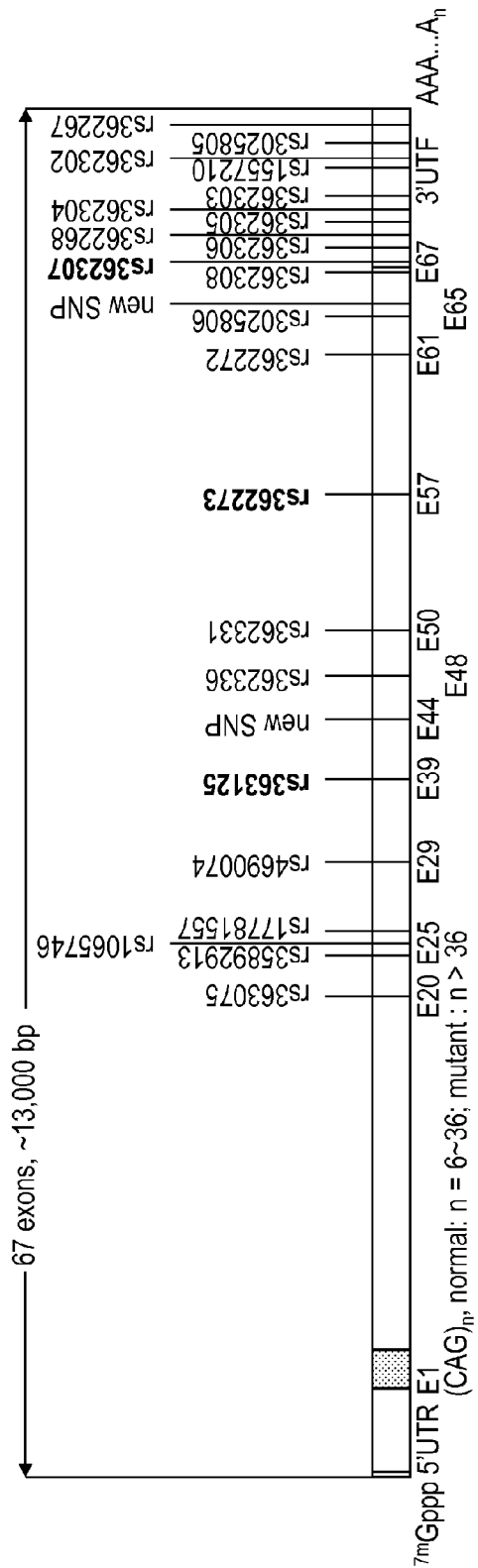
FIG. 1: Analysis of SNPs in the human Huntingtin mRNA. (A) PCR amplicons from genomic DNA from 109 HD patients and 116 controls spanning 22 SNP sites within the Huntingtin mRNA were sequenced. The SNP at nucleotide 9,633 (rs362307) is associated with HD and sites for which siRNAs were designed are in bold. (B) The maximum percentage of patients to have at least one heterozygous SNP using any combination of 1 to 7 SNPs was calculated using the experimentally determined frequency of heterozygosity for the SNP sites in our study. Three SNPs cover ~75% of the patient population analyzed here.

The present invention relates to methods and reagents for treating Huntington's Disease (HD).

The present invention utilizes RNA silencing technology (e.g. RNAi) against single nucleotide polymorphisms (SNPs) located within the htt gene encoding the mutant Huntingtin protein. RNA silencing destroys the corresponding mutant mRNA with single nucleotide specificity and selectivity. In some embodiments, RNA silencing agents as described herein are targeted to polymorphic regions of the mutant htt gene significantly associated with HD, resulting in silencing of mutant htt mRNA. Targeting such polymorphic regions provides a means for therapeutic treatment of a significant percentage of patients in a HD patent population. Targeting such polymorphic regions in combination with other selected polymorphic regions provides for even greater patient population coverage. Further therapeutic efficiency is achieved by enhancing the single-nucleotide selectivity of one or more of the featured silencing agents.

Definitions

So that the invention may be more readily understood, certain terms are first defined.

As used herein, the term "RNA silencing" refers to a group of sequence-specific regulatory mechanisms (e.g. RNA interference (RNAi), transcriptional gene silencing (TGS), post-transcriptional gene silencing (PTGS), quelling, co-suppression, and translational repression) mediated by RNA molecules which result in the inhibition or "silencing" of the expression of a corresponding protein-coding gene. RNA silencing has been observed in many types of organisms, including plants, animals, and fungi.

The term "discriminatory RNA silencing" refers to the ability of an RNA molecule to substantially inhibit the expression of a "first" or "target" polynucleotide sequence while not substantially inhibiting the expression of a "second" or "non-target" polynucleotide sequence", e.g., when both polynucleotide sequences are present in the same cell. In certain embodiments, the target polynucleotide sequence corresponds to a target gene, while the non-target polynucleotide sequence corresponds to a non-target gene. In other embodiments, the target polynucleotide sequence corresponds to a target allele, while the non-target polynucleotide sequence corresponds to a non-target allele. In certain embodiments, the target polynucleotide sequence is the DNA sequence encoding the regulatory region (e.g. promoter or enhancer elements) of a target gene. In other embodiments, the target polynucleotide sequence is a target mRNA encoded by a target gene.

As used herein, the term "target gene" is a gene whose expression is to be substantially inhibited or "silenced." This silencing can be achieved by RNA silencing, e.g. by cleaving the mRNA of the target gene (or target mRNA) or translational repression of the target gene (e.g., the mRNA of the non-target gene is not cleaved, or is cleaved to a degree significantly less than the corresponding target mRNA). The term "non-target gene" is a gene whose expression is not to be substantially silenced. In one embodiment, the polynucleotide sequences of the target and non-target gene (e.g. mRNA encoded by the target and non-target genes) can differ by one or more nucleotides. In another embodiment, the target and non-target genes can differ by one or more polymorphisms (e.g., Single Nucleotide Polymorphisms or SNPs). In another embodiment, the target and non-target genes can share less than 100% sequence identity. In another embodiment, the non-target gene may be a homolog (e.g. an ortholog or paralog) of the target gene.

A "target allele" is an allele (e.g., a SNP allele) whose expression is to be selectively inhibited or "silenced." This silencing can be achieved by RNA silencing, e.g. by cleaving the mRNA of the target gene (or target mRNA) or target allele by a siRNA. The term "non-target allele" is a allele whose expression is not to be substantially silenced (e.g., the mRNA of the non-target allele is not cleaved, or is cleaved to a degree significantly less than the corresponding target mRNA). In certain embodiments, the target and non-target alleles can correspond to the same target gene. In other embodiments, the target allele corresponds to, or is associated with, a target gene, and the non-target allele corresponds to, or is associated with, a non-target gene. In one embodiment, the polynucleotide sequences of the target and non-target alleles can differ by one or more nucleotides. In another embodiment, the target and non-target alleles can differ by one or more allelic polymorphisms (e.g., one or more SNPs). In another embodiment, the target and non-target alleles can share less than 100% sequence identity.

The term "polymorphism" as used herein, refers to a variation (e.g., one or more deletions, insertions, or substitutions) in a gene sequence that is identified or detected when the same gene sequence from different sources or subjects (but from the same organism) are compared. For example, a polymorphism can be identified when the same gene sequence from different subjects are compared. Identification of such polymorphisms is routine in the art, the methodologies being similar to those used to detect, for example, breast cancer point mutations. Identification can be made, for example, from DNA extracted from a subject's lymphocytes, followed by amplification of polymorphic regions using specific primers to said polymorphic region. Alternatively, the polymorphism can be identified when two alleles of the same gene are compared. In particular embodiments, the polymorphism is a single nucleotide polymorphism (SNP).

A variation in sequence between two alleles of the same gene within an organism is referred to herein as an "allelic polymorphism". In certain embodiments, the allelic polymorphism corresponds to a SNP allele. For example, the allelic polymorphism may comprise a single nucleotide variation between the two alleles of a SNP. The polymorphism can be at a nucleotide within a coding region but, due to the degeneracy of the genetic code, no change in amino acid sequence is encoded. Alternatively, polymorphic sequences can encode a different amino acid at a particular position, but the change in the amino acid does not affect protein function. Polymorphic regions can also be found in non-encoding regions of the gene. In preferred embodiments, the polymorphism is found in a coding region of the gene or in an untranslated region (e.g., a 5' UTR or 3' UTR) of the gene.

As used herein, the term "allelic frequency" is a measure (e.g., proportion or percentage) of the relative frequency of an allele (e.g., a SNP allele) at a single locus in a population of individuals. For example, where a population of individuals carry n loci of a particular chromosomal locus (and the gene occupying the locus) in each of their somatic cells, then the allelic frequency of an allele is the fraction or percentage of loci that the allele occupies within the population. In particular embodiments, the allelic frequency of an allele (e.g. a SNP allele) is at least 10% (e.g., at least 15%, 20%, 25%, 30%, 35%, 40% or more) in a sample population. In particular embodiments, the allelic frequency of an allele (e.g., a SNP allele) is at least 45% or more in a sample population. Allelic frequency likewise refers to the percentage of individuals that contain two or more different alleles of a gene at a particular locus, e.g., at a SNP locus. Accordingly, allelic frequency can also be referred to herein as frequency of heterozygosity. For example, as described herein, if 30% of the individuals in a population possess alleles of a gene that differ in nucleotide sequence at a particular SNP locus, that SNP locus has a 30% frequency of heterozygosity (or a 30% allelic frequency) in the population.

As used herein, the term "frequency of heterozygosity" refers to a fraction of individuals within a population that are heterozygous (e.g., contain two different alleles) at a particular locus (e.g., at a SNP). Frequency of heterozygosity may be calculated for a sample population using methods that are well known to those skilled in the art.

As used herein, the term "HD associated" (e.g., "HD associated SNP") refers to a particular isoform of a polymorphism that is predominantly associated with the disease allele, rather than the normal allele, of the Huntingtin gene. For example, the U isoform of the rs362307 SNP comprises 26% of Huntingtin disease alleles, but only 6% of normal alleles of the Huntingtin gene, as described herein. Accordingly, the U isoform of rs362307 is a HD-associated SNP.

As used herein, the term "sample population" refers to a population of individuals comprising a statistically significant number of individuals. For example, the sample population may comprise 50, 75, 100, 200, 500, 1000 or more individuals. In particular embodiments, the sample population may comprise individuals which share at least on common disease phenotype (e.g., a gain-of-function disorder) or mutation (e.g., a gain-of-function mutation). Such a population may be screened to determine the frequency of heterozygosity of a particular gene locus (e.g., the frequency of heterozygosity of a SNP site).

The term "gain-of-function mutation" as used herein, refers to any mutation in a gene in which the protein encoded by said gene (i.e., the mutant protein) acquires a function not normally associated with the protein (i.e., the wild type protein) causes or contributes to a disease or disorder. The gain-of-function mutation can be a deletion, addition, or substitution of a nucleotide or nucleotides in the gene which gives rise to the change in the function of the encoded protein. In one embodiment, the gain-of-function mutation changes the function of the mutant protein or causes interactions with other proteins. In another embodiment, the gain-of-function mutation causes a decrease in or removal of normal wild-type protein, for example, by interaction of the altered, mutant protein with said normal, wild-type protein.

As used herein, the term "gain-of-function disorder", refers to a disorder characterized by a gain-of-function mutation. In one embodiment, the gain-of-function disorder is a neurodegenerative disease caused by a gain-of-function mutation, e.g., polyglutamine disorders and/or trinucleotide repeat diseases, for example, Huntington's disease. In another embodiment, the gain-of-function disorder is caused by a gain-of-function in an oncogene, the mutated gene product being a gain-of-function mutant, e.g., cancers caused by a mutation in the ret oncogene (e.g., ret-1), for example, endocrine tumors, medullary thyroid tumors, parathyroid hormone tumors, multiple endocrine neoplasia type2, and the like. Additional exemplary gain-of-function disorders include Alzheimer's, human immunodeficiency disorder (HIV), and slow channel congenital myasthenic syndrome (SCCMS).

The term "trinucleotide repeat diseases" as used herein, refers to any disease or disorder characterized by an expanded trinucleotide repeat region located within a gene, the expanded trinucleotide repeat region being causative of the disease or disorder. Examples of trinucleotide repeat diseases include, but are not limited to spino-cerebellar ataxia type 12 spino-cerebellar ataxia type 8, fragile X syndrome, fragile XE Mental Retardation, Friedreich's ataxia and myotonic dystrophy. Preferred trinucleotide repeat diseases for treatment according to the present invention are those characterized or caused by an expanded trinucleotide repeat region at the 5' end of the coding region of a gene, the gene encoding a mutant protein which causes or is causative of the disease or disorder. Certain trinucleotide diseases, for example, fragile X syndrome, where the mutation is not associated with a coding region may not be suitable for treatment according to the methodologies of the present invention, as there is no suitable mRNA to be targeted by RNAi. By contrast, disease such as Friedreich's ataxia may be suitable for treatment according to the methodologies of the invention because, although the causative mutation is not within a coding region (i.e., lies within an intron), the mutation may be within, for example, an mRNA precursor (e.g., a pre-spliced mRNA precursor).

The term "polyglutamine disorder" as used herein, refers to any disease or disorder characterized by an expanded of a $(CAG)_n$ repeats at the 5' end of the coding region (thus encoding an expanded polyglutamine region in the encoded protein). In one embodiment, polyglutamine disorders are characterized by a progressive degeneration of nerve cells. Examples of polyglutamine disorders include but are not limited to: Huntington's disease, spino-cerebellar ataxia type 1, spino-cerebellar ataxia type 2, spino-cerebellar ataxia type 3 (also know as Machado-Joseph disease), and spino-cerebellar ataxia type 6, spino-cerebellar ataxia type 7 and dentatoiubral-pallidoluysian atrophy.

The term "polyglutamine domain," as used herein, refers to a segment or domain of a protein that consist of a consecutive glutamine residues linked to peptide bonds. In one embodiment the consecutive region includes at least 5 glutamine residues.

The term "expanded polyglutamine domain" or "expanded polyglutamine segment", as used herein, refers to a segment or domain of a protein that includes at least 35 consecutive glutamine residues linked by peptide bonds. Such expanded segments are found in subjects afflicted with a polyglutamine disorder, as described herein, whether or not the subject has shown to manifest symptoms.

The term "trinucleotide repeat" or "trinucleotide repeat region" as used herein, refers to a segment of a nucleic acid sequence e.g.) that consists of consecutive repeats of a particular trinucleotide sequence. In one embodiment, the trinucleotide repeat includes at least 5 consecutive trinucleotide sequences. Exemplary trinucleotide sequences include, but are not limited to, CAG, CGG, GCC, GAA, CTG, and/or CGG.

As used herein, the term "RNA silencing agent" refers to an RNA which is capable of inhibiting or "silencing" the expression of a target gene. In certain embodiments, the RNA silencing agent is capable of preventing complete processing (e.g, the full translation and/or expression) of a mRNA molecule through a post-transcriptional silencing mechanism. RNA silencing agents include small (<50 b.p.), noncoding RNA molecules, for example RNA duplexes comprising paired strands, as well as precursor RNAs from which such small non-coding RNAs can be generated. Exemplary RNA silencing agents include siRNAs, shRNAs, miRNAs, siRNA-like duplexes, and dual-function oligonucleotides as well as precursors thereof. In one embodiment, the RNA silencing agent is capable of inducing RNA interference. In another embodiment, the RNA silencing agent is capable of mediating translational repression.

The term "nucleoside" refers to a molecule having a purine or pyrimidine base covalently linked to a ribose or deoxyribose sugar. Exemplary nucleosides include adenosine, guanosine, cytidine, uridine and thymidine. Additional exemplary nucleosides include inosine, 1-methyl inosine, pseudouridine, 5,6-dihydrouridine, ribothymidine, $^2$N-methylguanosine and $^{2,2}$N,N-dimethylguanosine (also referred to as "rare" nucleosides). The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester linkage between 5' and 3' carbon atoms.

The term "RNA" or "RNA molecule" or "ribonucleic acid molecule" refers to a polymer of ribonucleotides (e.g., 2, 3, 4, 5, 10, 15, 20, 25, 30, or more ribonucleotides). The term "DNA" or "DNA molecule" or deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

As used herein, the term "rare nucleotide" refers to a naturally occurring nucleotide that occurs infrequently, including naturally occurring deoxyribonucleotides or ribonucleotides that occur infrequently, e.g., a naturally occurring ribonucleotide that is not guanosine, adenosine, cytosine, or uridine. Examples of rare nucleotides include, but are not limited to, inosine, 1-methyl inosine, pseudouridine, 5,6-dihydrouridine, ribothymidine, $^2$N-methylguanosine and $^{2,2}$N,N-dimethylguanosine.

The term "engineered," as in an engineered RNA precursor, or an engineered nucleic acid molecule, indicates that the precursor or molecule is not found in nature, in that all or a portion of the nucleic acid sequence of the precursor or molecule is created or selected by man. Once created or selected, the sequence can be replicated, translated, transcribed, or otherwise processed by mechanisms within a cell. Thus, an RNA precursor produced within a cell from a transgene that includes an engineered nucleic acid molecule is an engineered RNA precursor.

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference. Preferably, a siRNA comprises between about 15-30 nucleotides or nucleotide analogs, more preferably between about 16-25 nucleotides (or nucleotide analogs), even more preferably between about 18-23 nucleotides (or nucleotide analogs), and even more preferably between about 19-22 nucleotides (or nucleotide analogs) (e.g., 19, 20, 21 or 22 nucleotides or nucleotide analogs). The term "short" siRNA refers to a siRNA comprising ~21 nucleotides (or nucleotide analogs), for example, 19, 20, 21 or 22 nucleotides. The term "long" siRNA refers to a siRNA comprising ~24-25 nucleotides, for example, 23, 24, 25 or 26 nucleotides. Short siRNAs may, in some instances, include fewer than 19 nucleotides, e.g., 16, 17 or 18 nucleotides, provided that the shorter siRNA retains the ability to mediate RNAi. Likewise, long siRNAs may, in some instances, include more than 26 nucleotides, provided that the longer siRNA retains the ability to mediate RNAi absent further processing, e.g., enzymatic processing, to a short siRNA. A "single-nucleotide-selective" siRNA is one that predominantly cleaves the target mRNA versus the non-target mRNA (also referred to herein as the "counter-selected mRNA" target).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region.

As used herein, the term "microRNA" ("miRNA"), also referred to in the art as "small temporal RNAs" ("stRNAs"), refers to a small (10-50 nucleotide) RNA which are genetically encoded (e.g. by viral, mammalian, or plant genomes) and are capable of directing or mediating RNA silencing. An "miRNA disorder" shall refer to a disease or disorder characterized by an aberrant expression or activity of an miRNA.

As used herein, the term "dual functional oligonucleotide" refers to a RNA silencing agent having the formula T-L-μ, wherein T is an mRNA targeting moiety, L is a linking moiety, and μ is a miRNA recruiting moiety. As used herein, the terms "mRNA targeting moiety", "targeting moiety", "mRNA targeting portion" or "targeting portion" refer to a domain, portion or region of the dual functional oligonucleotide having sufficient size and sufficient complementarity to a portion or region of an mRNA chosen or targeted for silencing (i.e., the moiety has a sequence sufficient to capture the target mRNA). As used herein, the term "linking moiety" or "linking portion" refers to a domain, portion or region of the RNA-silencing agent which covalently joins or links the mRNA As used herein, the term "antisense strand" of an RNA silencing agent, e.g. an siRNA or RNA silencing agent, refers to a strand that is substantially complementary to a section of about 10-50 nucleotides, e.g., about 15-30, 16-25, 18-23 or 19-22 nucleotides of the mRNA of the gene targeted for silencing. The antisense strand or first strand has sequence sufficiently complementary to the desired target mRNA sequence to direct target-specific silencing, e.g., complementarity sufficient to trigger the destruction of the desired target mRNA by the RNAi machinery or process (RNAi interference) or complementarity sufficient to trigger translational repression of the desired target mRNA.

The term "sense strand" or "second strand" of an RNA silencing agent, e.g. an siRNA or RNA silencing agent, refers to a strand that is complementary to the antisense strand or first strand. Antisense and sense strands can also be referred to as first or second strands, the first or second strand having complementarity to the target sequence and the respective second or first strand having complementarity to said first or second strand. miRNA duplex intermediates or siRNA-like duplexes include a miRNA strand having sufficient complementarity to a section of about 10-50 nucleotides of the mRNA of the gene targeted for silencing and a miRNA* strand having sufficient complementarity to form a duplex with the miRNA strand.

As used herein, the term "guide strand" refers to a strand of an RNA silencing agent, e.g., an antisense strand of an siRNA duplex or siRNA sequence, that enters into the RISC complex and directs cleavage of the target mRNA.

The term "nucleotide analog" or "altered nucleotide" or "modified nucleotide" refers to a non-standard nucleotide, including non-naturally occurring ribonucleotides or deoxyribonucleotides. Preferred nucleotide analogs are modified at any position so as to alter certain chemical properties of the nucleotide yet retain the ability of the nucleotide analog to perform its intended function. Examples of positions of the nucleotide which may be derivitized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, Antisense Nucleic Acid Drug Dev., 2000 Aug. 10(4):297-310.

Nucleotide analogs may also comprise modifications to the sugar portion of the nucleotides. For example the 2' OH-group may be replaced by a group selected from H, OR, R, F, Cl, Br, I, SH, SR, $NH_2$, NHR, $NR_2$, COOR, or OR, wherein R is substituted or unsubstituted $C_1$-$C_6$ alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, Antisense Nucleic Acid Drug Dev. 2000 Apr. 10(2):117-21, Ruschkowski et al. Antisense Nucleic Acid Drug Dev. 2000 Oct. 10(5):333-45, Stein, Antisense Nucleic Acid Drug Dev. 2001 Oct. 11(5): 317-25, Vorobjev et al. Antisense Nucleic Acid Drug Dev. 2001 Apr. 11(2):77-85, and U.S. Pat. No. 5,684,143. Certain of the above-referenced modifications (e.g., phosphate group modifications) preferably decrease the rate of hydrolysis of, for example, polynucleotides comprising said analogs in vivo or in vitro.

As used herein, the term "asymmetry", as in the asymmetry of the duplex region of an RNA silencing agent (e.g. the stem of an shRNA), refers to an inequality of bond strength or base pairing strength between the termini of the RNA silencing agent (e.g., between terminal nucleotides on a first strand or stem portion and terminal nucleotides on an opposing second strand or stem portion), such that the 5' end of one strand of the duplex is more frequently in a transient unpaired, e.g, single-stranded, state than the 5' end of the complementary strand. This structural difference determines that one strand of the duplex is preferentially incorporated into a RISC complex. The strand whose 5' end is less tightly paired to the complementary strand will preferentially be incorporated into RISC and mediate RNAi.

As used herein, the term "bond strength" or "base pair strength" refers to the strength of the interaction between pairs of nucleotides (or nucleotide analogs) on opposing strands of an oligonucleotide duplex (e.g., an siRNA duplex), due primarily to H-bonding, Van der Waals interactions, and the like between said nucleotides (or nucleotide analogs).

As used herein, the "5' end", as in the 5' end of an antisense strand, refers to the 5' terminal nucleotides, e.g., between one and about 5 nucleotides at the 5' terminus of the antisense strand. As used herein, the "3' end", as in the 3' end of a sense strand, refers to the region, e.g., a region of between one and about 5 nucleotides, that is complementary to the nucleotides of the 5' end of the complementary antisense strand.

As used herein the term "destabilizing nucleotide" refers to a first nucleotide or nucleotide analog capable of forming a base pair with second nucleotide or nucleotide analog such that the base pair is of lower bond strength than a conventional base pair (ie. Watson-Crick base pair). In certain embodiments, the destabilizing nucleotide is capable of forming a mismatch base pair with the second nucleotide. In other embodiments, the destabilizing nucleotide is capable of forming a wobble base pair with the second nucleotide. In yet other embodiments, the destabilizing nucleotide is capable of forming an ambiguous base pair with the second nucleotide.

As used herein, the term "base pair" refers to the interaction between pairs of nucleotides (or nucleotide analogs) on opposing strands of an oligonucleotide duplex (e.g., a duplex formed by a strand of a RNA silencing agent and a target mRNA sequence), due primarily to H-bonding, Van der Waals interactions, and the like between said nucleotides (or nucleotide analogs). As used herein, the term "bond strength" or "base pair strength" refers to the strength of the base pair.

As used herein, the term "mismatched base pair" refers to a base pair consisting of noncomplementary or non-Watson-Crick base pairs, for example, not normal complementary G:C, A:T or A:U base pairs. As used herein the term "ambiguous base pair" (also known as a non-discriminatory base pair) refers to a base pair formed by a universal nucleotide.

As used herein, term "universal nucleotide" (also known as a "neutral nucleotide") include those nucleotides (e.g. certain destabilizing nucleotides) having a base (a "universal base" or "neutral base") that does not significantly discriminate between bases on a complementary polynucleotide when forming a base pair. Universal nucleotides are predominantly hydrophobic molecules that can pack efficiently into antiparallel duplex nucleic acids (e.g. double-stranded DNA or RNA) due to stacking interactions. The base portion of universal nucleotides typically comprise a nitrogen-containing aromatic heterocyclic moiety.

As used herein, the terms "sufficient complementarity" or "sufficient degree of complementarity" mean that the RNA silencing agent has a sequence (e.g. in the antisense strand, mRNA targeting moiety or miRNA recruiting moiety) which is sufficient to bind the desired target RNA, respectively, and to trigger the RNA silencing of the target mRNA.

The term "oligonucleotide" refers to a short polymer of nucleotides and/or nucleotide analogs. The term "RNA analog" refers to an polynucleotide (e.g., a chemically synthesized polynucleotide) having at least one altered or modified nucleotide as compared to a corresponding unaltered or unmodified RNA but retaining the same or similar nature or function as the corresponding unaltered or unmodified RNA. As discussed above, the oligonucleotides may be linked with linkages which result in a lower rate of hydrolysis of the RNA analog as compared to an RNA molecule with phosphodiester linkages. For example, the nucleotides of the analog may comprise methylenediol, ethylene diol, oxymethylthio, oxyethylthio, oxycarbonyloxy, phosphorodiamidate, phosphoroamidate, and/or phosphorothioate linkages. Preferred RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate (mediates) RNA interference.

As used herein, the term "RNA interference" ("RNAi") refers to a selective intracellular degradation of RNA. RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of target genes.

As used herein, the term "translational repression" refers to a selective inhibition of mRNA translation. Natural translational repression proceeds via miRNAs cleaved from shRNA precursors. Both RNAi and translational repression are mediated by RISC. Both RNAi and translational repression occur naturally or can be initiated by the hand of man, for example, to silence the expression of target genes.

An RNA silencing agent having a strand which is "sequence sufficiently complementary to a target mRNA sequence to direct target-specific RNA interference (RNAi)" means that the strand has a sequence sufficient to trigger the destruction of the target mRNA by the RNAi machinery or process.

As used herein, the term "isolated RNA" (e.g., "isolated siRNA" or "isolated siRNA precursor") refers to RNA molecules which are substantially free of other cellular material, or culture medium when produced by recombinant techniques, or substantially free of chemical precursors or other chemicals when chemically synthesized.

The term "in vitro" has its art recognized meaning, e.g., involving purified reagents or extracts, e.g., cell extracts. The term "in vivo" also has its art recognized meaning, e.g., involving living cells, e.g., immortalized cells, primary cells, cell lines, and/or cells in an organism.

As used herein, the term "transgene" refers to any nucleic acid molecule, which is inserted by artifice into a cell, and becomes part of the genome of the organism that develops from the cell. Such a transgene may include a gene that is partly or entirely heterologous (i.e., foreign) to the transgenic organism, or may represent a gene homologous to an endogenous gene of the organism. The term "transgene" also means a nucleic acid molecule that includes one or more selected nucleic acid sequences, e.g., DNAs, that encode one or more engineered RNA precursors, to be expressed in a transgenic organism, e.g., animal, which is partly or entirely heterologous, i.e., foreign, to the transgenic animal, or homologous to an endogenous gene of the transgenic animal, but which is designed to be inserted into the animal's genome at a location which differs from that of the natural gene. A transgene includes one or more promoters and any other DNA, such as introns, necessary for expression of the selected nucleic acid sequence, all operably linked to the selected sequence, and may include an enhancer sequence.

The phrase "examining the function of a gene in a cell or organism" refers to examining or studying the expression, activity, function or phenotype arising therefrom.

Various methodologies of the instant invention include step that involves comparing a value, level, feature, characteristic, property, etc. to a "suitable control", referred to interchangeably herein as an "appropriate control". A "suitable control"

or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing an RNA silencing agent of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Various aspects of the invention are described in further detail in the following subsections.

I. Huntington Disease

The RNA silencing agents of the invention are designed to target polymorphisms (e.g. single nucleotide polymorphisms) in the mutant human huntingtin protein (htt) for the treatment of Huntington's disease.

Huntington's disease, inherited as an autosomal dominant disease, causes impaired cognition and motor disease. Patients can live more than a decade with severe debilitation, before premature death from starvation or infection. The disease begins in the fourth or fifth decade for most cases, but a subset of patients manifest disease in teenage years. The genetic mutation for Huntington's disease is a lengthened CAG repeat in the huntingtin gene. The CAG repeat varies in number from 8 to 35 copies in normal individuals (Kremer et al., 1994). The genetic mutation (e.g., an increase in length of the CAG repeats from less than 36 in the normal huntingtin gene to greater than 36 in the disease) is associated with the synthesis of a mutant huntingtin protein, which has greater than 36 consecutive polyglutamine residues (Aronin et al., 1995). In general, individuals with 36 or more CAG repeats will get Huntington's disease. Prototypic for as many as twenty other diseases with a lengthened CAG as the underlying mutation, Huntington's disease still has no effective therapy. A variety of interventions—such as interruption of apoptotic pathways, addition of reagents to boost mitochondrial efficiency, and blockade of NMDA receptors—have shown promise in cell cultures and mouse model of Huntington's disease. However, at best these approaches reveal a short prolongation of cell or animal survival.

Huntington's disease complies with the central dogma of genetics: a mutant gene serves as a template for production of a mutant mRNA; the mutant mRNA then directs synthesis of a mutant protein (Aronin et al., 1995; DiFiglia et al., 1997). Mutant huntingtin (protein) probably accumulates in selective neurons in the striatum and cortex, disrupts as yet determined cellular activities, and causes neuronal dysfunction and death (Aronin et al., 1999; Laforet et al., 2001). Because a single copy of a mutant gene suffices to cause Huntington's disease, the most parsimonious treatment would render the mutant gene ineffective. Theoretical approaches might include stopping gene transcription of mutant huntingtin, destroying mutant mRNA, and blocking translation. Each has the same outcome—loss of mutant huntingtin.

The disease gene linked to Huntington's disease is termed Huntington or (htt). The huntingtin locus is large, spanning 180 kb and consisting of 67 exons. The huntingtin gene is widely expressed and is required for normal development. It is expressed as 2 alternatively polyadenylated forms displaying different relative abundance in various fetal and adult tissues. The larger transcript is approximately 13.7 kb and is expressed predominantly in adult and fetal brain whereas the smaller transcript of approximately 10.3 kb is more widely expressed. The two transcripts differ with respect to their 3' untranslated regions (Lin et al., 1993). Both messages are predicted to encode a 348 kilodalton protein containing 3144 amino acids. The genetic defect leading to Huntington's disease is believed to confer a new property on the mRNA or alter the function of the protein. The amino acid sequence of the human huntingtin protein is set as SEQ ID NO: 49.

A consensus nucleotide sequence of the human huntingtin gene (cDNA) is set forth as SEQ ID NO: 48. The coding region consists of nucleotides 316 to 9750 of SEQ ID NO:48. The two alternative polyadenylation signals are found at nucleotides 10326 to 10331 and nucleotides 13644 to 13649, respectively. The corresponding two polyadenylation sites are found at nucleotides 10348 and 13672, respectively. The first polyadenylation signal/site is that of the 10.3 kb transcript. The second polyadenylation signal/site is that of the 13.7 kb transcript, the predominant transcript in brain.

i. Hungtinton SNPs

Exemplary single nucleotide polymorphisms in the huntingtin gene sequence, including 22 known SNP sites and 2 SNP sites identified in instant invention, are illustrated in FIG. 1. Genomic sequence for each SNP site can be found in, for example, the publically available "SNP Entrez" database maintained by the NCBI. The frequency of heterozygosity for each SNP site for HD patient and control DNA is further illustrated in Table 1. Targeting combinations of frequently heterozygous SNPs allows the treatment of a large percentage of the individuals in a HD population using a relatively small number of allele-specific RNA silencing agents. As described herein, the U isoform of the rs362307 SNP was present in a high percentage of mutant htt alleles, but only a small percentage of normal alleles of the Huntingtin gene. Accordingly, a single RNA silencing agent targeting this site can be used to selectively silence the mutant htt allele in a large percentage of subjects in a HD patient population. Alternatively, multiple RNA silencing agents can be used which each target this site to selectively silence the mutant htt allele in a large percentage of subjects in a HD patient population. Accordingly, in a particularly preferred embodiment, the SNP allele used for allele-specific silencing is present at genomic site rs362307.

As described herein, a number of additional SNP sites were heterozygous in a significant percentage of individuals having HD. As set forth herein, the number of patients having at least one heterozygous SNP site was calculated for combinations of these SNPs having a high frequency of heterozygosity. The instant inventors determined that a large percentage (e.g., 70-75%) of HD patients are heterozygous for one or more of three SNP sites having a high frequency of heterozygosity. Accordingly, by targeting three SNPs having a high frequency of heterozygosity, it is possible to treat a large percentage (e.g., 70-75%) of the HD population. Mutant huntingtin mRNA can be silenced in an individual within the population by administering to the individual one or more RNA silencing agents targeting one or more of the SNPs identified as having a high frequency of heterozygosity. When targeting SNP sites that have a high frequency of heterozygosity, even when they do not show a statistically significant association with HD, it may be desirable to target the particular isoform of these SNP sites present in the subject having HD. The identity of the nucleotide at a SNP locus on the disease and normal alleles of the Huntingtin gene can be determined by methods known to a skilled artisan, including, for example, by use of the SLiC method described by Liu et al., Nature Methods (2008), 5(11):951-953, the entire contents of which are incorporated herein by reference.

In one embodiment, RNA silencing agents of the invention are capable of targeting one of the SNP sites listed in FIG. 1. In one embodiment, RNA silencing agents of the invention are capable of targeting rs362307 SNP site at nucleotide (nt) 9,633 (3'UTR exon 67) of the Huntingtin mRNA. In another embodiment, RNA silencing agents of the invention are capable of targeting rs363125 SNP site at nucleotide (nt) 5304 (ORF exon 39) of the Huntingtin mRNA. In some preferred embodiments, RNA silencing agents of the invention are capable of targeting a combination of known SNP sites. In one preferred embodiment, combinations of RNA silencing agents of the invention are capable of targeting a combination of three known SNP sites. In a particular embodiment, combinations of RNA silencing agents of the invention are capable of targeting a combination of rs362307 SNP site plus two additional SNP sites listed as SNP2 and SNP3 in Table 2. In another particular embodiment, RNA silencing agents of the invention are capable of targeting a combination of rs363125 SNP site plus two additional SNP sites listed as SNP2 and SNP3 in Table 2. In some embodiments, SNP sites targeted by RNA silencing agents are associated with Huntington's Disease. In some preferred embodiments, SNP sites targeted by RNA silencing agents are significantly associated with Huntington's Disease.

The discovery that a large percentage of a HD patient population can be treated by targeting a relatively small number of SNPs makes it possible to design and test a small number of RNA silencing agents that are useful for administration alone or in combination to subjects in a HD population to achieve silencing of the mutant htt allele in a large percentage of the population. For example, the use of a total of five RNA silencing agents can be used to target over 70% of the HD population: one RNA silencing agent targeting the U isoform of HD-associated SNP rs362307, two RNA silencing agents each targeting one isoform of frequently heterozygous SNP rs363125, and two RNA silencing agents each targeting one isoform of frequently heterozygous SNP rs362273. Other combinations of minimal numbers of RNA silencing agents can readily be envisioned based on the foregoing methodology and the frequencies of SNP heterozygosity of htt SNPs set forth herein. This streamlined approach allows more rapid selection, screening and preclinical testing of RNA silencing agents that can be used to treat a large percentage of patients having HD.

The instant inventors identified several previously unidentified SNPs in the Huntingtin gene. These SNPs are located in exon 44 at nucleotide position 6150, and in exon 65, at nucleotide position 9175. RNA silencing agents targeting these SNPs can be used to achieve allele-specific silencing of the mutant Huntingtin gene. RNA silencing agents targeting these SNPs can be used alone or in combination with RNA silencing agents targeting other SNPs present in the Huntingtin gene in a HD subject or in a HD patient population.

ii. Anti-htt siRNAs

Anti-htt siRNAs to target any of the single nucleotide polymorphisms described supra. Said siRNAs comprise an antisense strand which is fully complementary with the single nucleotide polymorphism. In certain embodiments, the RNA silencing agent is a siRNA.

In certain embodiments, the siRNA comprises (i) an antisense (or guide) strand comprising the sequence set forth in Table 6; and (ii) a complementary (e.g., a perfectly complementary) sense strand.

To validate the effectiveness by which siRNAs destroy mutant mRNAs (e.g., mutant huntingtin mRNA), the siRNA is incubated with mutant cDNA (e.g., mutant huntingtin cDNA) in a *Drosophila*-based in vitro mRNA expression system. Radiolabeled with $^{32}$P, newly synthesized mutant mRNAs (e.g., mutant huntingtin mRNA) are detected autoradiographically on an agarose gel. The presence of cleaved mutant mRNA indicates mRNA nuclease activity. Suitable controls include omission of siRNA and use of wild-type huntingtin cDNA. Alternatively, control siRNAs are selected having the same nucleotide composition as the selected siRNA, but without significant sequence complementarity to the appropriate target gene. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence.

Sites of siRNA-mRNA complementation are selected which result in optimal mRNA specificity and maximal mRNA cleavage.

While the instant invention primarily features targeting polymorphic regions in the target mutant gene (e.g., in mutant htt) distinct from the expanded CAG region mutation, in particular, polymorphic regions significantly associated with HD, the skilled artisan will appreciate that targeting the mutant region may have applicability as a therapeutic strategy in certain situations. Targeting the mutant region can be accomplished using siRNA that complements CAG in series. The siRNA$^{cag}$ would bind to mRNAs with CAG complementation, but might be expected to have greater opportunity to bind to an extended CAG series. Multiple siRNA$^{cag}$ would bind to the mutant huntingtin mRNA (as opposed to fewer for the wild type huntingtin mRNA); thus, the mutant huntingtin mRNA is more likely to be cleaved. Successful mRNA inactivation using this approach would also eliminate normal or wild-type huntingtin mRNA. Also inactivated, at least to some extent, could be other normal genes (approximately 70) which also have CAG repeats, where their mRNAs could interact with the siRNA. This approach would thus rely on an attrition strategy—more of the mutant huntingtin mRNA would be destroyed than wild type huntingtin mRNA or the other approximately 69 mRNAs that code for polyglutamines.

TABLE 1

Frequency of Heterozygosity for 24 SNP sites in the Huntingtin mRNA

| Location in mRNA (position, nt) | Reference Number | Percent heterozygosity | |
|---|---|---|---|
| | | Controls | HD patients |
| ORF, exon 20 (2822) | rs363075 | G/A, 10.3% (G/G, 89.7%) | G/A, 12.8% (G/G, 86.2%; A/A 0.9% |
| ORF, exon 25 (3335) | rs35892913 | G/A, 10.3% (G/G, 89.7%) | G/A, 13.0% (G/G, 86.1%; A/A, 0.9% |
| ORF, exon 25 (3389) | rs1065746 | G/C, 0% (G/G 100%) | G/C, 0.9% (G/G 99.1%) |
| ORF, exon 25 (3418) | rs17781557 | T/G, 12.9% (T/T, 87.1%) | T/G, 1.9% (T/T, 98.1%) |
| ORF, exon 29 (3946) | rs4690074 | C/T, 37.9% (C/C, 50.9%; T/T, 11.2) | C/T, 35.8% (C/C, 59.6%; T/T, 4.6%) |
| ORF, exon 39 (5304) | rs363125 | C/A, 17.5% (C/C, 79.0%; A/A, 3.5%) | C/A, 11.0% (C/C, 87.2%; A/A, 1.8%) |
| ORF, exon 44 (6150) | exon 44 (new) | G/A, 0% (G/G, 100%) | G/A, 2.8% (G/G, 97.2%) |
| ORF, exon 48 (6736) | rs362336 | G/A, 38.7% (G/G, 49.6%; A/A, 11.7%) | G/A, 37.4% (G/G, 57.9%; A/A, 4.7%) |
| ORF, exon 50 (7070) | rs362331 | T/C, 45.7% (T/T, 31.0%; C/C, 23.3%) | T/C, 39.4% (T/T, 49.5%; C/C, 11.0%) |
| ORF, exon 57 (7942) | rs362273 | A/G, 40.3% (A/A, 48.2%; G/G, 11.4%) | A/G, 35.2% (A/A, 60.2%; G/G, 4.6%) |
| ORF, exon 61 (8501) | rs362272 | G/A, 37.1% (G/G, 51.7%; A/A, 11.2%) | G/A, 36.1% (G/G, 59.3%; A/A, 4.6%) |
| ORF, exon 65 (9053) | rs3025806 | A/T 0% (C/C, 100%) | A/T 0% (C/C, 100%) |
| ORF, exon 65 (9175) | exon 65 (new) | G/A, 2.3% (G/G, 97.7%) | G/A, 0% (G/G, 100%) |
| ORF, exon 67 (9523) | rs362308 | T/C, 0% (T/T, 100%) | T/C, 0% (T/T, 100%) |
| 3′ UTR, exon 67 (9633)[a] | rs362307 | C/T, 13.0% (C/C, 87.0%) | C/T, 48.6% (C/C, 49.5%; T/T 1.9% |
| 3′ UTR, exon 67 (9888) | rs362306 | G/A, 36.0% (G/G, 52.6%; A/A, 11.4%) | G/A, 35.8% (G/G, 59.6%; A/A, 4.6%) |
| 3′ UTR, exon 67 (9936) | rs362268 | C/G, 36.8% (C/C, 50.0%; G/G 13.2%) | C/G, 35.8% (C/C, 59.6%; G/G 4.6% |
| 3′ UTR, exon 67 (9948) | rs362305 | C/G, 20.2% (C/C, 78.1%; G/G 1.8%) | C/G, 11.9% (C/C, 85.3%; G/G 2.8%) |
| 3′ UTR, exon 67 (10060) | rs362304 | C/A, 22.8% (C/C, 73.7%; A/A, 3.5%) | C/A, 11.9% (C/C, 85.3%; AA, 2.8%) |
| 3′ UTR, exon 67 (10095) | rs362303 | C/T, 18.4% (C/C, 79.8%; T/T, 1.8%) | C/A, 11.9% (C/C, 85.3%; T/T, 2.8%) |
| 3′ UTR, exon 67 (10704) | rs1557210 | C/T, 0% (C/C 100%) | C/T, 0% (C/C 100%) |
| 3′ UTR, exon 67 (10708) | rs362302 | C/T, 4.3% (C/C, 95.7%) | C/T, 0% (C/C, 100%) |
| 3′ UTR, exon 67 (10796) | rs3025805 | G/T, 0% (G/G 100%) | G/T, 0% (G/G 100%) |
| 3′ UTR, exon 67 (11006) | rs362267 | C/T, 36.2% (C/C, 52.6%; T/T, 11.2%) | C/T, 35.5% (C/C, 59.8%; T/T, 4.7%) |

The SNP sites for which we tested siRNAs are in bold; the SNP associated with HD is shaded.
[a]These siRNAs provide good discrimination at the HD-associated SNP site.

TABLE 2

Combinations of three SNP sites and their frequency

| SNP1 | Genotype | SNP2 | Genotype | SNP3 | Genotype | Frequency |
|---|---|---|---|---|---|---|
| rs362307 | C/T | rs363125 | A/C | rs362273 | G/A | 75.23% |
| rs362307 | C/T | rs4690077 | A/G | rs362305 | C/G | 74.31% |
| rs362307 | C/T | rs4690077 | A/G | rs362304 | C/A | 74.31% |
| rs362307 | C/T | rs4690077 | A/G | rs362303 | C/T | 74.31% |
| rs362307 | C/T | rs363125 | A/C | rs4690074 | C/T | 74.31% |
| rs362307 | C/T | rs363125 | A/C | rs4690077 | A/G | 74.31% |
| rs362307 | C/T | rs363125 | A/C | rs362306 | G/A | 74.31% |
| rs362307 | C/T | rs363125 | A/C | rs362272 | G/A | 74.31% |
| rs362307 | C/T | rs363125 | A/C | rs362268 | C/G | 74.31% |
| rs362307 | C/T | rs362305 | C/G | rs362273 | G/A | 74.31% |
| rs362307 | C/T | rs362304 | C/A | rs362273 | G/A | 74.31% |
| rs362307 | C/T | rs362303 | C/T | rs362273 | G/A | 74.31% |
| rs362307 | C/T | rs362305 | C/G | rs4690074 | C/T | 73.39% |

TABLE 2-continued

Combinations of three SNP sites and their frequency

| SNP1 | Genotype | SNP2 | Genotype | SNP3 | Genotype | Frequency |
|---|---|---|---|---|---|---|
| rs362307 | C/T | rs362304 | C/A | rs4690074 | C/T | 73.39% |
| rs362307 | C/T | rs362306 | G/A | rs362305 | C/G | 73.39% |
| rs362307 | C/T | rs362306 | G/A | rs362304 | C/A | 73.39% |
| rs362307 | C/T | rs362306 | G/A | rs362303 | C/T | 73.39% |
| rs362307 | C/T | rs362305 | C/G | rs362272 | G/A | 73.39% |
| rs362307 | C/T | rs362304 | C/A | rs362272 | G/A | 73.39% |
| rs362307 | C/T | rs362303 | C/T | rs4690074 | C/T | 73.39% |
| rs362307 | C/T | rs362303 | C/T | rs362272 | G/A | 73.39% |
| rs362307 | C/T | rs362268 | C/G | rs362305 | C/G | 73.39% |
| rs362307 | C/T | rs362268 | C/G | rs362304 | C/A | 73.39% |
| rs362307 | C/T | rs362268 | C/G | rs362303 | C/T | 73.39% |
| rs362307 | C/T | rs363125 | A/C | rs362331 | C/T | 73.39% |
| rs362307 | C/T | rs363125 | A/C | rs362267 | C/T | 73.39% |
| rs362307 | C/T | rs362331 | C/T | rs362305 | C/G | 73.39% |
| rs362307 | C/T | rs362331 | C/T | rs362304 | C/A | 73.39% |
| rs362307 | C/T | rs362331 | C/T | rs362273 | G/A | 73.39% |
| rs362307 | C/T | rs4690077 | A/G | rs17781557 | T/G | 72.48% |
| rs362307 | C/T | rs362305 | C/G | rs362267 | C/T | 72.48% |
| rs362307 | C/T | rs362304 | C/A | rs362267 | C/T | 72.48% |
| rs362307 | C/T | rs362303 | C/T | rs362267 | C/T | 72.48% |
| rs362307 | C/T | rs362331 | C/T | rs4690074 | C/T | 72.48% |
| rs362307 | C/T | rs362331 | C/T | rs362306 | G/A | 72.48% |
| rs362307 | C/T | rs362331 | C/T | rs362303 | C/T | 72.48% |
| rs362307 | C/T | rs362331 | C/T | rs362272 | G/A | 72.48% |
| rs362307 | C/T | rs362331 | C/T | rs362267 | C/T | 72.48% |
| rs362307 | C/T | rs17781557 | T/G | rs362273 | G/A | 72.48% |
| rs362307 | C/T | rs362268 | C/G | rs17781557 | T/G | 71.56% |
| rs362307 | C/T | rs17781557 | T/G | rs4690074 | C/T | 71.56% |
| rs362307 | C/T | rs17781557 | T/G | rs362306 | G/A | 71.56% |
| rs362307 | C/T | rs17781557 | T/G | rs362272 | G/A | 71.56% |
| rs362307 | C/T | rs4690077 | A/G | rs.363075 | G/A | 70.64% |
| rs362307 | C/T | rs4690077 | A/G | Exon25 | G/A | 70.64% |
| rs362307 | C/T | rs17781557 | T/G | rs362267 | C/T | 70.64% |
| rs362307 | C/T | rs4690077 | A/G | rs362273 | G/A | 70.64% |
| rs362307 | C/T | rs.363075 | G/A | rs362273 | G/A | 70.64% |
| rs362307 | C/T | Exon25 | G/A | rs362273 | G/A | 70.64% |

II. Anti-htt RNA Silencing Agents

RNA silencing refers to a group of sequence-specific regulatory mechanisms (e.g. RNA interference (RNAi), transcriptional gene silencing (TGS), post-transriptional gene silencing (PTGS), quelling, co-suppression, and translational repression) mediated by RNA silencing agents which result in repression or "silencing" of a corresponding protein-coding gene. RNA silencing has been observed in many types of eurkayotes, including humans, and utility of RNA silencing agents as both therapeutics and research tools is the subject of intense interest.

Several types of small (~19-23 nt), noncoding RNAs trigger RNA silencing in eukaryotes, including small interfering RNAs (siRNAs) and microRNAs (miRNAs, also known as small temporal RNAs (stRNAs)). Recent evidence suggests that the two classes of small RNAs are functionally interchangeable, with the choice of RNA silencing mechanism (e.g. RNAi-mediated mRNA cleavage or translational repression) determined largely by the degree of complementarity between the small RNA and its target (Schwarz and Zamore, 2002; Hutvágner and Zamore, 2002; Zeng et al., 2003; Doench et al., 2003). RNA silencing agents with a high degree of complementarity to a corresponding target mRNA have been shown to direct its silencing by the cleavage-based mechanism (Zamore et al., 2000; Elbashir et al., 2001a; Rhoades et al., 2002; Reinhart et al., 2002; Llave et al., 2002a; Llave et al., 2002b; Xie et al., 2003; Kasschau et al., 2003; Tang et al., 2003; Chen, 2003). RNA silencing agents with a lower degree of complementarity mediate gene silencing by recruiting the RISC complex to the target mRNA, thereby blocking its translation but leaving the mRNA intact (Mourelatos et al., 2002; Hutvágner and Zamore, 2002; Caudy et al., 2002; Martinez et al., 2002; Abrahante et al., 2003; Brennecke et al., 2003; Lin et al., 2003; Xu et al., 2003).

RNA silencing agents have received particular interest as research tools and therapeutic agents for their ability to knock down expression of a particular protein with a high degree of sequence specificity. The sequence specificity of RNA silencing agents is particularly useful for allele-specific silencing of dominant, gain-of-function gene mutations. Diseases caused by dominant, gain-of-function gene mutations develop in heterozygotes bearing one mutant and one wild type copy of the gene. Some of the best-known diseases of this class are common neurodegenerative diseases, including Alzheimer's disease, Parkinson's disease and amyotrophic lateral sclerosis (ALS; "Lou Gehrig's disease") (Taylor et al., 2002). In these diseases, the exact pathways whereby the mutant proteins cause cell degeneration are not clear, but the origin of the cellular toxicity is known to be the mutant protein.

One group of inherited gain-of-function disorders are known as the trinucleotide repeat diseases. The common genetic mutation among these diseases is an increase in a series of a particular trinucleotide repeat. To date, the most frequent trinucleotide repeat is CAG, which codes for the amino acid glutamine. At least 9 CAG repeat diseases are known and there are more than 20 varieties of these diseases, including Huntington's disease, Kennedy's disease and many spinocerebellar diseases. These disorders share a neurodegenerative component in the brain and/or spinal cord. Each disease has a specific pattern of neurodegeneration in the brain and most have an autosomal dominant inheritance. The onset of the diseases generally occurs at 30 to 40 years of age, but in Huntington's disease CAG repeats in the huntingtin gene of >60 portend a juvenile onset. Research has shown that the genetic mutation (increase in length of CAG repeats from normal <36 in the huntingtin gene to >36 in disease) is associated with the synthesis of a mutant huntingtin protein, which has >36 polyglutamines (Aronin et al., 1995). It has also been shown that the protein forms cytoplasmic aggregates and nuclear inclusions (Difiglia et al., 1997) and associates with vesicles (Aronin et al., 1999). The precise pathogenic pathways are not known.

In the search for an effective treatment for these diseases, researchers in this field emphasized understanding the pathogenesis of the disease and initially sought to intercede at the level of the presumed aberrant protein interactions. However, there is no approved treatment for Huntington's disease or other trinucleotide repeat diseases. Accordingly, therapeutic RNA silencing agents capable of silencing Huntingtin proteins are of considerable interest.

In various embodiments, the present invention features anti-huntingtin RNA silencing agents (e.g., siRNA, shRNAs, miRNA), methods of making said RNA silencing agents, and methods (e.g., research and/or therapeutic methods) for using said improved RNA silencing agents (or portions thereof) for RNA silencing of mutant huntingtin protein. The RNA silencing agents comprise an antisense strand (or portions thereof), wherein the antisense strand has sufficient complementary to a heterozygous single nucleotide polymorphism to mediate an RNA-mediated silencing mechanism (e.g. RNAi). Allele-specific silencing can also be achieved by the use of DNA oligomers.

a) Design of Anti-htt siRNA Molecules

An siRNA molecule of the invention is a duplex consisting of a sense strand and complementary antisense strand, the antisense strand having sufficient complementary to a htt mRNA to mediate RNAi. Preferably, the siRNA molecule has a length from about 10-50 or more nucleotides, i.e., each strand comprises 10-50 nucleotides (or nucleotide analogs). More preferably, the siRNA molecule has a length from about 16-30, e.g., 16, 17, 18, 19, 20, 21, 22, 23, 24, 25, 26, 27, 28, 29, or 30 nucleotides in each strand, wherein one of the strands is sufficiently complementary to a target region. Preferably, the strands are aligned such that there are at least 1, 2, or 3 bases at the end of the strands which do not align (i.e., for which no complementary bases occur in the opposing strand) such that an overhang of 1, 2 or 3 residues occurs at one or both ends of the duplex when strands are annealed. Preferably, the siRNA molecule has a length from about 10-50 or more nucleotides, i.e., each strand comprises 10-50 nucleotides (or nucleotide analogs). More preferably, the siRNA molecule has a length from about 16-30, e.g., 16, 17, 18, 19, 20, 21, 22, 23, 24, 25, 26, 27, 28, 29, or 30 nucleotides in each strand, wherein one of the strands is substantially complementary to a target region e.g., a gain-of-function gene target region, and the other strand is identical or substantially identical to the first strand.

Generally, siRNAs can be designed by using any method known in the art, for instance, by using the following protocol:

1. The siRNA should be specific for a heterozygous single-nucleotide polymorphism (SNP) found in a mutant huntingtin (htt) allele, but not a wild-type huntingtin allele. The first strand should be complementary to this sequence, and the other strand is substantially complementary to the first strand. In one embodiment, the SNP is outside the expanded CAG repeat of the mutant huntingin (htt) allele. In another embodiment, the SNP is outside a coding region of the target gene. Exemplary polymorphisms are selected from the 5' untranslated region (5'-UTR) of a target gene. Cleavage of mRNA at these sites should eliminate translation of corresponding mutant protein. Polymorphisms from other regions of the mutant gene are also suitable for targeting. A sense strand is designed based on the sequence of the selected portion. Further, siRNAs with lower G/C content (35-55%) may be more active than those with G/C content higher than 55%. Thus in one embodiment, the invention includes nucleic acid molecules having 35-55% G/C content.

2. The sense strand of the siRNA is designed based on the sequence of the selected target site. Preferably the sense strand includes about 19 to 25 nucleotides, e.g., 19, 20, 21, 22, 23, 24 or 25 nucleotides. More preferably, the sense strand includes 21, 22 or 23 nucleotides. The skilled artisan will appreciate, however, that siRNAs having a length of less than 19 nucleotides or greater than 25 nucleotides can also function to mediate RNAi. Accordingly, siRNAs of such length are also within the scope of the instant invention provided that they retain the ability to mediate RNAi. Longer RNA silencing agents have been demonstrated to ellicit an interferon or PKR response in certain mammalian cells which may be undesirable. Preferably the RNA silencing agents of the invention do not ellicit a PKR response (i.e., are of a sufficiently short length). However, longer RNA silencing agents may be useful, for example, in cell types incapable of generating a PRK response or in situations where the PKR response has been downregulated or dampened by alternative means.

Generally, siRNA molecules have sufficient complementarity with the target site such that the siRNA can mediate RNAi. In general, siRNA containing nucleotide sequences sufficiently identical to a portion of the target gene to effect RISC-mediated cleavage of the target gene are preferred. Accordingly, in a preferred embodiment, the sense strand of the siRNA is designed have to have a sequence sufficiently identical to a portion of the target. For example, the sense strand may have 100% identity to the target site. However, 100% identity is not required. Greater than 80% identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% identity, between the sense strand and the target RNA sequence is preferred. The invention has the advantage of being able to tolerate certain sequence variations to enhance efficiency and specificity of RNAi. In one embodiment, the sense strand has 4, 3, 2, 1, or 0 mismatched nucleotide(s) with a target region, such as a target region that differs by at least one base pair between the wild type and mutant allele, e.g., a target region comprising the gain-of-function mutation, and the other strand is identical or substantially identical to the first strand. Moreover, siRNA sequences with small insertions or deletions of 1 or 2 nucleotides may also be effective for mediating RNAi. Alternatively, siRNA sequences with nucleotide analog substitutions or insertions can be effective for inhibition.

Sequence identity may determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=# of identical positions/total # of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) *Proc. Natl. Acad. Sci. USA* 87:2264-68, modified as in Karlin and Altschul (1993) *Proc. Natl. Acad. Sci. USA* 90:5873-77. Such an algorithm is incorporated into the BLAST programs (version 2.0) of Altschul, et al. (1990) *J. Mol. Biol.* 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) *Nucleic Acids Res.* 25(17):3389-3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, *CABIOS* (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

3. siRNAs are designed such that perfect complementarity exists between the siRNA and the target mRNA (e.g., the mutant mRNA) at the polymorphism (e.g., the point mutation), there thus being a mismatch if the siRNA is compared (e.g., aligned) to the reference sequence (e.g., wild type allele or mRNA sequence). Such perfect complementarity exists, at least, at or around the cleavage site, although discrimination-enhancing mismatches may be introduced, for example, in the seed sequence as described herein. Other efficiency enhancing mismatches can be included, for example, at the termini, as described herein. The sense strand sequence may be designed such that the polymorphism is essentially in the middle of the strand. For example, if a 21-nucleotide siRNA is chosen, the polymorphism is at, for example, nucleotide 6, 7, 8, 9, 10, 11, 12, 13, 14, 15 or 16 (i.e., 6, 7, 8, 9, 10, 11, 12, 13, 14, 15 or 16 nucleotides from the 5' end of the sense strand. For a 22-nucleotide siRNA, the polymorphism is at, for example, nucleotide 7, 8, 9, 10, 11, 12, 13, 14, 15 or 16. For a 23-nucleotide siRNA, the polymorphism is at, for example, 7, 8, 9, 10, 11, 12, 13, 14, 15 or 16. For a 24-nucleotide siRNA, the polymorphism is at, for example, 9, 10, 11, 12, 13, 14 or 16. For a 25-nucleotide siRNA, the polymorphism is at, for example, 9, 10, 11, 12, 13, 14, 15, 16 or 17.

In one preferred embodiment, the sense strand of the siRNA is identical to the polymorphism at a nucleotide position that is 10 nucleotides from the 5' end of the sense strand (i.e., position P10).

In another preferred embodiment, the sense strand of the siRNA is identical to the polymorphism at a nucleotide position that is 16 nucleotides from the 5' end of the sense strand (i.e., position P16).

4. siRNAs with single nucleotide specificity are preferably designed such that base paring at the single nucleotide in the corresponding reference (e.g., wild type) sequence is disfavored. For example, designing the siRNA such that purine:purine paring exists between the siRNA and the wild type mRNA at the single nucleotide enhances single nucleotide specificity. The purine:purine paring is selected, for example, from the group G:G, A:G, G:A and A:A pairing where necessary modifications elsewhere in the siRNA can compensate for any lack of the desired purine:purine mismatch. Moreover, purine pyrimidine pairing between the siRNA and the mutant mRNA at the single nucleotide enhances single nucleotide specificity. The purine:pyrimidine paring is selected, for example, from the group G:C, C:G, A:U, U:A, C:A, A:C, U:A and A:U pairing.

5. The antisense or guide strand of the siRNA is routinely the same length as the sense strand and includes complementary nucleotides. In one embodiment, the guide and sense strands are fully complementary, i.e., the strands are blunt-ended when aligned or annealed. In another embodiment, the strands of the siRNA can be paired in such a way as to have a 3' overhang of 1 to 4, e.g., 2, nucleotides. Overhangs can comprise (or consist of) nucleotides corresponding to the target gene sequence (or complement thereof). Alternatively, overhangs can comprise (or consist of) deoxyribonucleotides, for example dTs, or nucleotide analogs, or other suitable non-nucleotide material. Thus in another embodiment, the nucleic acid molecules may have a 3' overhang of 2 nucleotides, such as TT. The overhanging nucleotides may be either RNA or DNA. As noted above, it is desirable to choose a target region wherein the mutant:wild type mismatch is a purine:purine mismatch.

6. Using any method known in the art, compare the potential targets to the appropriate genome database (human, mouse, rat, etc.) and eliminate from consideration any target sequences with significant homology to other coding sequences. One such method for such sequence homology searches is known as BLAST, which is available at National Center for Biotechnology Information website.

7. Select one or more sequences that meet your criteria for evaluation.

Further general information about the design and use of siRNA may be found in "The siRNA User Guide," available at The Max-Plank-Institut fër Biophysikalishe Chemie website.

Alternatively, the siRNA may be defined functionally as a nucleotide sequence (or oligonucleotide sequence) that is capable of hybridizing with the target sequence (e.g., 400 mM NaCl, 40 mM PIPES pH 6.4, 1 mM EDTA, 50° C. or 70° C. hybridization for 12-16 hours; followed by washing). Additional preferred hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6(log 10[Na+])+0.41(% G+C)—(600/N), where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, *Molecular Cloning: A Laboratory Manual*, Cold Spring Harbor Laboratory Press, Cold Spring Harbor, N.Y., chapters 9 and 11, and *Current Protocols in Molecular Biology*, 1995, F. M. Ausubel et al., eds., John Wiley & Sons, Inc., sections 2.10 and 6.3-6.4, incorporated herein by reference.

Negative control siRNAs should have the same nucleotide composition as the selected siRNA, but without significant sequence complementarity to the appropriate genome. Such negative controls may be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence.

8. To validate the effectiveness by which siRNAs destroy mutant mRNAs (e.g., mutant huntingtin mRNA), the siRNA may be incubated with mutant cDNA (e.g., mutant huntingtin cDNA) in a *Drosophila*-based in vitro mRNA expression system. Radiolabeled with $^{32}P$, newly synthesized mutant mRNAs (e.g., mutant huntingtin mRNA) are detected autoradiographically on an agarose gel. The presence of cleaved mutant mRNA indicates mRNA nuclease activity. Suitable controls include omission of siRNA and use of wild-type huntingtin cDNA. Alternatively, control siRNAs are selected having the same nucleotide composition as the selected siRNA, but without significant sequence complementarity to the appropriate target gene. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence.

b) siRNA-Like Molecules siRNA-like molecules of the invention have a sequence (i.e., have a strand having a sequence) that is sufficiently complementary to a heterozygous SNP of a htt mRNA to direct gene silencing either by RNAi or translational repression. siRNA-like molecules are designed in the same way as siRNA molecules, but the degree of sequence identity between the sense strand and target RNA approximates that observed between an miRNA and its target. In general, as the degree of sequence identity between a miRNA sequence and the corresponding target gene sequence is decreased, the tendency to mediate post-transcriptional gene silencing by translational repression rather than RNAi is increased. Therefore, in an alternative embodiment, where post-transcriptional gene silencing by translational repression of the target gene is desired, the miRNA sequence has partial complementarity with the target gene sequence. In certain embodiments, the miRNA sequence has partial complementarity with one or more short sequences (complementarity sites) dispersed within the target mRNA (e.g. within the 3'-UTR of the target mRNA) (Hutvagner and Zamore, Science, 2002; Zeng et al., Mol. Cell, 2002; Zeng et al., RNA, 2003; Doench et al., Genes & Dev., 2003). Since the mechanism of translational repression is cooperative, multiple complementarity sites (e.g., 2, 3, 4, 5, or 6) may be targeted in certain embodiments.

The capacity of a siRNA-like duplex to mediate RNAi or translational repression may be predicted by the distribution of non-identical nucleotides between the target gene sequence and the nucleotide sequence of the silencing agent at the site of complementarity. In one embodiment, where gene silencing by translational repression is desired, at least one non-identical nucleotide is present in the central portion of the complementarity site so that duplex formed by the miRNA guide strand and the target mRNA contains a central "bulge" (Doench J G et al., Genes & Dev., 2003). In another embodiment 2, 3, 4, 5, or 6 contiguous or non-contiguous non-identical nucleotides are introduced. The non-identical nucleotide may be selected such that it forms a wobble base pair (e.g., G:U) or a mismatched base pair (G:A, C:A, C:U, G:G, A:A, C:C, U:U). In a further preferred embodiment, the "bulge" is centered at nucleotide positions 12 and 13 from the 5' end of the miRNA molecule.

c) Short Hairpin RNA (shRNA) Molecules

In certain embodiments, the instant invention provides shRNAs capable of mediating RNA silencing of a heterozygous htt SNP with enhanced selectivity. In contrast to siRNAs, shRNAs mimic the natural precursors of micro RNAs (miRNAs) and enter at the top of the gene silencing pathway. For this reason, shRNAs are believed to mediate gene silencing more efficiently by being fed through the entire natural gene silencing pathway.

miRNAs are noncoding RNAs of approximately 22 nucleotides which can regulate gene expression at the post transcriptional or translational level during plant and animal development. One common feature of miRNAs is that they are all excised from an approximately 70 nucleotide precursor RNA stem-loop termed pre-miRNA, probably by Dicer, an RNase III-type enzyme, or a homolog thereof. Naturally-occurring miRNA precursors (pre-miRNA) have a single strand that forms a duplex stem including two portions that are generally complementary, and a loop, that connects the two portions of the stem. In typical pre-miRNAs, the stem includes one or more bulges, e.g., extra nucleotides that create a single nucleotide "loop" in one portion of the stem, and/or one or more unpaired nucleotides that create a gap in the hybridization of the two portions of the stem to each other. Short hairpin RNAs, or engineered RNA precursors, of the invention are artificial constructs based on these naturally occurring pre-miRNAs, but which are engineered to deliver desired RNA silencing agents (e.g., siRNAs of the invention). By substituting the stem sequences of the pre-miRNA with sequence complementary to the target mRNA, a shRNA is formed. The shRNA is processed by the entire gene silencing pathway of the cell, thereby efficiently mediating RNAi.

The requisite elements of a shRNA molecule include a first portion and a second portion, having sufficient complementarity to anneal or hybridize to form a duplex or double-stranded stem portion. The two portions need not be fully or perfectly complementary. The first and second "stem" portions are connected by a portion having a sequence that has insufficient sequence complementarity to anneal or hybridize to other portions of the shRNA. This latter portion is referred to as a "loop" portion in the shRNA molecule. The shRNA molecules are processed to generate siRNAs. shRNAs can also include one or more bulges, i.e., extra nucleotides that create a small nucleotide "loop" in a portion of the stem, for example a one-, two- or three-nucleotide loop. The stem portions can be the same length, or one portion can include an overhang of, for example, 1-5 nucleotides. The overhanging nucleotides can include, for example, uracils (Us), e.g., all Us. Such Us are notably encoded by thymidines (Ts) in the shRNA-encoding DNA which signal the termination of transcription.

In shRNAs, or engineered precursor RNAs, of the instant invention, one portion of the duplex stem is a nucleic acid sequence that is complementary (or anti-sense) to the heterozygous SNP. Preferably, one strand of the stem portion of the shRNA is sufficiently complementary (e.g., antisense) to a target RNA (e.g., mRNA) sequence to mediate degradation or cleavage of said target RNA via RNA interference (RNAi). Thus, engineered RNA precursors include a duplex stem with two portions and a loop connecting the two stem portions. The antisense portion can be on the 5' or 3' end of the stem. The stem portions of a shRNA are preferably about 15 to about 50 nucleotides in length. Preferably the two stem portions are about 18 or 19 to about 21, 22, 23, 24, 25, 30, 35, 37, 38, 39, or 40 or more nucleotides in length. In preferred embodiments, the length of the stem portions should be 21 nucleotides or greater. When used in mammalian cells, the length of the stem portions should be less than about 30 nucleotides to avoid provoking non-specific responses like the interferon pathway. In non-mammalian cells, the stem can be longer than 30 nucleotides. In fact, the stem can include much larger sections complementary to the target mRNA (up to, and including the entire mRNA). In fact, a stem portion can include much larger sections complementary to the target mRNA (up to, and including the entire mRNA).

The two portions of the duplex stem must be sufficiently complementary to hybridize to form the duplex stem. Thus, the two portions can be, but need not be, fully or perfectly complementary. In addition, the two stem portions can be the same length, or one portion can include an overhang of 1, 2, 3, or 4 nucleotides. The overhanging nucleotides can include, for example, uracils (Us), e.g., all Us. The loop in the shRNAs or engineered RNA precursors may differ from natural pre-miRNA sequences by modifying the loop sequence to increase or decrease the number of paired nucleotides, or replacing all or part of the loop sequence with a tetraloop or other loop sequences. Thus, the loop in the shRNAs or engineered RNA precursors can be 2, 3, 4, 5, 6, 7, 8, 9, or more, e.g., 15 or 20, or more nucleotides in length.

The loop in the shRNAs or engineered RNA precursors may differ from natural pre-miRNA sequences by modifying the loop sequence to increase or decrease the number of paired nucleotides, or replacing all or part of the loop sequence with a tetraloop or other loop sequences. Thus, the loop portion in the shRNA can be about 2 to about 20 nucleotides in length, i.e., about 2, 3, 4, 5, 6, 7, 8, 9, or more, e.g., 15 or 20, or more nucleotides in length. A preferred loop consists of or comprises a "tetraloop" sequences. Exemplary tetraloop sequences include, but are not limited to, the sequences GNRA, where N is any nucleotide and R is a purine nucleotide, GGGG, and UUUU.

In certain embodiments, shRNAs of the invention include the sequences of a desired siRNA molecule described supra. In other embodiments, the sequence of the antisense portion of a shRNA can be designed essentially as described above or generally by selecting an 18, 19, 20, 21 nucleotide, or longer, sequence from within the target RNA (e.g., SOD1 or htt mRNA), for example, from a region 100 to 200 or 300 nucleotides upstream or downstream of the start of translation. In general, the sequence can be selected from any portion of the target RNA (e.g., mRNA) including the 5' UTR (untranslated region), coding sequence, or 3' UTR, provided said portion is distant from the site of the gain-of-function muation. This sequence can optionally follow immediately after a region of the target gene containing two adjacent AA nucleotides. The last two nucleotides of the nucleotide sequence can be selected to be UU. This 21 or so nucleotide sequence is used to create one portion of a duplex stem in the shRNA. This sequence can replace a stem portion of a wild-type pre-miRNA sequence, e.g., enzymatically, or is included in a complete sequence that is synthesized. For example, one can synthesize DNA oligonucleotides that encode the entire stem-loop engineered RNA precursor, or that encode just the portion to be inserted into the duplex stem of the precursor, and using restriction enzymes to build the engineered RNA precursor construct, e.g., from a wild-type pre-miRNA.

Engineered RNA precursors include in the duplex stem the 21-22 or so nucleotide sequences of the siRNA or siRNA-like duplex desired to be produced in vivo. Thus, the stem portion of the engineered RNA precursor includes at least 18 or 19 nucleotide pairs corresponding to the sequence of an exonic portion of the gene whose expression is to be reduced or inhibited. The two 3' nucleotides flanking this region of the stem are chosen so as to maximize the production of the siRNA from the engineered RNA precursor and to maximize the efficacy of the resulting siRNA in targeting the corresponding mRNA for translational repression or destruction by RNAi in vivo and in vitro.

In certain embodiments, shRNAs of the invention include miRNA sequences, optionally end-modified miRNA sequences, to enhance entry into RISC. The miRNA sequence can be similar or identical to that of any naturally occurring miRNA (see e.g. *The miRNA Registry; Griffiths-Jones S, Nuc. Acids Res.,* 2004). Over one thousand natural miRNAs have been identified to date and together they are thought to comprise ~1% of all predicted genes in the genome. Many natural miRNAs are clustered together in the introns of pre-mRNAs and can be identified in silico using homology-based searches (Pasquinelli et al., 2000; Lagos-Quintana et al., 2001; Lau et al., 2001; Lee and Ambros, 2001) or computer algorithms (e.g. MiRScan, MiRSeeker) that predict the capability of a candidate miRNA gene to form the stem loop structure of a pri-mRNA (Grad et al., Mol. Cell., 2003; Lim et al., Genes Dev., 2003; Lim et al., Science, 2003; Lai E C et al., Genome Bio., 2003). An online registry provides a searchable database of all published miRNA sequences (*The miRNA Registry at the Sanger Institute website; Griffiths-Jones S, Nuc. Acids Res.,* 2004). Exemplary, natural miRNAs include lin-4, let-7, miR-10, mirR-15, miR-16, miR-168, miR-175, miR-196 and their homologs, as well as other natural miRNAs from humans and certain model organisms including *Drosophila melanogaster, Caenorhabditis elegans*, zebrafish, *Arabidopsis thalania*, mouse, and rat as described in International PCT Publication No. WO 03/029459.

Naturally-occurring miRNAs are expressed by endogenous genes in vivo and are processed from a hairpin or stem-loop precursor (pre-miRNA or pri-miRNAs) by Dicer or other RNAses (Lagos-Quintana et al., Science, 2001; Lau et al., Science, 2001; Lee and Ambros, Science, 2001; Lagos-Quintana et al., Curr. Biol., 2002; Mourelatos et al., Genes Dev., 2002; Reinhart et al., Science, 2002; Ambros et al., Curr. Biol., 2003; Brennecke et al., 2003; Lagos-Quintana et al., RNA, 2003; Lim et al., Genes Dev., 2003; Lim et al., Science, 2003). miRNAs can exist transiently in vivo as a double-stranded duplex but only one strand is taken up by the RISC complex to direct gene silencing. Certain miRNAs, e.g. plant miRNAs, have perfect or near-perfect complementarity to their target mRNAs and, hence, direct cleavage of the target mRNAs. Other miRNAs have less than perfect complementarity to their target mRNAs and, hence, direct translational repression of the target mRNAs. The degree of complementarity between an miRNA and its target mRNA is believed to determine its mechanism of action. For example, perfect or near-perfect complementarity between a miRNA and its target mRNA is predictive of a cleavage mechanism (Yekta et al., *Science,* 2004), whereas less than perfect complementarity is predictive of a translational repression mechanism. In particular embodiments, the miRNA sequence is that of a naturally-occurring miRNA sequence, the aberrant expression or activity of which is correlated with a miRNA disorder.

d) Dual Functional Oligonucleotide Tethers

In other embodiments, the RNA silencing agents of the present invention include dual functional oligonucleotide tethers useful for the intercellular recruitment of a miRNA. Animal cells express a range of miRNAs, noncoding RNAs of approximately 22 nucleotides which can regulate gene expression at the post transcriptional or translational level. By binding a miRNA bound to RISC and recruiting it to a target mRNA, a dual functional oligonucleotide tether can repress the expression of genes involved e.g., in the arteriosclerotic process. The use of oligonucleotide tethers offer several advantages over existing techniques to repress the expression of a particular gene. First, the methods described herein allow an endogenous molecule (often present in abundance), an miRNA, to mediate RNA silencing; accordingly the methods described herein obviate the need to introduce foreign molecules (e.g., siRNAs) to mediate RNA silencing. Second, the RNA-silencing agents and, in particular, the linking moiety (e.g., oligonucleotides such as the 2'-O-methyl oligonucleotide), can be made stable and resistant to nuclease activity. As a result, the tethers of the present invention can be designed for direct delivery, obviating the need for indirect delivery (e.g. viral) of a precursor molecule or plasmid designed to make the desired agent within the cell. Third, tethers and their respective moieties, can be designed to conform to specific mRNA sites and specific miRNAs. The designs can be cell and gene product specific. Fourth, the methods disclosed herein leave the mRNA intact, allowing one skilled in the art to block protein synthesis in short pulses using the cell's own machinery. As a result, these methods of RNA silencing are highly regulatable.

The dual functional oligonucleotide tethers ("tethers") of the invention are designed such that they recruit miRNAs (e.g., endogenous cellular miRNAs) to a target mRNA so as to induce the modulation of a gene of interest. In preferred embodiments, the tethers have the formula T-L-µ, wherein T is an mRNA targeting moiety, L is a linking moiety, and µ is an miRNA recruiting moiety. Any one or more moiety may be double stranded. Preferably, however, each moiety is single stranded.

Moieties within the tethers can be arranged or linked (in the 5' to 3' direction) as depicted in the formula T-L-µ (i.e., the 3' end of the targeting moiety linked to the 5' end of the linking moiety and the 3' end of the linking moiety linked to the 5' end of the miRNA recruiting moiety). Alternatively, the moieties can be arranged or linked in the tether as follows: µ-T-L (i.e., the 3' end of the miRNA recruiting moiety linked to the 5' end of the linking moiety and the 3' end of the linking moiety linked to the 5' end of the targeting moiety).

The mRNA targeting moiety, as described above, is capable of capturing a specific target mRNA. According to the invention, expression of the target mRNA is undesirable, and, thus, translational repression of the mRNA is desired. The mRNA targeting moiety should be of sufficient size to effectively bind the target mRNA. The length of the targeting moiety will vary greatly depending, in part, on the length of the target mRNA and the degree of complementarity between the target mRNA and the targeting moiety. In various embodiments, the targeting moiety is less than about 200, 100, 50, 30, 25, 20, 19, 18, 17, 16, 15, 14, 13, 12, 11, 10, 9, 8, 7, 6, or 5 nucleotides in length. In a particular embodiment, the targeting moiety is about 15 to about 25 nucleotides in length.

The miRNA recruiting moiety, as described above, is capable of associating with a miRNA. According to the invention, the miRNA may be any miRNA capable of repressing the target mRNA. Mammals are reported to have over 250 endogenous miRNAs (Lagos-Quintana et al. (2002) *Current Biol.* 12:735-739; Lagos-Quintana et al. (2001) *Science* 294: 858-862; and Lim et al. (2003) *Science* 299:1540). In various embodiments, the miRNA may be any art-recognized miRNA.

The linking moiety is any agent capable of linking the targeting moieties such that the activity of the targeting moieties is maintained. Linking moieties are preferably oligonucleotide moieties comprising a sufficient number of nucleotides such that the targeting agents can sufficiently interact with their respective targets. Linking moieties have little or no sequence homology with cellular mRNA or miRNA sequences. Exemplary linking moieties include one or more 2'-O-methylnucleotides, e.g., 2'-O-methyladenosine, 2'-O-methylthymidine, 2'-O-methylguanosine or 2'-O-methyluridine.

III. Modified Anti-htt RNA Silencing Agents

In certain aspects of the invention, an RNA silencing agent (or any portion thereof) of the invention as described supra may be modified such that the activity of the agent is further improved. For example, the RNA silencing agents described in Section II supra may be modified with any of the modifications described infra. The modifications can, in part, serve to further enhance target discrimination, to enhance stability of the agent (e.g., to prevent degradation), to promote cellular uptake, to enhance the target efficiency, to improve efficacy in binding (e.g., to the targets), to improve patient tolerance to the agent, and/or to reduce toxicity.

1) Modifications to Enhance Target Discrimination

In certain embodiments, the RNA silencing agents of the invention may be substituted with a destabilizing nucleotide to enhance single nucleotide target discrimination (see U.S. application Ser. No. 11/698,689, filed Jan. 25, 2007 and U.S. Provisional Application No. 60/762,225 filed Jan. 25, 2006, both of which are incorporated herein by reference). Such a modification may be sufficient to abolish the specificity of the RNA silencing agent for a non-target mRNA (e.g. wild-type mRNA), without appreciably affecting the specificity of the RNA silencing agent for a target mRNA (e.g. gain-of-function mutant mRNA).

In particular embodiments, the RNA silencing agents of the invention are modified by the introduction of at least one universal nucleotide in the antisense strand thereof. Universal nucleotides comprise base portions that are capable of base pairing indiscriminately with any of the four conventional nucleotide bases (e.g. A, G, C, U). A universal nucleotide is preferred because it has relatively minor effect on the stability of the RNA duplex or the duplex formed by the guide strand of the RNA silencing agent and the target mRNA. Exemplary universal nucleotide include those having an inosine base portion or an inosine analog base portion selected from the group consisting of deoxyinosine (e.g. 2'-deoxyinosine), 7-deaza-2'-deoxyinosine, 2'-aza-2'-deoxyinosine, PNA-inosine, morpholino-inosine, LNA-inosine, phosphoramidate-inosine, 2'-O-methoxyethyl-inosine, and 2'-OMe-inosine. In particularly preferred embodiments, the universal nucleotide is an inosine residue or a naturally occurring analong thereof.

The RNA silencing agents of the invention are preferably modified by the introduction of at least one destabilizing nucleotide within 5 nucleotides from a specificity-determining nucleotide (ie. the nucleotide which recognizes the disease-related polymorphism). For example, the destabilizing nucleotide may be introduced at a position that is within 5, 4, 3, 2, or 1 nucleotide(s) from a specificity-determining nucleotide. In exemplary embodiments, the destabilizing nucleotide is introduced at a position which is 3 nucleotides from the specificity-determining nucleotide (ie. such that there are 2 stabilizing nucleotides between the destablilizing nucleotide and the specificity-determining nucleotide). In RNA silencing agents having two strands or strand portions (e.g. siRNAs and shRNAs), the destabilizing nucleotide may be introduced in the strand or strand portion that does not contain the specificity-determining nucleotide. In preferred embodiments, the destabilizing nucleotide is introduced in the same strand or strand portion that contains the specificity-determining nucleotide.

The instant invention have further discovered that mismatches in the seed sequence of an siRNA, where combined with mismatches at the mutant or polymorphic nucleotide, can further enhance the discriminatory activity of such siRNAs (i.e., decreased cleavage of normal allele, as compared to mutant allele). Accordingly, parings mismatches at the specificity-determining nucleotide (e.g., P10 or P16) with a second mismatch in the seed sequence (numbered nucleotides 2-7 in the guide strand of, for example, a 21-nt siRNA) can enhance discrimination. A preferred combination of mismatches is, for example, at P10 and P5 within the guide strand.

2) Modifications to Enhance Efficacy and Specificity

In certain embodiments, the RNA silencing agents of the invention may be altered to facilitate enhanced efficacy and specificity in mediating RNAi according to asymmetry design rules (see International Publication No. WO 2005/001045, US Publication No. 2005-0181382 A1). Such alterations facilitate entry of the antisense strand of the siRNA (e.g., a siRNA designed using the methods of the invention or an siRNA produced from a shRNA) into RISC in favor of the sense strand, such that the antisense strand preferentially guides cleavage or translational repression of a target mRNA, and thus increasing or improving the efficiency of target cleavage and silencing. Preferably the aymmetry of an RNA silencing agent is enhanced by lessening the base pair strength between the antisense strand 5' end (AS 5') and the sense strand 3' end (S 3') of the RNA silencing agent relative to the bond strength or base pair strength between the antisense strand 3' end (AS 3') and the sense strand 5' end (S'5) of said RNA silencing agent.

In one embodiment, the asymmetry of an RNA silencing agent of the invention may be enhanced such that there are fewer G:C base pairs between the 5' end of the first or antisense strand and the 3' end of the sense strand portion than between the 3' end of the first or antisense strand and the 5' end of the sense strand portion. In another embodiment, the asymmetry of an RNA silencing agent of the invention may be enhanced such that there is at least one mismatched base pair between the 5' end of the first or antisense strand and the 3' end of the sense strand portion. Preferably, the mismatched base pair is selected from the group consisting of G:A, C:A, C:U, G:G, A:A, C:C and U:U. In another embodiment, the asymmetry of an RNA silencing agent of the invention may be enhanced such that there is at least one wobble base pair, e.g., G:U, between the 5' end of the first or antisense strand and the 3' end of the sense strand portion. In another embodiment, the asymmetry of an RNA silencing agent of the invention may be enhanced such that there is at least one base pair comprising a rare nucleotide, e.g., inosine (I). Preferably, the base pair is selected from the group consisting of an I:A, I:U and I:C. In yet another embodiment, the asymmetry of an RNA silencing agent of the invention may be enhanced such that there is at least one base pair comprising a modified nucleotide. In preferred embodiments, the modified nucleotide is selected from the group consisting of 2-amino-G, 2-amino-A, 2,6-diamino-G, and 2,6-diamino-A.

3) RNA Silencing Agents with Enhanced Stability

The RNA silencing agents of the present invention can be modified to improve stability in serum or in growth medium for cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect the efficiency of RNA interference.

In a preferred aspect, the invention features RNA silencing agents that include first and second strands wherein the second strand and/or first strand is modified by the substitution of internal nucleotides with modified nucleotides, such that in vivo stability is enhanced as compared to a corresponding unmodified RNA silencing agent. As defined herein, an "internal" nucleotide is one occurring at any position other than the 5' end or 3' end of nucleic acid molecule, polynucleotide or oligonucleoitde. An internal nucleotide can be within a single-stranded molecule or within a strand of a duplex or double-stranded molecule. In one embodiment, the sense strand and/or antisense strand is modified by the substitution of at least one internal nucleotide. In another embodiment, the sense strand and/or antisense strand is modified by the substitution of at least 2, 3, 4, 5, 6, 7, 8, 9, 10, 11, 12, 13, 14, 15, 16, 17, 18, 19, 20, 21, 22, 23, 24, 25 or more internal nucleotides. In another embodiment, the sense strand and/or antisense strand is modified by the substitution of at least 5%, 10%, 15%, 20%, 25%, 30%, 35%, 40%, 45%, 50%, 55%, 60%, 65%, 70%, 75%, 80%, 85%, 90%, 95% or more of the internal nucleotides. In yet another embodiment, the sense strand and/or antisense strand is modified by the substitution of all of the internal nucleotides.

In a preferred embodiment of the present invention the RNA silencing agents may contain at least one modified nucleotide analogue. The nucleotide analogues may be located at positions where the target-specific silencing activity, e.g., the RNAi mediating activity or translational repression activity is not substantially effected, e.g., in a region at the 5'-end and/or the 3'-end of the siRNA molecule. Particularly, the ends may be stabilized by incorporating modified nucleotide analogues.

Preferred nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In preferred backbone-modified ribonucleotides the phosphoester group connecting to adjacent ribonucleotides is replaced by a modified group, e.g., of phosphothioate group. In preferred sugar-modified ribonucleotides, the 2' OH-group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

In particular embodiments, the modifications are 2'-fluoro, 2'-amino and/or 2'-thio modifications. Particularly preferred modifications include 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine, 2,6-diaminopurine, 4-thio-uridine, and/or 5-amino-allyl-uridine. In a particular embodiment, the 2'-fluoro ribonucleotides are every uridine and cytidine. Additional exemplary modifications include 5-bromo-uridine, 5-iodo-uridine, 5-methyl-cytidine, ribo-thymidine, 2-aminopurine, 2'-amino-butyryl-pyrene-uridine, 5-fluoro-cytidine, and 5-fluoro-uridine. 2'-deoxy-nucleotides and 2'-Ome nucleotides can also be used within modified RNA-silencing agents moities of the instant invention. Additional modified residues include, deoxy-abasic, inosine, N3-methyl-uridine, N6, N6-dimethyl-adenosine, pseudouridine, purine ribonucleoside and ribavirin. In a particularly preferred embodiment, the 2' moiety is a methyl group such that the linking moiety is a 2'-O-methyl oligonucleotide.

In an exemplary embodiment, the RNA silencing agent of the invention comprises Locked Nucleic Acids (LNAs). LNAs comprise sugar-modified nucleotides that resist nuclease activities (are highly stable) and possess single nucleotide discrimination for mRNA (Elmen et al., *Nucleic Acids Res.*, (2005), 33(1): 439-447; Braasch et al. (2003) *Biochemistry* 42:7967-7975, Petersen et al. (2003) *Trends Biotechnol* 21:74-81). These molecules have 2'-0,4'-C-ethylene-bridged nucleic acids, with possible modifications such as 2'-deoxy-2"-fluorouridine. Moreover, LNAs increase the specificity of oligonucleotides by constraining the sugar moiety into the 3'-endo conformation, thereby preorganizing the nucleotide for base pairing and increasing the melting temperature of the oligonucleotide by as much as 10° C. per base.

In another exemplary embodiment, the RNA silencing agent of the invention comprises Peptide Nucleic Acids (PNAs). PNAs comprise modified nucleotides in which the sugar-phosphate portion of the nucleotide is replaced with a neutral 2-amino ethylglycine moiety capable of forming a polyamide backbone which is highly resistant to nuclease digestion and imparts improved binding specificity to the molecule (Nielsen, et al., *Science*, (2001), 254: 1497-1500).

Also preferred are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

In other embodiments, cross-linking can be employed to alter the pharmacokinetics of the RNA silencing agent, for example, to increase half-life in the body. Thus, the invention includes RNA silencing agents having two complementary strands of nucleic acid, wherein the two strands are crosslinked. The invention also includes RNA silencing agents which are conjugated or unconjugated (e.g., at its 3' terminus) to another moiety (e.g. a non-nucleic acid moiety such as a peptide), an organic compound (e.g., a dye), or the like). Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

Other exemplary modifications include: (a) 2' modification, e.g., provision of a 2' OMe moiety on a U in a sense or antisense strand, but especially on a sense strand, or provision of a 2' OMe moiety in a 3' overhang, e.g., at the 3' terminus (3' terminus means at the 3' atom of the molecule or at the most 3' moiety, e.g., the most 3' P or 2' position, as indicated by the context); (b) modification of the backbone, e.g., with the replacement of an O with an S, in the phosphate backbone, e.g., the provision of a phosphorothioate modification, on the U or the A or both, especially on an antisense strand; e.g., with the replacement of a P with an S; (c) replacement of the U with a C5 amino linker; (d) replacement of an A with a G (sequence changes are preferred to be located on the sense strand and not the antisense strand); and (d) modification at the 2', 6', 7', or 8' position. Preferred embodiments are those in which one or more of these modifications are present on the sense but not the antisense strand, or embodiments where the antisense strand has fewer of such modifications. Yet other exemplary modifications include the use of a methylated P in a 3' overhang, e.g., at the 3' terminus; combination of a 2' modification, e.g., provision of a 2' O Me moiety and modification of the backbone, e.g., with the replacement of a P with an S, e.g., the provision of a phosphorothioate modification, or the use of a methylated P, in a 3' overhang, e.g., at the 3' terminus; modification with a 3' alkyl; modification with an abasic pyrrolidine in a 3' overhang, e.g., at the 3' terminus; modification with naproxen, ibuprofen, or other moieties which inhibit degradation at the 3' terminus.

4) Modifications to Enhance Cellular Uptake

In other embodiments, RNA silencing agents may be modified with chemical moieties, for example, to enhance cellular uptake by target cells (e.g., neuronal cells). Thus, the invention includes RNA silencing agents which are conjugated or unconjugated (e.g., at its 3' terminus) to another moiety (e.g. a non-nucleic acid moiety such as a peptide), an organic compound (e.g., a dye), or the like. The conjugation can be accomplished by methods known in the art, e.g., using the methods of Lambert et al., Drug Deliv. Rev.:47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

In a particular embodiment, an RNA silencing agent of invention is conjugated to a lipophilic moiety. In one embodiment, the lipophilic moiety is a ligand that includes a cationic group. In another embodiment, the lipophilic moiety is attached to one or both strands of an siRNA. In a preferred embodiment, the lipophilic moiety is attached to one end of the sense strand of the siRNA. In another preferred embodiment, the lipophilic moiety is attached to the 3' end of the sense strand. In certain embodiments, the lipophilic moeity is selected from the group consisting of cholesterol, vitamin E, vitaminK, vitamin A, folic acid, or a cationic dye (e.g., Cy3). In a preferred embodiment, the lipophilic moiety is a cholesterol. Other lipophilic moieties include cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine.

5) Tethered Ligands

Other entities can be tethered to an RNA silencing agent of the invention. For example, a ligand tethered to an RNA silencing agent to improve stability, hybridization thermodynamics with a target nucleic acid, targeting to a particular tissue or cell-type, or cell permeability, e.g., by an endocytosis-dependent or -independent mechanism. Ligands and associated modifications can also increase sequence specificity and consequently decrease off-site targeting. A tethered ligand can include one or more modified bases or sugars that can function as intercalators. These are preferably located in an internal region, such as in a bulge of RNA silencing agent/target duplex. The intercalator can be an aromatic, e.g., a polycyclic aromatic or heterocyclic aromatic compound. A polycyclic intercalator can have stacking capabilities, and can include systems with 2, 3, or 4 fused rings. The universal bases described herein can be included on a ligand. In one embodiment, the ligand can include a cleaving group that contributes to target gene inhibition by cleavage of the target nucleic acid. The cleaving group can be, for example, a bleomycin (e.g., bleomycin-A5, bleomycin-A2, or bleomycin-B2), pyrene, phenanthroline (e.g., O-phenanthroline), a polyamine, a tripeptide (e.g., lys-tyr-lys tripeptide), or metal ion chelating group. The metal ion chelating group can include, e.g., an Lu(III) or EU(III) macrocyclic complex, a Zn(II) 2,9-dimethylphenanthroline derivative, a Cu(II) terpyridine, or acridine, which can promote the selective cleavage of target RNA at the site of the bulge by free metal ions, such as Lu(III). In some embodiments, a peptide ligand can be tethered to a RNA silencing agent to promote cleavage of the target RNA, e.g., at the bulge region. For example, 1,8-dimethyl-1,3,6,8,10,13-hexaazacyclotetradecane (cyclam) can be conjugated to a peptide (e.g., by an amino acid derivative) to promote target RNA cleavage. A tethered ligand can be an aminoglycoside ligand, which can cause an RNA silencing agent to have improved hybridization properties or improved sequence specificity. Exemplary aminoglycosides include glycosylated polylysine, galactosylated polylysine, neomycin B, tobramycin, kanamycin A, and acridine conjugates of aminoglycosides, such as Neo-N-acridine, Neo-S-acridine, Neo-C-acridine, Tobra-N-acridine, and KanaA-N-acridine. Use of an acridine analog can increase sequence specificity. For example, neomycin B has a high affinity for RNA as compared to DNA, but low sequence-specificity. An acridine analog, neo-S-acridine has an increased affinity for the HIV Rev-response element (RRE). In some embodiments the guanidine analog (the guanidinoglycoside) of an aminoglycoside ligand is tethered to an RNA silencing agent. In a guanidinoglycoside, the amine group on the amino acid is exchanged for a guanidine group. Attachment of a guanidine analog can enhance cell permeability of an RNA silencing agent. A tethered ligand can be a poly-arginine peptide, peptoid or peptidomimetic, which can enhance the cellular uptake of an oligonucleotide agent.

Preferred ligands are coupled, preferably covalently, either directly or indirectly via an intervening tether, to a ligand-conjugated carrier. In preferred embodiments, the ligand is attached to the carrier via an intervening tether. In preferred embodiments, a ligand alters the distribution, targeting or lifetime of an RNA silencing agent into which it is incorporated. In preferred embodiments a ligand provides an enhanced affinity for a selected target, e.g, molecule, cell or cell type, compartment, e.g., a cellular or organ compartment, tissue, organ or region of the body, as, e.g., compared to a species absent such a ligand.

Preferred ligands can improve transport, hybridization, and specificity properties and may also improve nuclease resistance of the resultant natural or modified RNA silencing agent, or a polymeric molecule comprising any combination of monomers described herein and/or natural or modified ribonucleotides.

Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophiles, lipids, steroids (e.g., uvaol, hecigenin, diosgenin), terpenes (e.g., triterpenes, e.g., sarsasapogenin, Friedelin, epifriedelanol derivatized lithocholic acid), vitamins (e.g., folic acid, vitamin A, biotin, pyridoxal), carbohydrates, proteins, protein binding agents, integrin targeting molecules polycationics, peptides, polyamines, and peptide mimics.

Ligands can include a naturally occurring substance, (e.g., human serum albumin (HSA), low-density lipoprotein (LDL), or globulin); carbohydrate (e.g., a dextran, pullulan, chitin, chitosan, inulin, cyclodextrin or hyaluronic acid); amino acid, or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl) methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-glucosamine, multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, or an RGD peptide or RGD peptide mimetic.

Other examples of ligands include dyes, intercalating agents (e.g. acridines and substituted acridines), cross-linkers (e.g. psoralene, mitomycin C), porphyrins (TPPC4, texaphyrin, Sapphyrin), polycyclic aromatic hydrocarbons (e.g., phenazine, dihydrophenazine, phenanthroline, pyrenes), lys-tyr-lys tripeptide, aminoglycosides, guanidium aminoglycodies, artificial endonucleases (e.g. EDTA), lipophilic molecules, e.g, cholesterol (and thio analogs thereof), cholic acid, cholanic acid, lithocholic acid, adamantane acetic acid, 1-pyrene butyric acid, dihydrotestosterone, glycerol (e.g., esters (e.g., mono, bis, or tris fatty acid esters, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ fatty acids) and ethers thereof, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ alkyl; e.g., 1,3-bis-O(hexadecyl)glycerol, 1,3-bis-O(octaadecyl)glycerol), geranyloxyhexyl group, hexadecylglycerol, borneol, menthol, 1,3-propanediol, heptadecyl group, palmitic acid, stearic acid (e.g., gyceryl distearate), oleic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, $[MPEG]_2$, polyamino, alkyl, substituted alkyl, radiolabeled markers, enzymes, haptens (e.g. biotin), transport/absorption facilitators (e.g., aspirin, naproxen, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the RNA silencing agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin. The ligand can increase the uptake of the RNA silencing agent into the cell by activating an inflammatory response, for example. Exemplary ligands that would have such an effect include tumor necrosis factor alpha (TNFalpha), interleukin-1 beta, or gamma interferon. In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA. A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney. In a preferred embodiment, the lipid based ligand binds HSA. A lipid-based ligand can bind HSA with a sufficient affinity such that the conjugate will be preferably distributed to a non-kidney tissue. However, it is preferred that the affinity not be so strong that the HSA-ligand binding cannot be reversed. In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HSA and low density lipoprotein (LDL).

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to oligonucleotide agents can affect pharmacokinetic distribution of the RNA silencing agent, such as by enhancing cellular recognition and absorption. The peptide or peptidomimetic moiety can be about 5-50 amino acids long, e.g., about 5, 10, 15, 20, 25, 30, 35, 40, 45, or 50 amino acids long. A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. The peptide moiety can be an L-peptide or D-peptide. In another alternative, the peptide moiety can include a hydrophobic membrane translocation sequence (MTS). A peptide or peptidomimetic can be encoded by a random sequence of DNA, such as a peptide identified from a phage-display library, or one-bead-one-compound (OBOC) combinatorial library (Lam et al., *Nature* 354:82-84, 1991). Preferably the peptide or peptidomimetic tethered to an RNA silencing agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

IV. Methods of Introducing Nucleic Acids, Vectors, and Host Cells

RNA silencing agents of the invention may be directly introduced into the cell (e.g., a neural cell) (i.e., intracellularly); or introduced extracellularly into a cavity, interstitial space, into the circulation of an organism, introduced orally, or may be introduced by bathing a cell or organism in a solution containing the nucleic acid. Vascular or extravascular circulation, the blood or lymph system, and the cerebrospinal fluid are sites where the nucleic acid may be introduced.

The RNA silencing agents of the invention can be introduced using nucleic acid delivery methods known in art including injection of a solution containing the nucleic acid, bombardment by particles covered by the nucleic acid, soaking the cell or organism in a solution of the nucleic acid, or electroporation of cell membranes in the presence of the nucleic acid. Other methods known in the art for introducing nucleic acids to cells may be used, such as lipid-mediated carrier transport, chemical-mediated transport, and cationic liposome transfection such as calcium phosphate, and the like. The nucleic acid may be introduced along with other components that perform one or more of the following activities: enhance nucleic acid uptake by the cell or other-wise increase inhibition of the target gene.

The cell having the target gene may be from the germ line or somatic, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands.

Depending on the particular target gene and the dose of RNA silencing agent material delivered, this process may provide partial or complete loss of function for the target gene. A reduction or loss of gene expression in at least 50%, 60%, 70%, 80%, 90%, 95% or 99% or more of targeted cells is exemplary. Inhibition of gene expression refers to the absence (or observable decrease) in the level of protein and/or mRNA product from a target gene. Specificity refers to the ability to inhibit the target gene without manifest effects on other genes of the cell. The consequences of inhibition can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS).

For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin. Depending on the assay, quantitation of the amount of gene expression allows one to determine a degree of inhibition which is greater than 10%, 33%, 50%, 90%, 95% or 99% as compared to a cell not treated according to the present invention. Lower doses of injected material and longer times after administration of RNA silencing agent may result in inhibition in a smaller fraction of cells (e.g., at least 10%, 20%, 50%, 75%, 90%, or 95% of targeted cells). Quantitation of gene expression in a cell may show similar amounts of inhibition at the level of accumulation of target mRNA or translation of target protein. As an example, the efficiency of inhibition may be determined by assessing the amount of gene product in the cell; mRNA may be detected with a hybridization probe having a nucleotide sequence outside the region used for the inhibitory double-stranded RNA, or translated polypeptide may be detected with an antibody raised against the polypeptide sequence of that region.

The RNA silencing agent may be introduced in an amount which allows delivery of at least one copy per cell. Higher doses (e.g., at least 5, 10, 100, 500 or 1000 copies per cell) of material may yield more effective inhibition; lower doses may also be useful for specific applications.

V. Pharmaceutical Compositions and Methods of Administration

The RNA silencing agents of the invention can be incorporated into pharmaceutical compositions. Such compositions typically include the nucleic acid molecule and a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the RNA silencing agents may be delivered in the form of an aerosol spray from pressured container or dispenser which contains a suitable propellant, e.g., a gas such as carbon dioxide, or a nebulizer. Such methods include those described in U.S. Pat. No. 6,468,798.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The RNA silencing agents can also be prepared in the form of suppositories (e.g., with conventional suppository bases such as cocoa butter and other glycerides) or retention enemas for rectal delivery.

The RNA silencing agents can also be administered by transfection or infection using methods known in the art, including but not limited to the methods described in McCaffrey et al. (2002), Nature, 418(6893), 38-9 (hydrodynamic transfection); Xia et al. (2002), Nature Biotechnol., 20(10), 1006-10 (viral-mediated delivery); or Putnam (1996), Am. J. Health Syst. Pharm. 53(2), 151-160, erratum at Am. J. Health Syst. Pharm. 53(3), 325 (1996).

The RNA silencing agents can also be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al. (1998), Clin. Immunol. Immunopathol., 88(2), 205-10. Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the RNA silencing agents are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Toxicity and therapeutic efficacy of RNA silencing agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. RNA silencing agents which exhibit high therapeutic indices are preferred. While RNA silencing agents that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such RNA silencing agents lies preferably within a range of circulating concentrations that include the ED50 with little or no toxicity. The dosage may vary within this range depending upon the dosage form employed and the route of administration utilized. For any RNA silencing agent used in the method of the invention, the therapeutically effective dose can be estimated initially from cell culture assays. A dose may be formulated in animal models to achieve a circulating plasma concentration range that includes the IC50 (i.e., the concentration of the test RNA silencing agent which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of a RNA silencing agent (i.e., an effective dosage) depends on the RNA silencing agent selected. For instance, if a plasmid encoding shRNA is selected, single dose amounts in the range of approximately 1:g to 1000 mg may be administered; in some embodiments, 10, 30, 100 or 1000:g may be administered. In some embodiments, 1-5 g of the compositions can be administered. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

The nucleic acid molecules of the invention can be inserted into expression constructs, e.g., viral vectors, retroviral vectors, expression cassettes, or plasmid viral vectors, e.g., using methods known in the art, including but not limited to those described in Xia et al., (2002), supra. Expression constructs can be delivered to a subject by, for example, inhalation, orally, intravenous injection, local administration (see U.S. Pat. No. 5,328,470) or by stereotactic injection (see e.g., Chen et al. (1994), Proc. Natl. Acad. Sci. USA, 91, 3054-3057). The pharmaceutical preparation of the delivery vector can include the vector in an acceptable diluent, or can comprise a slow release matrix in which the delivery vehicle is imbedded. Alternatively, where the complete delivery vector can be produced intact from recombinant cells, e.g., retroviral vectors, the pharmaceutical preparation can include one or more cells which produce the gene delivery system.

The nucleic acid molecules of the invention can also include small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21 nucleotides. Brummelkamp et al. (2002), Science, 296, 550-553; Lee et al, (2002). supra; Miyagishi and Taira (2002), Nature Biotechnol., 20, 497-500; Paddison et al. (2002), supra; Paul (2002), supra; Sui (2002) supra; Yu et al. (2002), supra.

The expression constructs may be any construct suitable for use in the appropriate expression system and include, but are not limited to retroviral vectors, linear expression cassettes, plasmids and viral or virally-derived vectors, as known in the art. Such expression constructs may include one or more inducible promoters, RNA Pol III promoter systems such as U6 snRNA promoters or H1 RNA polymerase III promoters, or other promoters known in the art. The constructs can include one or both strands of the siRNA. Expression constructs expressing both strands can also include loop structures linking both strands, or each strand can be separately transcribed from separate promoters within the same construct. Each strand can also be transcribed from a separate expression construct, Tuschl (2002), supra.

In certain exemplary embodiments, a composition that includes an RNA silencing agent of the invention can be delivered to the nervous system of a subject by a variety of routes. Exemplary routes include intrathecal, parenchymal (e.g., in the brain), nasal, and ocular delivery. The composition can also be delivered systemically, e.g., by intravenous, subcutaneous or intramuscular injection, which is particularly useful for delivery of the RNA silencing agents to peripheral neurons. A preferred route of delivery is directly to the brain, e.g., into the ventricles or the hypothalamus of the brain, or into the lateral or dorsal areas of the brain. The RNA silencing agents for neural cell delivery can be incorporated into pharmaceutical compositions suitable for administration. For example, compositions can include one or more species of an RNA silencing agent and a pharmaceutically acceptable carrier. The pharmaceutical compositions of the present invention may be administered in a number of ways depending upon whether local or systemic treatment is desired and upon the area to be treated. Administration may be topical (including ophthalmic, intranasal, transdermal), oral or parenteral. Parenteral administration includes intravenous drip, subcutaneous, intraperitoneal or intramuscular injection, intrathecal, or intraventricular (e.g., intracerebroventricular) administration.

The route of delivery can be dependent on the disorder of the patient. For example, a subject diagnosed with HD can be administered anti-htt RNA silencing agents of the invention directly into the brain (e.g., into the globus pallidus or the corpus striatum of the basal ganglia, and near the medium spiny neurons of the corpus striatum). In addition to RNA silencing agents of the invention, a patient can be administered a second therapy, e.g., a palliative therapy and/or disease-specific therapy. The secondary therapy can be, for example, symptomatic, (e.g., for alleviating symptoms), neuroprotective (e.g., for slowing or halting disease progression), or restorative (e.g., for reversing the disease process). For the treatment of HD, for example, symptomatic therapies can include the drugs haloperidol, carbamazepine, or valproate. Other therapies can include psychotherapy, physiotherapy, speech therapy, communicative and memory aids, social support services, and dietary advice.

RNA silencing agents can be delivered to neural cells of the brain. Delivery methods that do not require passage of the composition across the blood-brain barrier can be utilized. For example, a pharmaceutical composition containing RNA silencing agents can be delivered to the patient by injection directly into the area containing the disease-affected cells. For example, the pharmaceutical composition can be delivered by injection directly into the brain. The injection can be by stereotactic injection into a particular region of the brain (e.g., the substantia nigra, cortex, hippocampus, striatum, or globus pallidus). The RNA silencing agents can be delivered into multiple regions of the central nervous system (e.g., into multiple regions of the brain, and/or into the spinal cord). The RNA silencing agents can be delivered into diffuse regions of the brain (e.g., diffuse delivery to the cortex of the brain).

In one embodiment, the RNA silencing agents can be delivered by way of a cannula or other delivery device having one end implanted in a tissue, e.g., the brain, e.g., the substantia nigra, cortex, hippocampus, striatum or globus pallidus of the brain. The cannula can be connected to a reservoir of RNA silencing agents. The flow or delivery can be mediated by a pump, e.g., an osmotic pump or minipump, such as an Alzet pump (Durect, Cupertino, Calif.). In one embodiment, a pump and reservoir are implanted in an area distant from the tissue, e.g., in the abdomen, and delivery is effected by a conduit leading from the pump or reservoir to the site of release. Devices for delivery to the brain are described, for example, in U.S. Pat. Nos. 6,093,180, and 5,814,014.

RNA silencing agents of the invention can be further modified such that it is capable of traversing the blood brain barrier. For example, a RNA silencing agent can be conjugated to a molecule that enables the agent to traverse the barrier. Such modified RNA silencing agents can be administered by any desired method, such as by intraventricular or intramuscular injection, or by pulmonary delivery, for example.

RNA silencing agents of the invention can be administered ocularly, such as to treat retinal disorder, e.g., a retinopathy. For example, the pharmaceutical compositions can be applied to the surface of the eye or nearby tissue, e.g., the inside of the eyelid. They can be applied topically, e.g., by spraying, in drops, as an eyewash, or an ointment. Ointments or droppable liquids may be delivered by ocular delivery systems known in the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers. The pharmaceutical composition can also be administered to the interior of the eye, and can be introduced by a needle or other delivery device which can introduce it to a selected area or structure. The composition containing the RNA silencing agents can also be applied via an ocular patch.

In general, RNA silencing agents of the invention can be administered by any suitable method. As used herein, topical delivery can refer to the direct application of RNA silencing agents to any surface of the body, including the eye, a mucous membrane, surfaces of a body cavity, or to any internal surface. Formulations for topical administration may include transdermal patches, ointments, lotions, creams, gels, drops, sprays, and liquids. Conventional pharmaceutical carriers, aqueous, powder or oily bases, thickeners and the like may be necessary or desirable. Topical administration can also be used as a means to selectively deliver RNA silencing agents to the epidermis or dermis of a subject, or to specific strata thereof, or to an underlying tissue.

Compositions for intrathecal or intraventricular (e.g., intracerebroventricular) administration may include sterile aqueous solutions which may also contain buffers, diluents and other suitable additives. Compositions for intrathecal or intraventricular administration preferably do not include a transfection reagent or an additional lipophilic moiety besides, for example, the lipophilic moiety attached to RNA silencing agents.

Formulations for parenteral administration may include sterile aqueous solutions which may also contain buffers, diluents and other suitable additives. Intraventricular injection may be facilitated by an intraventricular catheter, for example, attached to a reservoir. For intravenous use, the total concentration of solutes should be controlled to render the preparation isotonic.

RNA silencing agents of the invention can be administered to a subject by pulmonary delivery. Pulmonary delivery compositions can be delivered by inhalation of a dispersion so that the composition within the dispersion can reach the lung where it can be readily absorbed through the alveolar region directly into blood circulation. Pulmonary delivery can be effective both for systemic delivery and for localized delivery to treat diseases of the lungs. In one embodiment, RNA silencing agents administered by pulmonary delivery have been modified such that they are capable of traversing the blood brain barrier.

Pulmonary delivery can be achieved by different approaches, including the use of nebulized, aerosolized, micellular and dry powder-based formulations. Delivery can be achieved with liquid nebulizers, aerosol-based inhalers, and dry powder dispersion devices. Metered-dose devices are preferred. One of the benefits of using an atomizer or inhaler is that the potential for contamination is minimized because the devices are self contained. Dry powder dispersion devices, for example, deliver drugs that may be readily formulated as dry powders. RNA silencing agents composition may be stably stored as lyophilized or spray-dried powders by itself or in combination with suitable powder carriers. The delivery of a composition for inhalation can be mediated by a dosing timing element which can include a timer, a dose counter, time measuring device, or a time indicator which when incorporated into the device enables dose tracking, compliance monitoring, and/or dose triggering to a patient during administration of the aerosol medicament.

The types of pharmaceutical excipients that are useful as carriers include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Bulking agents that are particularly valuable include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-.beta.-cyclodextrin; and polysaccharides, such as raffinose, maltodextrins, dextrans, and the like; alditols, such as mannitol, xylitol, and the like. A preferred group of carbohydrates includes lactose, threhalose, raffinose maltodextrins, and mannitol. Suitable polypeptides include aspartame. Amino acids include alanine and glycine, with glycine being preferred.

Suitable pH adjusters or buffers include organic salts prepared from organic acids and bases, such as sodium citrate, sodium ascorbate, and the like; sodium citrate is preferred.

RNA silencing agents of the invention can be administered by oral and nasal delivery. For example, drugs administered through these membranes have a rapid onset of action, provide therapeutic plasma levels, avoid first pass effect of hepatic metabolism, and avoid exposure of the drug to the hostile gastrointestinal (GI) environment. Additional advantages include easy access to the membrane sites so that the drug can be applied, localized and removed easily. In one embodiment, RNA silencing agents administered by oral or nasal delivery have been modified to be capable of traversing the blood-brain barrier.

In one embodiment, unit doses or measured doses of a composition that include RNA silencing agents are dispensed by an implanted device. The device can include a sensor that monitors a parameter within a subject. For example, the device can include a pump, such as an osmotic pump and, optionally, associated electronics.

RNA silencing agents can be packaged in a viral natural capsid or in a chemically or enzymatically produced artificial capsid or structure derived therefrom.

VI. Methods of Treatment

The present invention provides for both prophylactic and therapeutic methods of treating a subject at risk of (or susceptible to) of Huntington's disease.

"Treatment", or "treating" as used herein, is defined as the application or administration of a therapeutic agent (e.g., a RNA agent or agents or vector or transgene encoding same) to a patient, or application or administration of a therapeutic agent to an isolated tissue or cell line from a patient, who has the disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

In one aspect, the invention provides a method for preventing Huntington's disease in a subject, by administering to the subject a therapeutic agent (e.g., a RNA silencing agent or agents or vector or transgene encoding same). Subjects at risk for the disease can be identified by, for example, any or a combination of diagnostic or prognostic assays as described herein. Administration of a prophylactic agent can occur prior to the manifestation of symptoms characteristic of the disease or disorder, such that the disease or disorder is prevented or, alternatively, delayed in its progression.

Another aspect of the invention pertains to methods treating subjects therapeutically, i.e., alter onset of symptoms of the disease or disorder. In an exemplary embodiment, the modulatory method of the invention involves contacting a cell expressing a gain-of-function mutant with a therapeutic agent (e.g., a RNA silencing agent or agents or vector or transgene encoding same) that is specific for a mutation within the gene, such that sequence specific interference with the gene is achieved. These methods can be performed in vitro (e.g., by culturing the cell with the agent) or, alternatively, in vivo (e.g., by administering the agent to a subject).

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the target gene molecules of the present invention or target gene modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

Moreover, patients can be screened to determine the SNP isoform associated with the expanded CAG repeat Htt allele and the corresponding siRNA (siRNAs) selected for therapy. Methods for such screening are known in the art, and include, for example, the SNP linkage by circularization (SLiC) method described by Liu et al., Nature Methods (2008), 5(11):951-953, the entire contents of which are incorporated herein by reference.

Therapeutic agents can be tested in an appropriate animal model. For example, an RNA silencing agent (or expression vector or transgene encoding same) as described herein can be used in an animal model to determine the efficacy, toxicity, or side effects of treatment with said agent. Alternatively, a therapeutic agent can be used in an animal model to determine the mechanism of action of such an agent. For example, an agent can be used in an animal model to determine the efficacy, toxicity, or side effects of treatment with such an agent. Alternatively, an agent can be used in an animal model to determine the mechanism of action of such an agent.

A pharmaceutical composition containing an RNA silencing agent or agents of the invention can be administered to any patient diagnosed as having or at risk for developing a neurological disorder, such as HD. In one embodiment, the patient is diagnosed as having a neurological disorder, and the patient is otherwise in general good health. For example, the patient is not terminally ill, and the patient is likely to live at least 2, 3, 5, or 10 years or longer following diagnosis. The patient can be treated immediately following diagnosis, or treatment can be delayed until the patient is experiencing more debilitating symptoms, such as motor fluctuations and dyskinesis in PD patients. In another embodiment, the patient has not reached an advanced stage of the disease.

An RNA silencing agent modified for enhance uptake into neural cells can be administered at a unit dose less than about 1.4 mg per kg of bodyweight, or less than 10, 5, 2, 1, 0.5, 0.1, 0.05, 0.01, 0.005, 0.001, 0.0005, 0.0001, 0.00005 or 0.00001 mg per kg of bodyweight, and less than 200 nmole of RNA agent (e.g., about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmole of RNA silencing agent per kg of bodyweight. The unit dose, for example, can be administered by injection (e.g., intravenous or intramuscular, intrathecally, or directly into the brain), an inhaled dose, or a topical application. Particularly preferred dosages are less than 2, 1, or 0.1 mg/kg of body weight.

Delivery of RNA silencing agents directly to an organ (e.g., directly to the brain) can be at a dosage on the order of about 0.00001 mg to about 3 mg per organ, or preferably about 0.0001-0.001 mg per organ, about 0.03-3.0 mg per organ, about 0.1-3.0 mg per eye or about 0.3-3.0 mg per organ. The dosage can be an amount effective to treat or prevent a neurological disease or disorder, e.g., HD. In one embodiment, the unit dose is administered less frequently than once a day, e.g., less than every 2, 4, 8 or 30 days. In another embodiment, the unit dose is not administered with a frequency (e.g., not a regular frequency). For example, the unit dose may be administered a single time. In one embodiment, the effective dose is administered with other traditional therapeutic modalities.

In one embodiment, a subject is administered an initial dose, and one or more maintenance doses of an RNA silencing agent. The maintenance dose or doses are generally lower than the initial dose, e.g., one-half less of the initial dose. A maintenance regimen can include treating the subject with a dose or doses ranging from 0.01 μg to 1.4 mg/kg of body weight per day, e.g., 10, 1, 0.1, 0.01, 0.001, or 0.00001 mg per kg of bodyweight per day. The maintenance doses are preferably administered no more than once every 5, 10, or 30 days. Further, the treatment regimen may last for a period of time which will vary depending upon the nature of the particular disease, its severity and the overall condition of the patient. In preferred embodiments the dosage may be delivered no more than once per day, e.g., no more than once per 24, 36, 48, or more hours, e.g., no more than once every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable. In one embodiment, a pharmaceutical composition includes a plurality of RNA silencing agent species. In another embodiment, the RNA silencing agent species has sequences that are non-overlapping and non-adjacent to another species with respect to a naturally occurring target sequence. In another embodiment, the plurality of RNA silencing agent species is specific for different naturally occurring target genes. In another embodiment, the RNA silencing agent is allele specific. In another embodiment, the plurality of RNA silencing agent species target two or more SNP alleles (e.g., two, three, four, five, six, or more SNP alleles).

Following successful treatment, it may be desirable to have the patient undergo maintenance therapy to prevent the recurrence of the disease state, wherein the compound of the invention is administered in maintenance doses, ranging from 0.01 μg to 100 g per kg of body weight (see U.S. Pat. No. 6,107,094).

The concentration of the RNA silencing agent composition is an amount sufficient to be effective in treating or preventing a disorder or to regulate a physiological condition in humans. The concentration or amount of RNA silencing agent administered will depend on the parameters determined for the agent and the method of administration, e.g. nasal, buccal, or pulmonary. For example, nasal formulations tend to require much lower concentrations of some ingredients in order to avoid irritation or burning of the nasal passages. It is sometimes desirable to dilute an oral formulation up to 10-100 times in order to provide a suitable nasal formulation.

Certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an RNA silencing agent can include a single treatment or, preferably, can include a series of treatments. It will also be appreciated that the effective dosage of an RNA silencing agent for treatment may increase or decrease over the course of a particular treatment. Changes in dosage may result and become apparent from the results of diagnostic assays as described herein. For example, the subject can be monitored after administering an RNA silencing agent composition. Based on information from the monitoring, an additional amount of the RNA silencing agent composition can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds, and can generally be estimated based on EC50s found to be effective in in vitro and in vivo animal models. In some embodiments, the animal models include transgenic animals that express a human gene, e.g., a gene that produces a target RNA, e.g., an RNA expressed in a neural cell. The transgenic animal can be deficient for the corresponding endogenous RNA. In another embodiment, the composition for testing includes an RNA silencing agent that is complementary, at least in an internal region, to a sequence that is conserved between the target RNA in the animal model and the target RNA in a human.

VII. Kits

In certain other aspects, the invention provides kits that include a suitable container containing a pharmaceutical formulation of one or more RNA silencing agents, e.g., a double-stranded RNA silencing agent, or sRNA agent, (e.g., a precursor, e.g., a larger RNA silencing agent which can be processed into a sRNA agent, or a DNA which encodes an RNA silencing agent, e.g., a double-stranded RNA silencing agent, or sRNA agent, or precursor thereof). In certain embodiments the individual components of the pharmaceutical formulation may be provided in one container. Alternatively, it may be desirable to provide the components of the pharmaceutical formulation separately in two or more containers, e.g., one container for an RNA silencing agent preparation, and at least another for a carrier compound. The kit may be packaged in a number of different configurations such as one or more containers in a single box. The different components can be combined, e.g., according to instructions provided with the kit. The components can be combined according to a method described herein, e.g., to prepare and administer a pharmaceutical composition. The kit can also include a delivery device.

This invention is further illustrated by the following examples which should not be construed as limiting. The contents of all references, patents and published patent applications cited throughout this application are incorporated herein by reference.

EXAMPLES

Patient Samples, Sequencing, and Statistical Analysis

Patient brain samples were obtained from brain repositories in Charlestown, Mass. and New York, N.Y., and DNA from the DNA repository in Ulm, Germany. Genomic DNA was either extracted from brain tissue (USA patients) using a genomic DNA extraction kit (Lamda Biotech, St. Louis, Mo.) or obtained as purified (German patients). Candidate SNP sequences were amplified by PCR (Table 3) and sequenced (GENEWIZ, South Plainfield, N.J., USA, and Macrogen, Rockville, Md., USA). To identify new SNP sites, six subjects were selected for sequencing of all 67 Huntingtin exons. All electrophoretograms were manually inspected for the forward and reverse directions.

TABLE 3

| | | Primers used for SNP analysis and resequencing | | | |
|---|---|---|---|---|---|
| Exon | SNP i.d. | Forward primer | SEQ ID NO | Reverse primer | SEQ ID NO |
| 2 | | 5'-TGGAGTGGGTAATTCAACACA-3' | 50 | 5'-GCCAGAAATATGGGAAAAGG-3' | 51 |
| 3 | | 5'-AGAATTCCATGCAGGACACC-3' | 52 | 5'-GCAGACATCCTCAGGGACTC-3' | 53 |
| 4 | | 5'-TGATGGGATGTGTCTTCCAT-3' | 54 | 5'-GGTCAGGAGTTCGAGACCAG-3' | 55 |
| 5 | | 5'-ATGCAACCCTCTTGGTGACT-3' | 56 | 5'-CGACAAAAACCAACATCCAG-3' | 57 |
| 6 | | 5'-TCAGCTGAGTTTTCCCCATC-3' | 58 | 5'-GAAGCACTCCCACAGGACTC-3' | 59 |
| 7 | | 5'-CTGCTCTTGAGTGTCCCAAA-3' | 60 | 5'-CCACTCATATGCCTCCACCT-3' | 61 |
| 8 | | 5'-CTCTGGAAAGGACCTTGCTG-3' | 62 | 5'-ATTCACATGCAGGGCCTAGA-3' | 63 |
| 9 | | 5'-TTGGTGGAAGTGATAGGGAAA-3' | 64 | 5'-GTTTTGGCAAGGAAGATGGA-3' | 65 |
| 10 | | 5'-TGCGATGTTAAGTGTTTCCTG-3' | 66 | 5'-CCTGGTTATCAGATTCCAGCA-3' | 67 |
| 11 | | 5'-GCATTTACTTAATTTTGAAGTCCTTAT-3' | 68 | 5'-CGAATATGCCCCATTTAAGC-3' | 69 |
| 12 | | 5'-CGTTATTTTGCAAGCCTGTG-3' | 70 | 5'-CTCCCAAAGTGCTGGGATTA-3' | 71 |
| 13, 14 | | 5'-GTTGGAGGGCTTGTCTCTTG-3' | 72 | 5'-CAGGGATGGGAAAGCAATAA-3' | 73 |
| 15, 16 | | 5'-ACCTGGCTTAAGTGCTGCTC-3' | 74 | 5'-CTCGGCTAGTGAAAACCAAA-3' | 75 |
| 17, 18 | | 5'-GTTCCATGGCTGAGCAATTT-3' | 76 | 5'-GCTGAGAGATGGATACATGGTG-3' | 77 |
| 19 | | 5'-CTTGCCTTGGACCTTGTGTT-3' | 78 | 5'-TGCATCAAGTGATCCCAGAA-3' | 79 |
| 20, 21 | rs363075 | 5'-CAAGCTGGCGGTAAGTGTTT-3' | 80 | 5'-TCCCTCTCTTTCCATTCTCG-3' | 81 |
| 22 | | 5'-AAGTGGTGTCCGCTGGTAAC-3' | 82 | 5'-GCCTAAAGAAAGGCATCAGG-3' | 83 |
| 23 | | 5'-CGTTTCACTTAAAAGTTGAGACTGC-3' | 84 | 5'-TTTCTTAGCAAGCCTCATGGA-3' | 85 |
| 24 | | 5'-CTTTGTGGTGTTTGGGTGTG-3' | 86 | 5'-TCCCACAGCTCCTGTCACTA-3' | 87 |

TABLE 3-continued

Primers used for SNP analysis and resequencing

| Exon | SNP i.d. | Forward primer | SEQ ID NO | Reverse primer | SEQ ID NO |
|---|---|---|---|---|---|
| 25 | rs35892913, rs1605746, rs17781557 | 5'-TGTGACATGCCTTCCTCTTG-3' | 88 | 5'-AAAGGGACAAGCCATCACTG-3' | 89 |
| 26 | | 5'-CAGTTCCCCAAGCAATTTGT-3' | 90 | 5'-CCATCCACATGGTCACATTT-3' | 91 |
| 27 | | 5'-TCAGGGTCCAAGAACAAAATG-3' | 92 | 5'-GCTTCAGACCAAAAGGTGGT-3' | 93 |
| 28 | | 5'-TTTCCAGTAATCTCTTTAAAACTTGG-3' | 94 | 5'-TAAAAGATGCAGAGGCCCAT-3' | 95 |
| 29 | rs4690074 | 5'-GGCCAGTAACCGTGTGTTCT-3' | 96 | 5'-TCATGGCTAAGGCAGAGTCA-3' | 97 |
| 30 | | 5'-GGATTCGTACAATAACGGGTCA-3' | 98 | 5'-GGAGCTTCTGGTGTCCTCTG-3' | 99 |
| 31 | | 5'-TTCACGCTGTGAGTCTTTGC-3' | 100 | 5'-CTCTTTCGTGCTTCCACCA-3' | 101 |
| 32 | | 5'-TGCTTCCCTTTTATTCCCATT-3' | 102 | 5'-CCTGGAAAGTCTCAGCTCCA-3' | 103 |
| 33 | | 5'-TGCTTGAAGCTTTTAGTTGAAGG-3' | 104 | 5'-ATGAGGGAAACATGCAGACC-3' | 105 |
| 34 | | 5'-TGTGAAATTTTATTTTCCTTCCTG-3' | 106 | 5'-TTCCATTTAAAGAAAACAGCAAAA-3' | 107 |
| 35 | | 5'-TGATGTGTGCTTGCTGTCAA-3' | 108 | 5'-ACACACATGCAGAGCCTGAG-3' | 109 |
| 36 | | 5'-GATGTTGAGAGCAGTTTTCCAA-3' | 110 | 5'-GCCCAAACCTGGTTCAAAGT-3' | 111 |
| 37 | | 5'-CGTCTCTTGGCAGCAGACTT-3' | 112 | 5'-TATGCAACAACAAGCCAAGG-3' | 113 |
| 38 | | 5'-GGTGTACAGGAAGCTGTCGTT-3' | 114 | 5'-GCCCTACCCAAACTGACTGA-3' | 115 |
| 39 | rs363125 | 5'-GCAATTGGGGGAAATTTAATC-3' | 116 | 5'-CATCACGTGACTTCCCAAAA-3' | 117 |
| 40 | | 5'-TGTATACTTGGCGTAAGTGCTTT-3' | 118 | 5'-ACTGGGCAAGGCAGAGTTT-3' | 119 |
| 41 | | 5'-GGACCGAGATGAAAGCAAAG-3' | 120 | 5'-GCCAAAGCTCAGGTTACTGG-3' | 121 |
| 42 | | 5'-CTCACTGCCATCCAGAAACA-3' | 122 | 5'-TTTAGTTTCGATGGAGCTTGG-3' | 123 |
| 43 | | 5'-GGCATTAATACCTGGTCTCTTCTT-3' | 124 | 5'-TTTAAGGCAGGGAAAACTGC-3' | 125 |
| 44 | | 5'-ATTGCCAGTTGCAGTTTTCC-3' | 126 | 5'-AAAAGCCAGCCACCTGTTTT-3' | 127 |
| 45 | | 5'-TGAACTGTACACATCAGTTCATCC-3' | 128 | 5'-TAAACCCACCTATAAGGCACATC-3' | 129 |
| 46 | | 5'-TGTATTTTCCTTTAAGAAGCCACT-3' | 130 | 5'-ACAGGTGACAGAGGCACTCA-3' | 131 |
| 47 | | 5'-AGCTCCAGGGATGTGAAGTC-3' | 132 | 5'-CAGACTGGAGTCCCCAACAT-3' | 133 |
| 48 | rs362336 | 5'-TGTTTGTTAACCTTTAATGCTCTGA-3' | 134 | 5'-TATACTGGCCCTGGAATGCT-3' | 135 |
| 49 | | 5'-GCTTGACTGCCTTTCGAAGT-3' | 136 | 5'-TGGAAAAGTGACTGGACTGG-3' | 137 |
| 50 | rs362331 | 5'-GGGCATTCTGTGACTCGGTA-3' | 138 | 5'-GATAGGAACCCACCGTTCAT-3' | 139 |
| 51 | | 5'-GGCTAGTCTGTCTATCCCTTTCA-3' | 140 | 5'-TCCAGGAGTCCACACTCACC-3' | 141 |
| 52 | | 5'-CAGCTGGTTGTAGGTCATGC-3' | 142 | 5'-GGTCTTCTGCAAGGAACGAG-3' | 143 |
| 53 | | 5'-GCTTCCTGCTTCCTCACAGT-3' | 144 | 5'-TTGCCAACACTGCAAAATGT-3' | 145 |
| 54 | | 5'-ACAGGCTTGAGAAGGGTTGA-3' | 146 | 5'-AGACCTCAGCAGGCTTTGTC-3' | 147 |
| 55 | | 5'-GAGGTGGTTGTGGGTGTCTT-3' | 148 | 5'-CACCTTTGGGTCTGCATCTC-3' | 149 |
| 56 | | 5'-CACGGACAGGTGCTCACTTA-3' | 150 | 5'-GGTGAGCATGCCAGTCTTCT-3' | 151 |
| 57 | rs362273 | 5'-AGTGACAAATCCCCAAGACC-3' | 152 | 5'-GAGCTTTTCTCCTGGGTGTG-3' | 153 |
| 58, 59 | | 5'-TAGACGGTAGGCATGTGCTG-3' | 154 | 5'-GTGTGGCCTGTGTGTGTGTT-3' | 155 |
| 60 | | 5'-GGATTCTAACAGCGCGATTC-3' | 156 | 5'-GTTCGGGTCAACTCTTGGAA-3' | 157 |

TABLE 3-continued

Primers used for SNP analysis and resequencing

| Exon | SNP i.d. | Forward primer | SEQ ID NO | Reverse primer | SEQ ID NO |
|---|---|---|---|---|---|
| 61 | rs362272 | 5'-CGGCCTGCTGTGTAGTCTCT-3' | 158 | 5'-TCTTGCGTCTCACTGACCTC-3' | 159 |
| 62, 63 | | 5'-ACATGCTGTGAAGCCCTCTC-3' | 160 | 5'-GTCGAGGTCCCTTGAGTGAG-3' | 161 |
| 64 | | 5'-CCCCTGTGTACAAAGCACTG-3' | 162 | 5'-GCTGTGGTGGGGAATCACT-3' | 163 |
| 65 | rs3025806 | 5'-ATTTCACATCGGCATTTTCC-3' | 164 | 5'-AACTCCACCTCCAGGCTTTC-3' | 165 |
| 66 | | 5'-GAAAGCCTGGAGGTGGAGTT-3' | 166 | 5'-ACATGAGCCTCGGTGTTGAC-3' | 167 |
| 67 (primer set 1) | rs362308, rs362307 | 5'-GCTCTGCTCGCTCTCCAG-3' | 168 | 5'-GCAGAGACACGCACGTTG-3' | 169 |
| 67 (primer set 2) | rs362306, rs362268, rs362305, rs362304, rs362303 | 5'-TGACCAGGTCCTTTCTCCTG-3' | 170 | 5'-GGCCTTGCGATTCACATACT-3' | 171 |
| 67 (primer set 3) | rs1557210, rs362302, rs3025805, rs362267 | 5'-ATGGATGCATGCCCTAAGAG-3' | 172 | 5'-TCTAGGGCTGAGGAAGCAGA-3' | 173 |

One hundred-nine case and 116 control genomes from German and US populations were typed at 24 SNP positions in the HD gene on human chromosome 4. Of these, 9 were discarded because they were rarely heterozygous. All assayed SNPs had a call rate greater than 95%. Four SNPs with a minimal allele frequency (MAF) of less than 0.01 were removed from the set. Deviations from Hardy-Weinberg equilibrium (HWE) were determined with Pearson goodness-of-fit and Fisher's exact tests. All markers resulted in HWE p-values of greater than 0.01. Single SNP associations were calculated for associations of markers with the HD phenotype. Test statistics of the Pearson goodness-of-fit test was determined and significance evaluated against the chisquared distribution and against an empirical distribution of the statistic after 1000 permutations. Association was also tested with the Fisher's exact test and the Cochran-Armitage test. A single marker, rs362307, was found to be associated with a significance of 0.0000523. This marker remained significant after Bonferroni multiple testing adjustment for 17 tests at the level of 0.000890. SNP rs362307 is located in a ~80 kb block of 10 markers whose average local linkage disequilibrium value is D'=0.995666. The power of the study to detect association at p<0.01 was >90%.

All statistical calculations were performed using the Haploview software, version 3.32 (Barrett et al., 2005) and R(R: Development core team (2004). R: A language and environment for statistical computing. Vienna, Austria. http://www.r-project.org). SNP data were imported into R and formatted for input into Haploview software.

Reporter Constructs and Assays

For rs363125, a 55-mer containing the SNP site (for 5'-cta gag GTT AAG AGA TGGGGA CAG TA[C/A] TTC AAC GCT AGA AGA ACA CAc tcg age t-3' (SEQ ID NO:174), rev 5'-cta gag ctcgag TGT GTT CTT CTA GCG TTG AA[G/T] TAC TGT CCC CAT CTC TTA ACc t-3' (SEQ ID NO:175)) was cloned into the pRL-TK vector (Promega Corporation, Madison, Wis.) using the XbaI site in the 3' UTR of the Renilla luciferase gene. Proper insertion was confirmed by PCR and sequencing. Luciferase assays were performed by co-transfection in 24 well plates of the siRNA with 0.025 mg/well of the SNP reporter (pRL3125) and 0.05 mg/well pGL3-control vector (Promega). For dose-response measurements, GFP siRNA (guide: 5'-GCA AGC UGA CCC UGA AGU UAA U-3' (SEQ ID NO:176); passenger: 5'-GAA CUU CAG GGU CAG CUU GCC G-3' (SEQ ID NO:177)) was added to each transfection mixture so that all transfections contained 20 nM total siRNA. Transfections were performed using Lipofectamine 2000 (Invitrogen Corporation, Carlsbad, Calif.), according to the manufacturer's protocol. Twenty-four hours after transfection the cells were lysed for 20 min in 1× passive lysis buffer (Promega). Luciferase activity was read in 96-well plates with the Dual-luciferase assay kit (Promega) using the GloMax multi-detection system (Promega).

For rs362307 and rs362273, a 45-mer (rs362273 forward: 5'-tcg aAG CCA CGAG AA GCT GCT GCT [A/G]CA GAT CAA CCC CGA GCG GGA-3' (SEQ ID NO:178), reverse: 5'-ggc cTCCCG CTC GGG GTT GAT CTG [T/C]AG CAG CAG CTT CTC GTG GCT-3' (SEQ ID NO:179), rs362307 forward: 5'-tcg aCC GGA GCC TTT GGA AGT CTG [C/T] GC CCT TGT GCC CTG CCTCCA-3' (SEQ ID NO:180), reverse: 5'-ggc cTG GAG GCA GGG CAC AAG GGC [G/A] CA GAC TTC CAA AGG CTC CGG-3' (SEQ ID NO:181)) containing the SNP site was cloned into pSiCHECK-2 (Promega) between the XhoI and NotI restriction sites in the 3' UTR of a codon-optimized form of the Renilla reniformis luciferase gene. 0.025 mg/well of the psiCHECK vector were used in the luciferase assays, which were performed as above. Data were graphed and analyzed using Igor Pro software (WaveMetrics, Portland, Oreg.).

Western Blotting

Cells were grown and transfected in 6-well plates. The final concentration of total siRNA transfected in each well was 20 nM (GFP siRNA plus Huntingtin siRNA). An siRNA targeting a non-polymorphic site in the Huntingtin mRNA ("E1-4"; guide: 5'-UUC AUC AGC UUU UCC AGG GUC-3' (SEQ ID NO:182); passenger: 5'-CCC UGG AAA AGC UGA UGA CGG-3' (SEQ ID NO:183)) served as a positive control. Cells were lysed 48 hours after transfection using Passive Lysis Buffer (Promega) supplemented with protease inhibitors (Roche Applied Science, Indianapolis, Ind., USA). Samples were diluted in Laemmli Sample buffer (Bio-Rad Laboratories, Hercules, Calif., USA) and resolved by electrophoresis through a 4-15% polyacrylamide denaturing Tris-HCl gel (Bio-Rad). After transfer to PVDF, blots were probed with anti-Huntingtin antibody (Ab1, 0.5 mg/ml) (DiFiglia et al., 1995) followed by an HRPconjugated anti-rabbit secondary antibody (NA934V, GE Healthcare, Buckinghamshire, UK) diluted 1:10,000. Chemiluminescent detection was performed with SuperSignal West Dura Extended Duration Substrate (Thermo Scientific, Pierce, Rockford, Ill., USA) and images acquired with an LAS-3000 imaging system (Fujifilm, Tokyo, Japan). After probing with the anti-Huntingtin antibody, blots were stripped and re-probed with anti-a-Tubulin antibody (DM1A, Sigma Aldrich, St. Louis, Mo., 1:1000) detected with anti-mouse secondary antibody (NA931V, GE Healthcare) diluted 1:10,000.

Quantitative PCR

Cells were grown and transfected in 6-well plates. The final concentration of total siRNA transfected in each well was 20 nM (GFP siRNA plus Huntingtin siRNA). RNA was extracted 24 h after transfection using TRI reagent solution (Ambion, Austin, Tex.), and then DNase treated with Turbo DNA-free DNase (Ambion). cDNA was synthesized using oligo(dT) primers, Superscript III reverse transcriptase (Invitrogen Corporation, Carlsbad, Calif.) and 0.5 µg total RNA. Quantitative PCR reactions were performed with primers to amplify Huntingtin (forward, 5'-cgc aga gtc aga tgt cag ga-3' (SEQ ID NO:184); reverse, 5'-ggg tct ctt get tgt tcg ag-3' (SEQ ID NO:185)) or β-actin mRNA (forward, 5'-gga ctt cga gca aga gat gg-3' (SEQ ID NO:186); reverse, 5'-agc act gtg ttg gcg tac ag-3' (SEQ ID NO:187)) using the Quantitect SYBR Green PCR kit (Qiagen, Valencia, Calif.). Data were analyzed using the $2^{-\Delta\Delta C_T}$ method (Livak and Schmittgen, 2001) and β-actin mRNA for normalization.

Example I

Sequencing and Analysis of Huntingtin SNP Sites in HD and Control Patients

Twelve PCR amplicons spanning 22 known SNP sites in Huntingtin were sequenced using genomic DNA from 109 Huntington's disease (HD) patients and 116 non-HD controls (FIG. 1A). The sequenced DNA encompassed six complete coding exons and the portion of exon 67 that contains the stop codon and part of the 3' untranslated region (UTR). Twenty-two of the SNP sites were reported in the SNPper database (Riva and Kohane, 2004; Riva and Kohane, 2002). Four of these reported SNP sites were present only as a single isoform in our population. Two additional sites were identified by resequencing exons 2-67 in the Huntingtin locus from six HD patient samples. Table 1 reports the frequency of heterozygosity for each SNP site for patient and control DNA.

Of the 24 SNPs, rs362307 at nucleotide (nt) 9,633 (exon 67) of the mRNA was significantly associated with HD (p=0.0000523). After Bonferroni correction for multiple testing, the association remained significant (p=0.000890). More than 48% of the HD patients examined—which are believed to be representative of the US and European patient pool—were heterozygous at this site (Table 1). The U isoform of the rs362307 SNP comprised 26% of Huntingtin alleles among the patients tested, but only 6% of alleles among the controls. This finding suggests that a single, allele-specific siRNA selectively targeting the U mRNA isoform of this SNP could be used to treat nearly half of this patient population. To confirm the statistical analysis, a previously reported method was used to determine the rs362307 SNP isoform linked to the CAG repeat expansion allele using SLiC (Liu et al., 2008) for 16 patient blood samples. Eight out of the 16 patients were heterozygous at this site; of the 8, the U isoform was linked to the expanded CAG repeat for 7 patients (Table 4). Thus it is concluded that the U isoform of this SNP is associated with the disease allele of Huntingtin mRNA.

TABLE 4

The U isoform of SNP rs362307 at Huntingtin mRNA nucleotide 9,633 is associated with the expanded CAG disease allele

| | | Linkage | |
|---|---|---|---|
| Patient number | Nucleotide | Mutant allele | Normal allele |
| 4 | C/U | U | C |
| 5 | C/U | U | C |
| 7 | C/U | U | C |
| 8 | C/U | U | C |
| 9 | C/U | C | U |
| 11 | C/U | U | C |
| 14 | C/U | U | C |
| 15 | C/U | U | C |

Figure 1B:
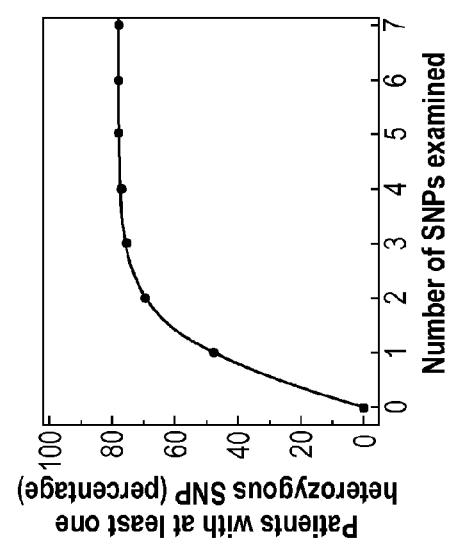

Eight other SNP sites were each heterozygous in >33% of the patient population studied in the instant invention but did not show a statistically significant association with HD. Because no particular isoform of these SNPs is associated with HD in the patient population, each SNP site requires two distinct, isoform-selective siRNAs. The maximum coverage (i.e., the number of patients with at least one heterozygous SNP site) was calculated for all possible combinations of one to seven SNPs. Adding two additional SNP sites covered ~75% of the patient population. Using four or more SNP sites as potential targets for siRNA therapy is not predicted to provide much additional benefit. Using even seven SNP sites achieves <80% coverage, but would require 13 isoform-selective siRNAs (FIG. 1B).

Example II

Development of Allele-Specific siRNAs

Figure 3A:
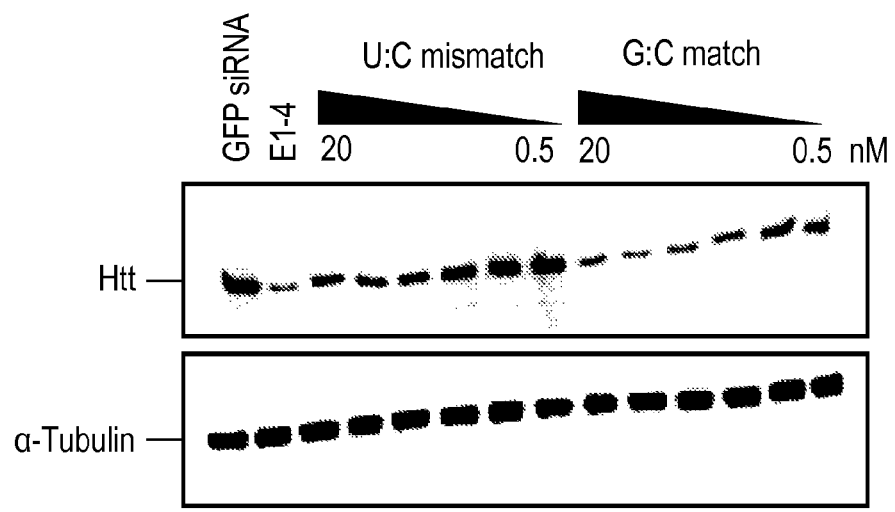
FIG. 3: A fully matched siRNA that reduces expression of both a luciferase reporter and endogenous Huntingtin mRNA causes a corresponding depletion of endogenous Huntingtin protein. An identical siRNA, but for a position 10 (P10) mismatch to the luciferase reporter and to the endogenous Huntingtin mRNA, was far less effective at suppressing Huntingtin protein production. HeLa cells were transfected with either the P10 match or P10 mismatch siRNA targeting SNP rs363125 at nt 5,304 of the Huntingtin mRNA, GFP siRNA alone, or a positive control siRNA targeting a non-polymorphic site in Exon 1 (E1-4) of the Huntingtin mRNA (DiFiglia et al., 2007). Cells were lysed 48 hours after transfection and analyzed by to Western blotting using antibodies to Huntingtin and α-Tubulin, which served as a loading control. (A) and (B) show independent replicates of the experiment.
Figure 3B:
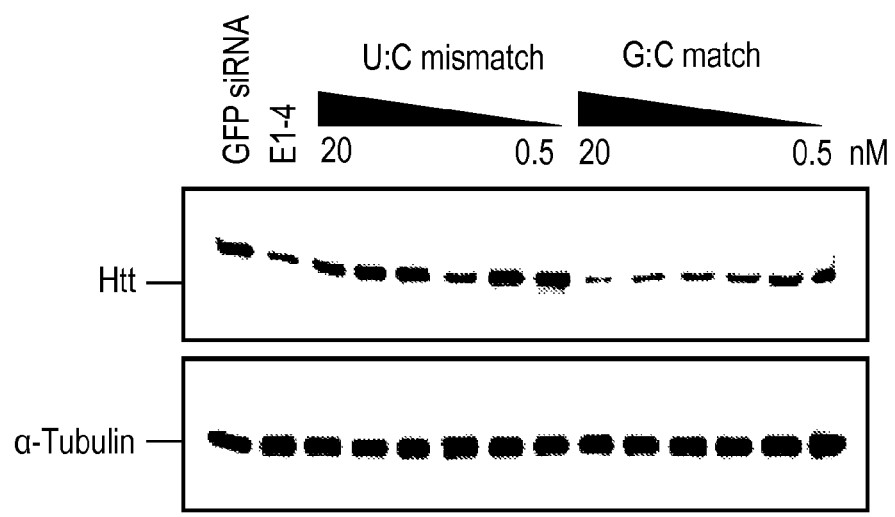
Figure 4A:
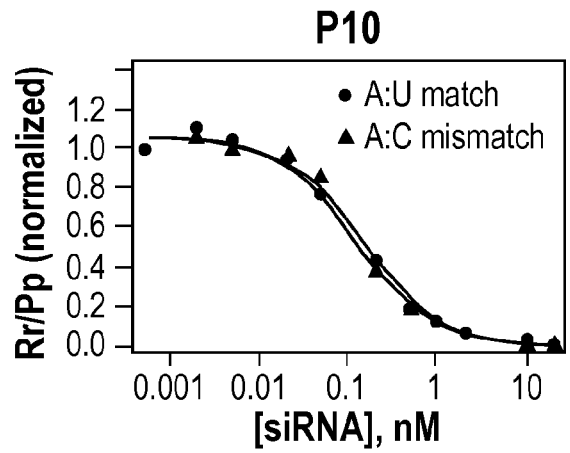
FIG. 4: Representative data for the development of an allele-specific siRNA-targeting SNP rs362307, which Is associated with HD. (A) siRNAs targeting the U isoform of rs362307 and mismatched to the C isoform at either position 10 or position 16 did not discriminate between matched and mismatched luciferase reporter mRNAs. (B) Placing an additional mismatch in the seed sequence of the siRNA bearing a position 10 mismatch to the C isoform improved its selective targeting of the U isoform. (C) A doubly mismatched siRNA targeting the C isoform also distinguished between reporter mRNAs corresponding to the position 10 matched, C isoform and the position 10 mismatched, U isoform.
Figure 4A:
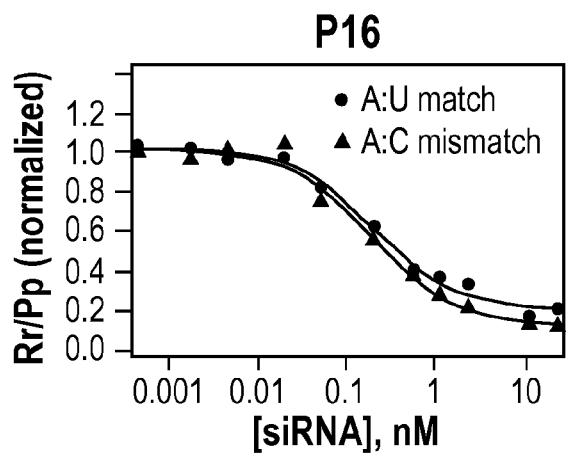
Figure 4B:
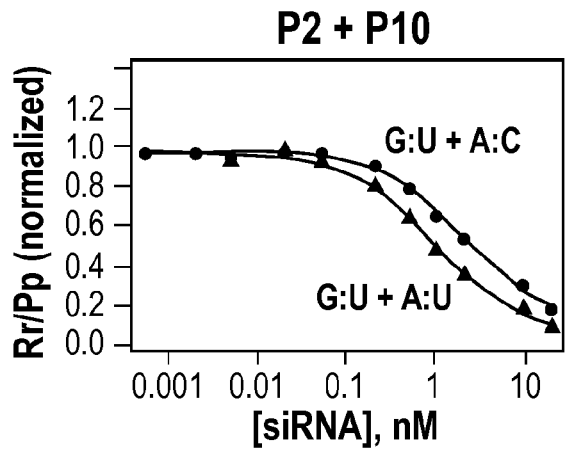
Figure 4B:
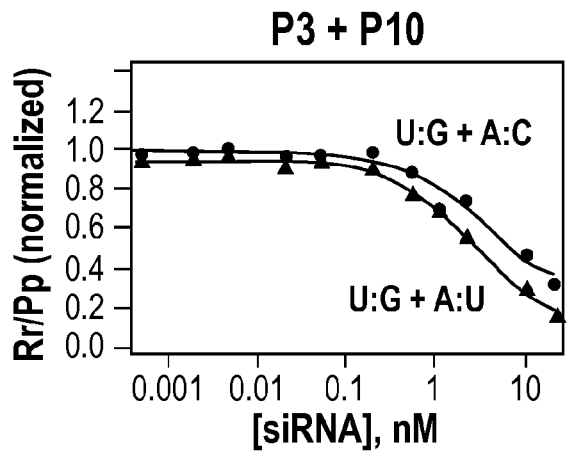
Figure 4B:
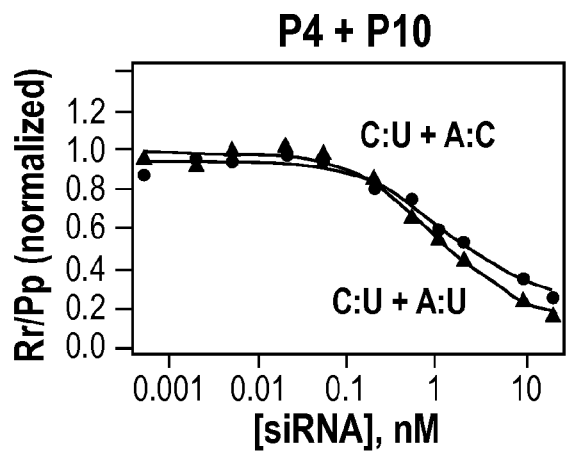
Figure 4B:
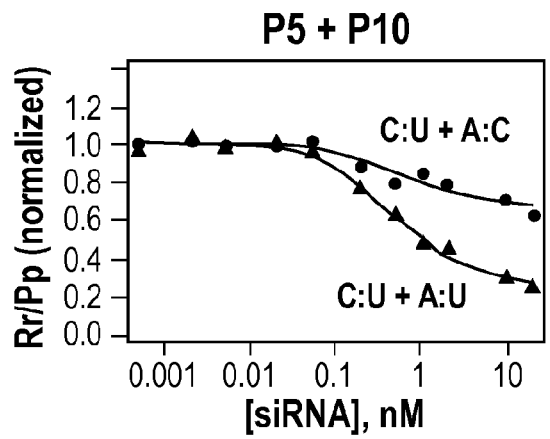
Figure 4B:
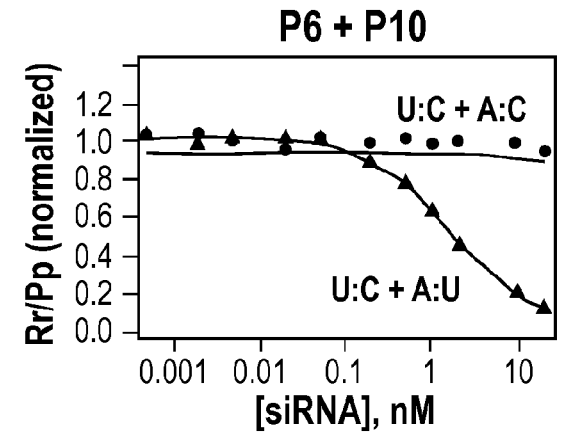
Figure 4B:
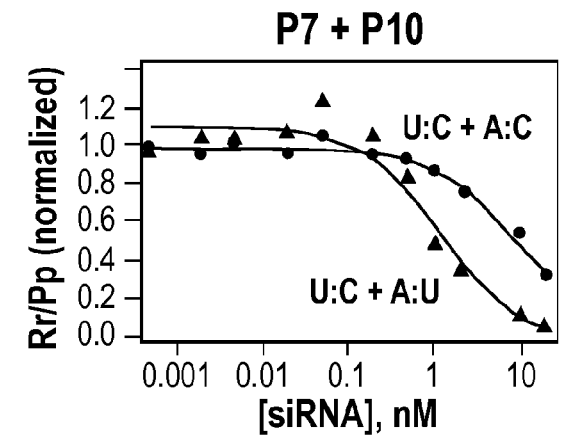

The HD-associated SNP site at position 9,633 of the Huntingtin mRNA does not fall into the category of SNPs that are predicted to be readily amenable to selective targeting because it does not create a purine:purine mismatch between siRNA and mRNA (Schwartz et al., 2006; Dykxhoorn et al., 2006). However, the analysis of Huntingtin SNPs in HD patients and controls in the instant invention (FIG. 1B and Table 1) suggests that a practicable RNA-silencing therapy for HD requires an siRNA that targets the disease isoform at this site but spares the normal Huntingtin mRNA. To this end, siRNAs targeting the U isoform of the position 9,633 SNP were designed. Both the efficacy and selectivity of the siRNAs were tested in cultured human HeLa cells co-transfected with the siRNA and luciferase reporters containing in their 3' UTRs either the U or C isoform of the sequence containing the SNP. In this invention, such luciferase reporter assays are good predictors of the efficacy and selectivity of siRNAs for endogenous mRNA targets. FIGS. 2 and 3 present an example with a pair of siRNAs—one fully matched and one bearing a position 10 (P10) mismatch—that targets an SNP site (rs363125) in endogenous Huntingtin mRNA in HeLa cells. Previous work has shown that such SNP-selective siRNAs can reduce mutant Huntingtin levels while leaving normal Huntingtin intact (van Bilsen et al., 2008).

siRNAs whose guide strand was fully matched to the U isoform, which is associated with HD but mismatched at position 10 or position 16 to the C isoform, were functional but failed to discriminate between U and C reporter mRNAs (FIG. 4A). (siRNAs that bear purine:pyrimidine mismatches to their counterselected targets generally show poor discrimination (Schwarz et al., 2006). Single mismatches at positions 2 through 9 (Table 5) were also tested but found that all of these were less specific than the most selective position 10+seed mismatch. Double-mismatch strategies based on a position 16 mismatch with the counter-selected isoform had very low activity (Table 5).

singly mismatched siRNA to retain silencing activity for the disease allele. Therefore, doubly mismatched siRNAs were tested combining a seed mismatch with a position 10 mismatch. Specifically, siRNAs predicted to mismatch at position 10 were prepared with the normal Huntingtin mRNA and also bearing an additional mismatch to both normal and disease alleles at one of the six seed positions (2-7). Mismatches at positions 5 or 6, combined with a position 10 mismatch with the counter-selected isoform, resulted in a reduction or loss of silencing of the SNP-mismatched target while retaining good activity against the SNP-matched target (FIG. 4B).

Table 2 reports "discrimination ratios"—the ratio of the IC50 of the siRNA for the counter-selected target to the IC50 of the targeted mRNA. The P10 (SNP)+P5 siRNA ($IC_{50P10\ mismatch}$>20; $IC_{50P10\ match}$=0.62±0.43 nM) had a discrimination ratio>32 and, at 20 nM, the highest concentration

TABLE 5

Validation of siRNAs designed to discriminate between isoforms of the rs362037 SNP

| siRNA guide strand | SEQ ID NO | SNP position | primary mismatch | secondary mismatch position | secondary mismatch | IC50 (nM) Match | IC50 (nM) Mismatch | Discrimination ratio |
|---|---|---|---|---|---|---|---|---|
| 5'-uacagacuuccaaaggcuccg-3' | 188 | 2 | A:C | none | none | 0.30 ± 0.07 | 0.23 ± 0.04 | 0.77 |
| 5'-ucacagacuuccaaaggcucc-3' | 189 | 3 | A:C | none | none | 0.52 ± 0.10 | 0.94 ± 0.62 | 1.8 |
| 5'-ugcacagacuuccaaaggcuc-3' | 190 | 4 | A:C | none | none | 0.88 ± 0.32 | 6.0 ± 3.7 | 6.8 |
| 5'-uggcacagacuuccaaaggcu-3' | 191 | 5 | A:C | none | none | 0.66 ± 0.32 | 1.8 ± 0.33 | 2.7 |
| 5'-ugggcacagacuuccaaaggc-3' | 192 | 6 | A:C | none | none | 0.93 ± 0.29 | 2.6 ± 0.89 | 2.8 |
| 5'-uagggcacagacuuccaaagg-3' | 193 | 7 | A:C | none | none | 0.45 ± 0.09 | 0.88 ± 0.49 | 1.9 |
| 5'-uaagggcacagacuuccaaag-3' | 194 | 8 | A:C | none | none | 0.36 ± 0.11 | 0.53 ± 0.12 | 1.5 |
| 5'-ucaagggcacagacuuccaaa-3' | 195 | 9 | A:C | none | none | 1.07 ± 0.06 | 0.93 ± 0.27 | 1.2 |
| 5'-uggcacaagggcacagacuuc-3' | 196 | 13 | A:C | none | none | 0.25 ± 0.10 | 0.42 ± 0.11 | 1.7 |
| 5'-guagggcacaagggcacagac-3' | 197 | 16 | A:C | 2 | U:G | 3.5 ± 2.9 | >20 | >5.7 |
| 5'-gccgggcacaagggcacagac-3' | 198 | 16 | A:C | 3 | C:U | >20 | >20 | ~1 |
| 5'-gcauggcacaagggcacagac-3' | 199 | 16 | A:C | 4 | U:C | >20 | >20 | ~1 |
| 5'-gcagugcacaagggcacagac-3' | 200 | 16 | A:C | 5 | U:C | 18 ± 8 | >20 | >1.1 |
| 5'-gcaggucacaagggcacagac-3' | 201 | 16 | A:C | 6 | U:C | 7.8 ± 5.5 | >20 | >2.6 |
| 5'-gcaggguacaagggcacagac-3' | 202 | 16 | A:C | 7 | U:G | 0.74 ± 0.08 | 9.4 ± 3.9 | 12.7 |
| 5'-gcagggcacaagggaacagac-3' | 203 | 16 | A:C | 15 | A:G | >20 | >20 | ~1 |
| 5'-gcagggcacaaggguacagac-3' | 204 | 16 | A:C | 15 | U:G | >20 | >20 | ~1 |
| 5'-gcagggcacaagggcauagac-3' | 205 | 16 | A:C | 17 | U:G | 1.0 ± 0.12 | 5.1 ± 0.67 | 5.1 |
| 5'-gcagggcacaagggcaaagac-3' | 206 | 16 | A:C | 17 | A:G | >20 | >20 | ~1 |
| 5'-cagggcacaagggcuuagacu-3' | 207 | 15 | A:C | 16 | U:G | 0.38 ± 0.02 | 0.64 ± 0.06 | 1.7 |

The IC50 is reported as >20 nM for siRNAs that failed to achieve half maximal inhibition at the highest concentration tested.

Figure 4C:
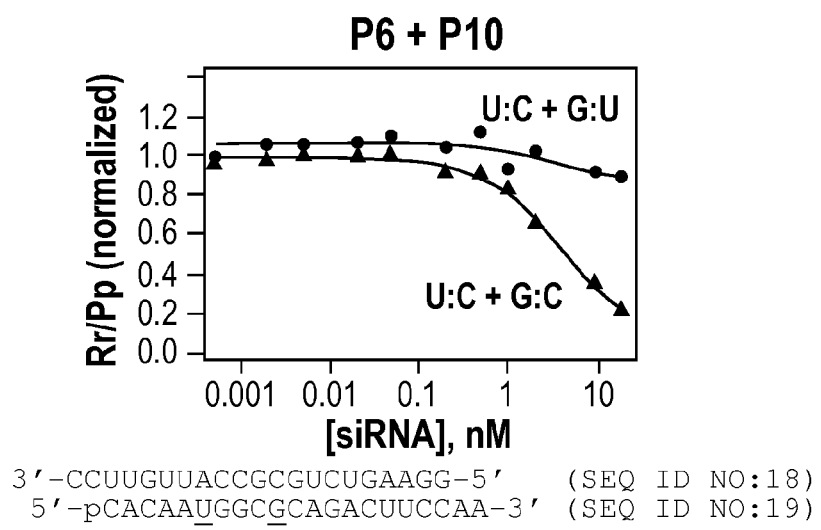

Previous work has shown that adding a second mismatch can improve the ability of siRNA to discriminate between alleles (Ohnishi et al., 2008). It was reasoned that adding a mismatch in the seed sequence of the siRNA might sufficiently destabilize the siRNA so that the doubly mismatched siRNA would lose its ability to silence the wild-type Huntingtin mRNA, and pairing at the SNP site would allow the tested, reduced expression of the counter-selected reporter by only 33%. The P10+P6 siRNA achieved no appreciable reduction in expression of the mismatched reporter, even at 20 nM ($IC_{50P10\ mismatch}$>20 nM), but was less effective against the matched reporter ($IC_{50P10\ match}$=1.5±0.31 nM), yielding a lower discrimination ratio. Such a trade-off was often observed between the efficacy and the selectivity of SNP-specific siRNAs. An siRNA targeting the C isoform was also designed and tested. Although it was less active than the siRNA targeting the U isoform, it selectively targeted the P10-matched allele ($IC_{50P10\ mismatch}>20$; $IC_{50P10\ match}=3.2\pm2.2$ nM; FIG. 4C and Table 6).

isoform of the SNP while minimizing silencing of the other isoform was tested. For the SNP site rs363125, which lies at nt 5,304 (exon 39) and occurs as either an A or a C, a single mismatch was sufficient to provide a high degree of selectivity for the fully matched target for both the A (>27-fold

TABLE 6

Validation of siRNAs designed to distinguish between matched and mismatched SNP isoforms.

| Reference Number | siRNA guide strand | SEQ ID NO | SNP position | primary mismatch | secondary mismatch position | secondary mismatch | IC50 (nM) Match | IC50 (nM) Mismatch | Discrimination ratio |
|---|---|---|---|---|---|---|---|---|---|
| rs363125 | 5'-agcguugaaguacugucccca-3' | 208 | 10 | G:A | none | none | 0.17 ± 0.11 | 0.27 ± 0.25 | 1.6 |
| rs363125 | 5'-agcguugaauuacugucccca-3' | 209 | 10 | U:C | none | none | 0.18 ± 0.09 | 0.22 ± 0.07 | 1.2 |
| rs363125 | 5'-ucuucuagcguugaaguacug-3' | 210 | 16 | G:A | none | none | 0.36 ± 0.24 | >20 | >55 |
| rs363125 | 5'-ucuucuagcguugaauuacug-3' | 211 | 16 | U:C | none | none | 0.74 ± 0.40 | >20 | >27 |
| rs362307 | 5'-cacaagggcgcagacuuccaa-3' | 212 | 10 | G:U | none | none | 0.36 ± 0.04 | 0.77 ± 0.16 | 2.1 |
| rs362307 | 5'-uacaagggcacagacuuccaa-3' | 213 | 10 | A:C | none | none | 0.16 ± 0.09 | 0.14 ± 0.10 | 0.87 |
| rs362307 | 5'-gcagggcacaagggcgcagac-3' | 214 | 16 | G:U | none | none | 0.73 ± 0.12 | 0.72 ± 0.12 | 0.99 |
| rs362307 | 5'-ucagggcacaagggcacagac-3' | 215 | 16 | A:C | none | none | 0.19 ± 0.02 | 0.20 ± 0.06 | 1.1 |
| rs362307 | 5'-cgcaagggcacagacuuccaa-3' | 216 | 10 | A:C | 2 | G:U | 1.0 ± 0.35 | 1.9 ± 0.27 | 1.9 |
| rs362307 | 5'-cauaagggcacagacuuccaa-3' | 217 | 10 | A:C | 3 | U:G | 3.0 ± 1.8 | 3.5 ± 1.6 | 1.2 |
| rs362307 | 5'-caccagggcacagacuuccaa-3' | 218 | 10 | A:C | 4 | C:U | 1.0 ± 0.22 | 1.6 ± 1.2 | 1.6 |
| rs362307 | 5'-cacacgggcacagacuuccaa-3' | 219 | 10 | A:C | 5 | C:U | 0.62 ± 0.43 | >20 | >32 |
| rs362307 | 5'-cacaauggcacagacuuccaa-3' | 220 | 10 | A:C | 6 | U:C | 1.5 ± 0.31 | >20 | >13 |
| rs362307 | 5'-cacaagugcacagacuuccaa-3' | 221 | 10 | A:C | 7 | U:C | 1.3 ± 0.51 | 5.9 ± 1.9 | 4.5 |
| rs362307 | 5'-cacaauggcgcagacuuccaa-3' | 222 | 10 | G:U | 6 | U:C | 3.2 ± 2.2 | >20 | >6 |
| rs362273 | 5'-guugaucuguagcagcagcuu-3' | 223 | 10 | U:G | none | none | 0.09 ± 0.14 | 0.01 ± 0.006 | 0.11 |
| rs362273 | 5'-guugaucugcagcagcagcuu-3' | 224 | 10 | C:A | none | none | 0.12 ± 0.06 | 0.44 ± 0.11 | 3.7 |
| rs362273 | 5'-cucggggungaucuguagcag-3' | 225 | 16 | U:G | none | none | 0.01 ± 0.002 | 0.007 ± 0.002 | 0.70 |
| rs362273 | 5'-cucggggungaucugcagcag-3' | 226 | 16 | C:A | none | none | 0.01 ± 0.003 | 0.004 ± 0.001 | 0.41 |
| rs362273 | 5'-ucugaucuguagcagcagcuu-3' | 227 | 10 | U:G | 2 | C:A | 0.01 ± 0.002 | 0.06 ± 0.008 | 5.9 |
| rs362273 | 5'-uucgaucuguagcagcagcuu-3' | 228 | 10 | U:G | 3 | C:A | 0.02 ± 0.003 | 0.29 ± 0.04 | 15 |
| rs362273 | 5'-uuuuaucuguagcagcagcuu-3' | 229 | 10 | U:G | 4 | U:C | 0.03 ± 0.006 | 0.37 ± 0.11 | 11 |
| rs362273 | 5'-uuugcucuguagcagcagcuu-3' | 230 | 10 | U:G | 5 | C:U | 0.02 ± 0.003 | 0.59 ± 0.08 | 31 |
| rs362273 | 5'-uuugaccuguagcagcagcuu-3' | 231 | 10 | U:G | 6 | C:A | 0.02 ± 0.002 | 0.06 ± 0.015 | 2.7 |
| rs362273 | 5'-uuugauuuguagcagcagcuu-3' | 232 | 10 | U:G | 7 | U:G | 0.006 ± 0.001 | 0.10 ± 0.02 | 17 |
| rs362273 | 5'-uuugcucugcagcagcagcuu-3' | 233 | 10 | C:A | 5 | C:U | 0.15 ± 0.04 | 0.74 ± 0.11 | 4.9 |

IC50 values are given as the average ± standard deviation for at least three independent experiments. The IC50 is reported as >20 nM for siRNAs that failed to achieve half-maximal inhibition at the highest concentration tested.

Figure 5A:
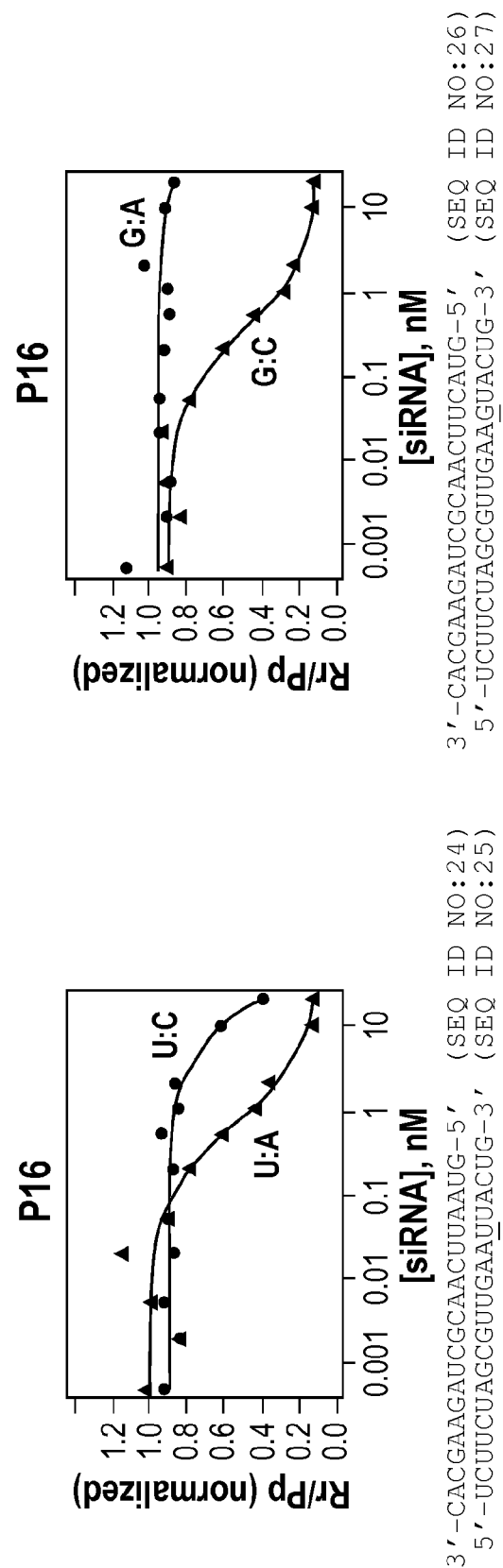
FIG. 5: Representative data for the development of isoform-specific siRNAs targeting two additional SNP sites. (A) siRNAs mismatched at position 16 discriminated between luciferase reporter mRNAs bearing either the C or the A isoform of the rs363125 SNP site. (B) siRNAs bearing a mismatch to the SNP site at position 10 and an additional position 5 mismatch discriminated between the G and A isoforms of the rs362273 SNP site.
Figure 5B:
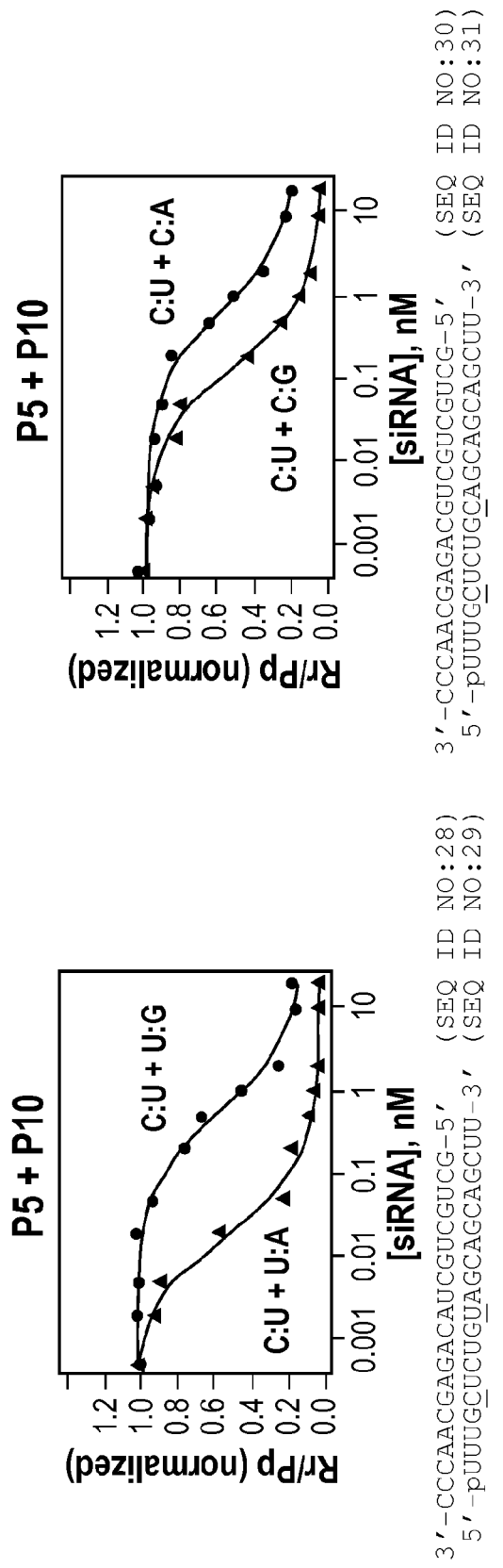
Figure 6A:
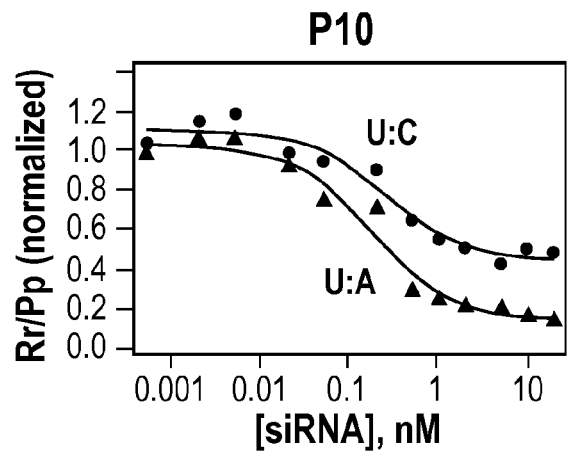
FIG. 6: Representative data for the dsiRNAs targeting the rs363125 SNP Site. siRNAs bearing a mismatch at position 10 to the C isoform (A) or the A isoform (B) of rs363125 did not discriminate well between matched and mismatched targets.
Figure 6B:
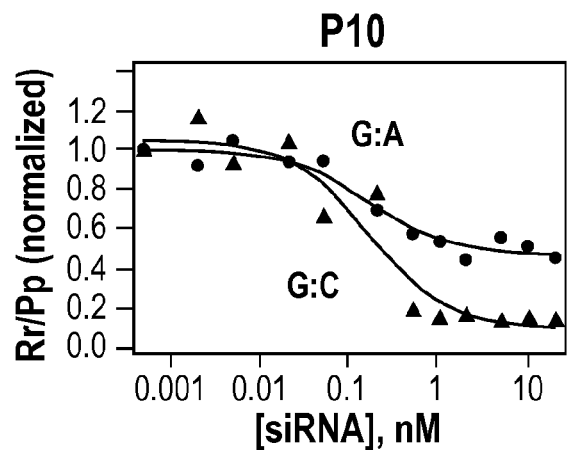
Figure 7:
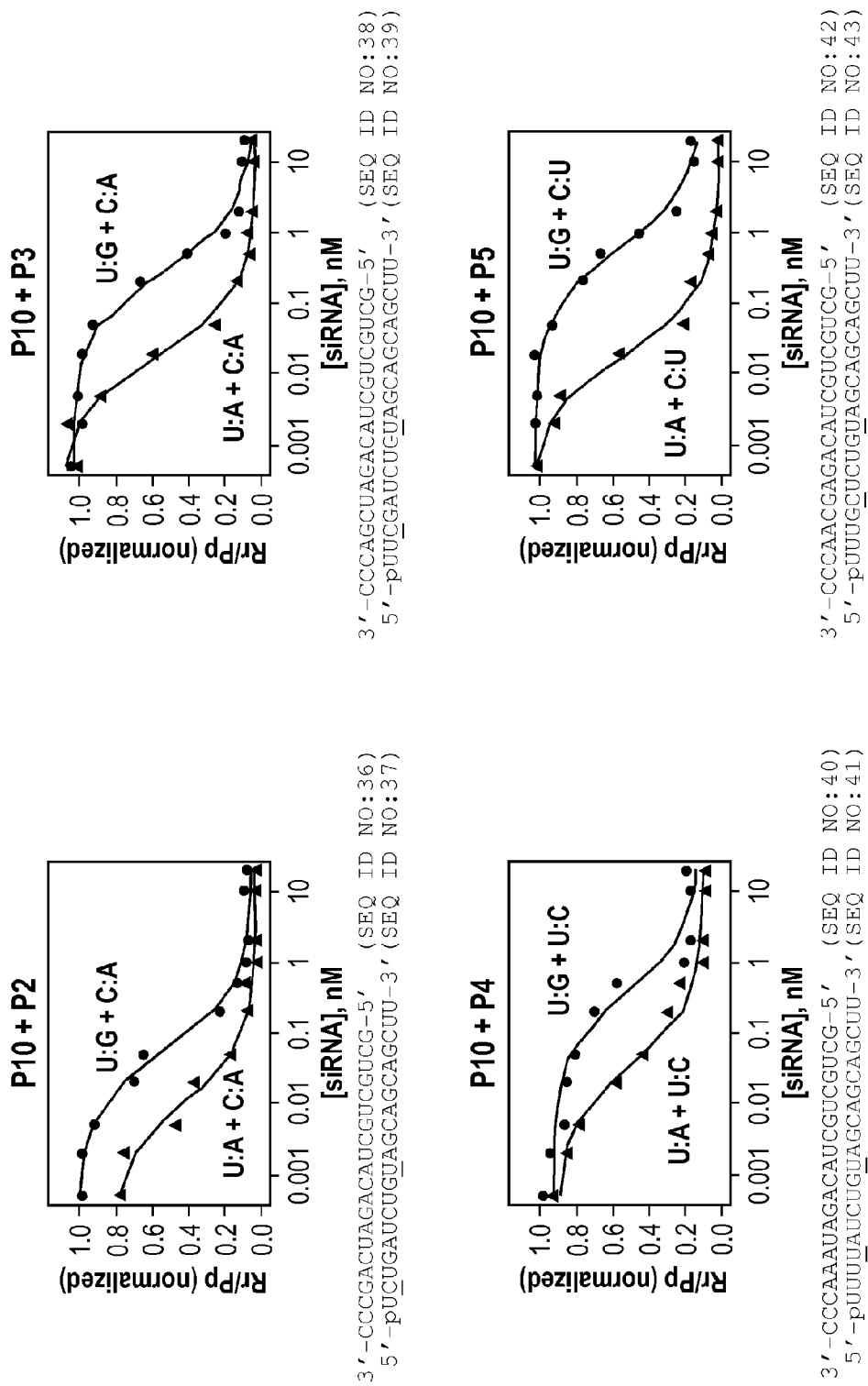
FIG. 7: Adding a position 5 mismatch to a position 10 mismatch increased the ability of an siRNA to discriminate between the two isoforms of the rs362273 SNP. The efficacy and selectivity of siRNAs combining mismatches at positions 2, 3, 4, 5, 6, or 7 with a mismatch at position 10 were evaluated. The position 10+position 5 siRNA was best able to distinguish between the matched and mismatched reporters. Representative data are shown.
Figure 7:
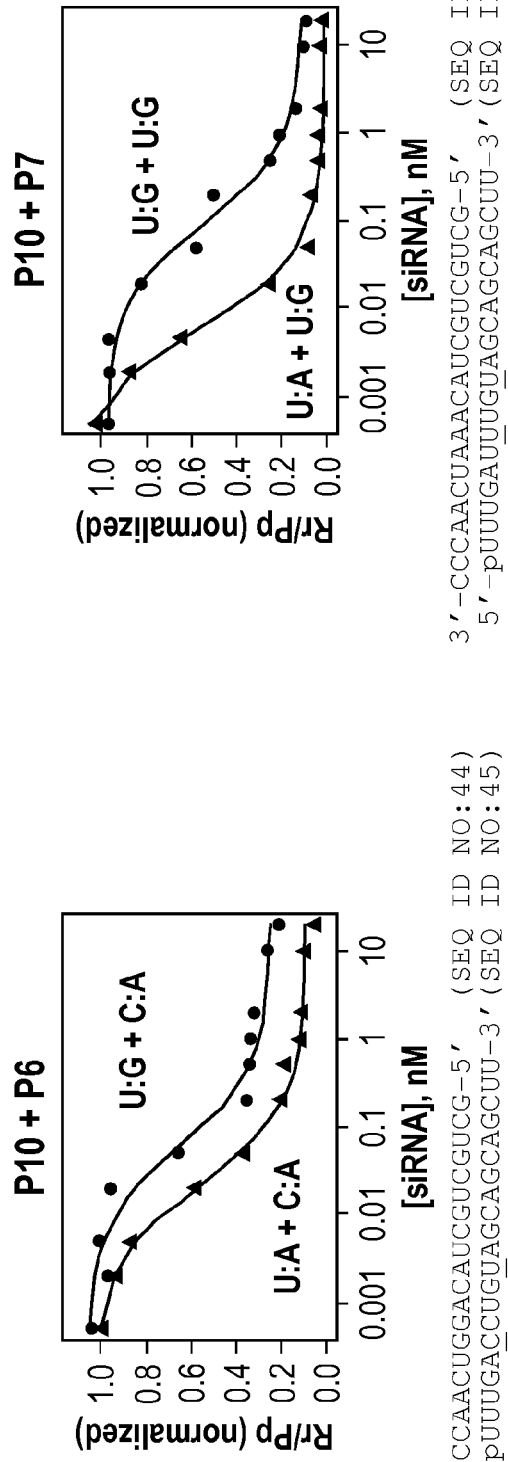

To cover 75% of HD patients requires siRNAs targeting additional SNPs. Because no specific nucleotide isoform of these SNP sites is associated with HD, selective siRNAs are needed for both isoforms. The instant invention also includes a strategy to screen patients to determine the SNP isoform associated with the expanded CAG repeat Huntingtin allele (Liu et al., 2008) and select the corresponding siRNA for therapy. As a first step, the ability of each siRNA to target one discrimination; $IC_{50mismatch}>20$ nM; $IC_{50match}=0.74\pm0.40$ nM) and C ($IC_{50mismatch}>20$ nM; >55-fold discrimination; $IC_{50match}=0.36\pm0.24$ nM) isoforms (FIGS. 5A and 6 and Table 6). For a second SNP, rs362273, which lies at nt 7,942 (exon 57) in the Huntingtin mRNA and occurs as either an A or a G, the P10 (SNP)+P5 siRNA design targeting the A isoform of the SNP provided ~30-fold selectivity ($IC_{50P10\ mismatch}=0.59\pm0.08$ nM; $IC_{50P10\ match}=0.02\pm0.003$ nM), whereas the siRNA targeting the G isoform (IC$_{50P10\ mismatch}$=0.74±0.11 nM; IC$_{50P10\ match}$=0.15±0.04 nM) gave ~4.9-fold selectivity (FIGS. 5B and 7 and Table 6).

Targeted reduction of mutant Huntingtin mRNA is considered an ideal strategy for treating HD. The primary obstacles to the development of such a therapy have been concerns about the number of siRNAs that would require testing in clinical trials. It is not clear whether drug regulatory agencies will permit patient-specific siRNAs to be used in humans without large-scale clinical trials. Such trials are, of course, not possible if only small numbers of patients share a common SNP isoform. The instant invention suggests that there is sufficient heterozygosity at a small number of SNP sites among American and European HD patients to support SNP-specific siRNA therapy. Targeting just three SNPs with five siRNAs is predicted to cover the majority of HD patients in the population studied here. This is possible because of the presence of several highly heterozygous SNPs and because a single SNP isoform for SNP rs362307 is associated with HD. One siRNA targeting this HD-associated isoform should target the mutant Huntingtin allele in nearly 50% of this exemplary patient population. This invention teaches the development of an siRNA that selectively targets the disease-associated isoform of this SNP in cultured human cells.

As for the ~25% of patients predicted to be beyond the reach of the five siRNAs developed here, the data presented herein predicts that a very large number of siRNAs will be required to provide siRNA therapy for this subpopulation. Adding an additional four siRNAs (for a total of nine siRNAs corresponding to five SNP sites) only increases the treatable patient population by 3%. A further increase in the number of siRNAs provides very little additional benefit.

By using potentiating mismatches in the seed sequence, isoform-selective siRNAs can be designed for SNP sites predicted to be poor candidates for the development of allele-selective siRNAs. This invention suggests that a single siRNA directed against a SNP isoform associated with HD could be used to treat nearly half the US and European HD population. Additional siRNAs directed against selected additional high frequency htt SNPs provides promising candidate therapies for HD.

Example III

Quantification of Mutant and Wild-Type Allelic htt mRNAs

Figure 8:
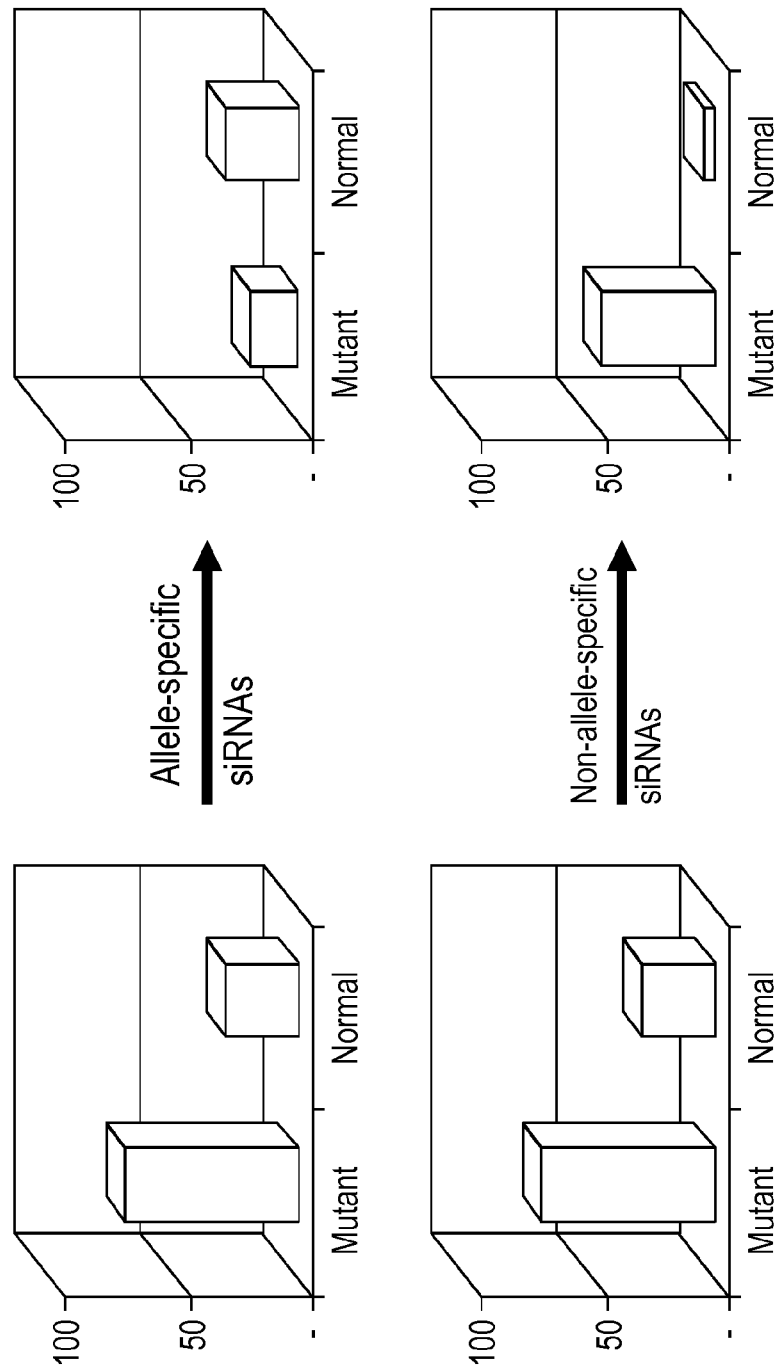
FIG. 8: Schematic of imbalanced huntingtin gene silencing versus allele-specific silencing.
Figure 9:
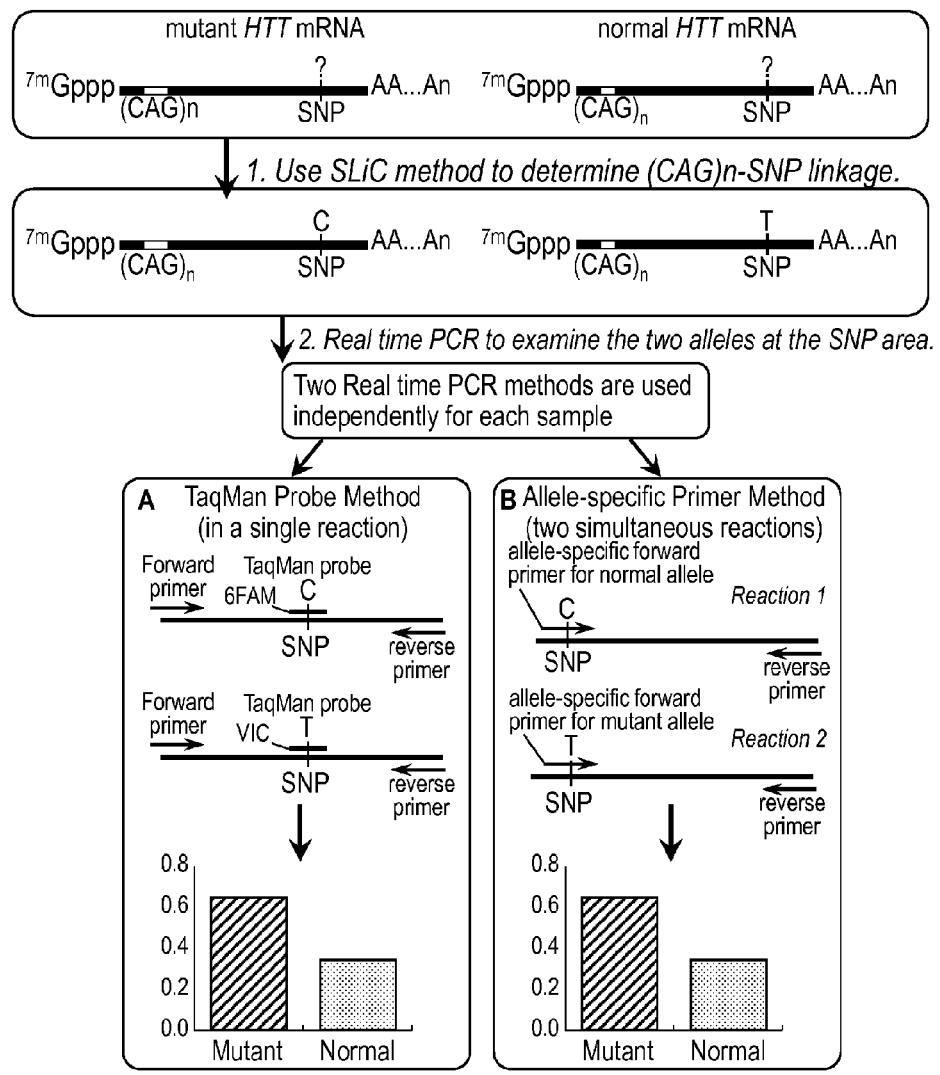
FIG. 9: Schematic illustrating a method for quantifying mutant and wild type huntingtin allelic mRNA.

In the event that the mutant htt allele is more abundant than the wild type htt allele in cells of HD patients, indiscriminant silencing could in theory eliminate the wild type htt allele while preserving the mutant htt allele, thereby actually exacerbating the disease. This possibility is illustrated in FIG. 8. Accordingly, levels of the mutant htt allele and the wild type htt allele were quantified in samples of mRNA obtained from human cortex of HD patients and control brain using the SLiC(SNP linkage by circularization) method and the TaqMan method, as illustrated in FIG. 9.

Figure 10:
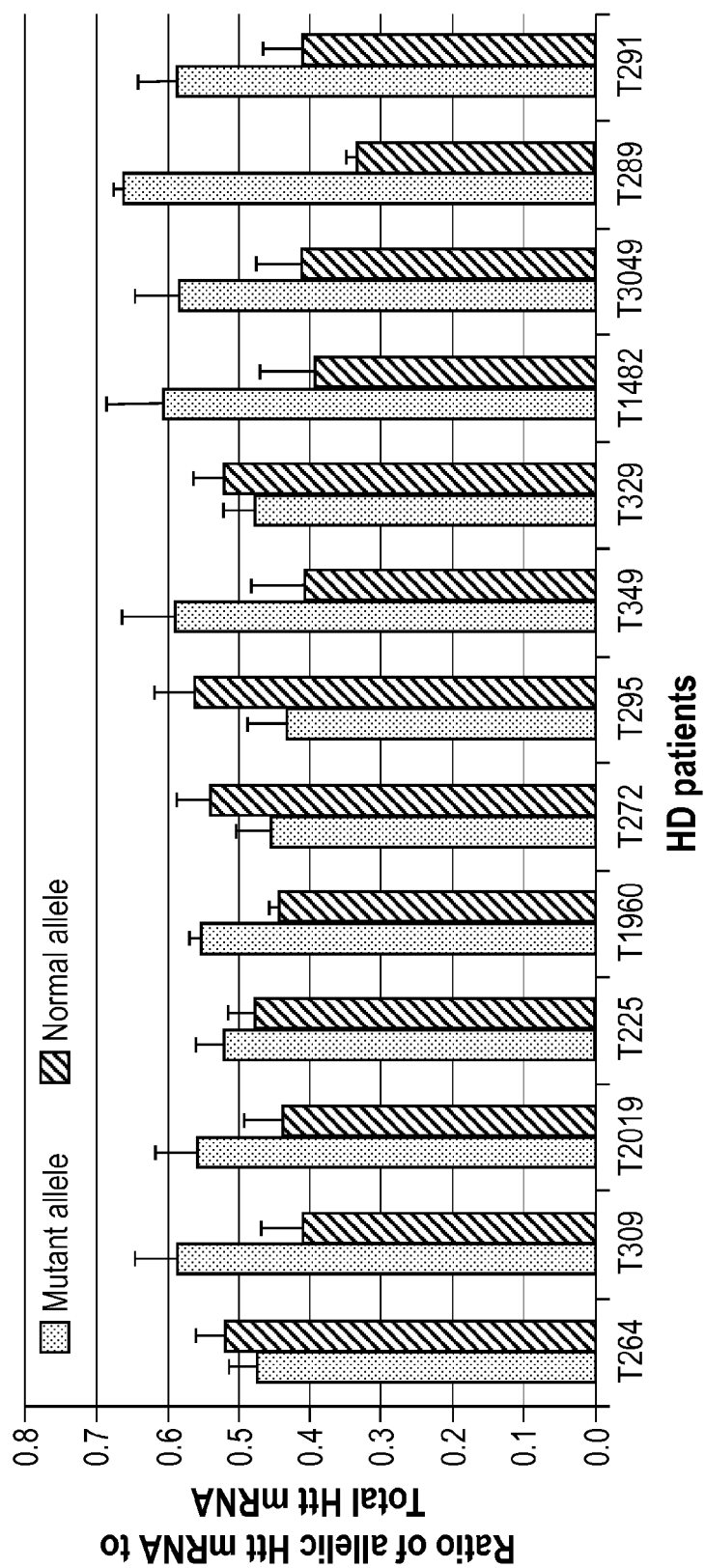
FIG. 10: Representative data indicating that mRNA corresponding to the mutant htt allele is more abundant than mRNA corresponding to the wild type htt allele in human cortex.
Figure 11:
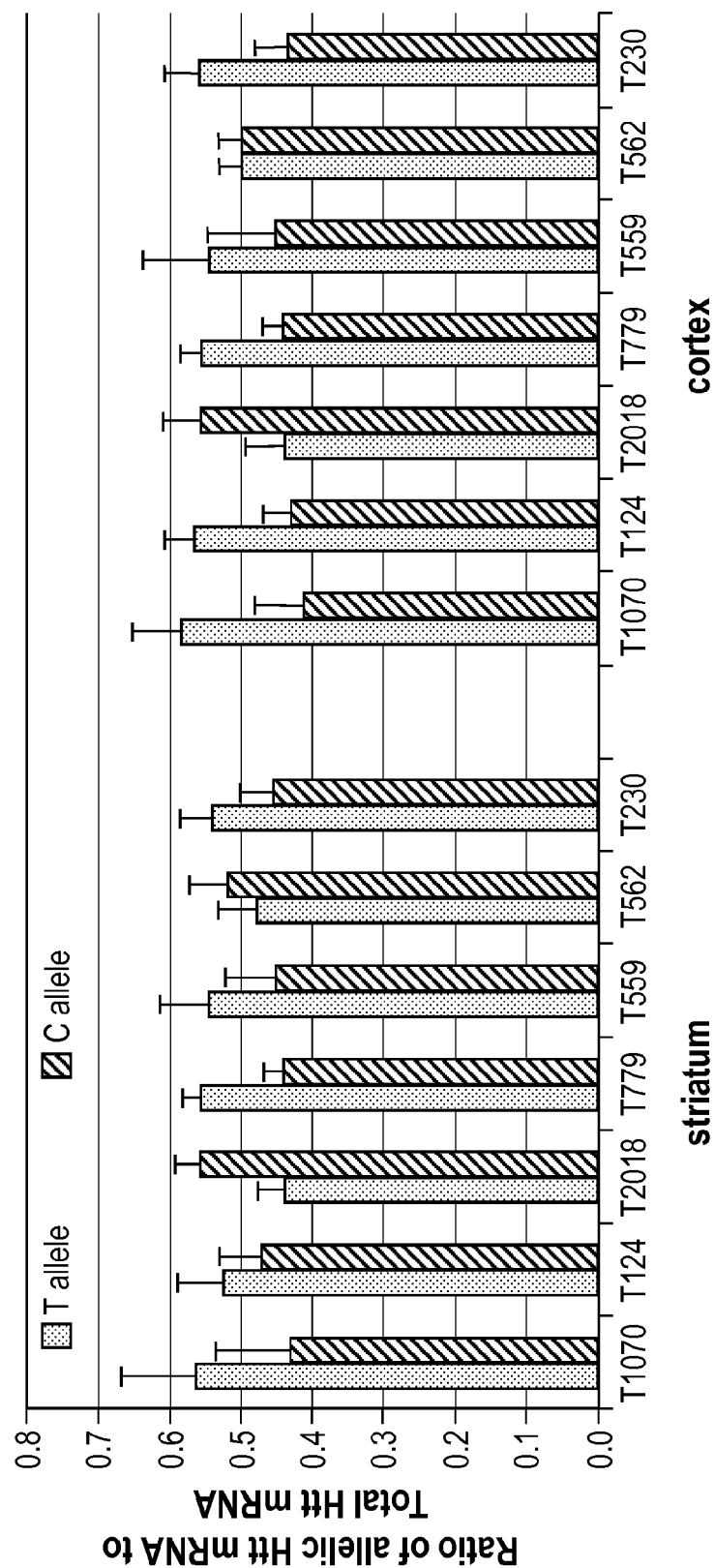
FIG. 11: Representative data showing the tentative association between SNP heterozygosity and huntingtin mRNA measurements in control brain.

As shown in FIG. 10, mRNA corresponding to the mutant htt allele is more abundant than mRNA corresponding to the wild type allele in the majority of subjects sampled. mRNA was obtained from the cortex of 13 individuals (T264-T291). This finding implies that non-selective htt knockdown could decrease wild type htt mRNA to a greater extent than mutant htt mRNA (where the siRNA is operational on a molar basis), potentially worsening the symptoms of HD. This highlights the importance of allele-specific approaches for silencing the mutant htt allele while maintaining wild type htt expression.

SELECTED REFERENCES

Xia H., Mao Q., Eliason S. L., Harper S. Q., Martins I. H., Orr H. T., Paulson H. L., Yang L., Kotin R. M., and Davidson B. L. (2004). RNAi suppresses polyglutamine-induced neurodegeneration in a model of spinocerebellar ataxia. Nat. Med. 10, 816-820.

Machida Y., Okada T., Kurosawa M., Oyama F., Ozawa K., and Nukina N. (2006). rAAV-mediated shRNA ameliorated neuropathology in Huntington disease model mouse. Biochem Biophys Res Commun. 343, 190-197.

Wang Y. L., Liu W., Wada E., Murata M., Wada K., and Kanazawa I. (2005). Clinico-pathological rescue of a model mouse of Huntington's disease by siRNA. Neurosci Res. 53, 241-249.

Xia X., Zhou H., Huang Y., and Xu Z. (2006). Allele-specific RNAi selectively silences mutant SOD1 and achieves significant therapeutic benefit in vivo. Neurobiol Dis. 23, 578-586.

Xia H., Mao Q., Paulson H. L., and Davidson B. L. (2002). siRNA-mediated gene silencing in vitro and in vivo. Nat. Biotechnol. 20, 1006-1010.

Harper S. Q., Staber P. D., He X., Eliason S. L., Martins I. H., Mao Q., Yang L., Kotin R. M., Paulson H. L., and Davidson B. L. (2005). RNA interference improves motor and neuropathological abnormalities in a Huntington's disease mouse model. Proc Natl Acad Sci USA. 102, 5820-5825.

Ralph G. S., Radcliffe P. A., Day D. M., Carthy J. M., Leroux M. A., Lee D. C., Wong L. F., Bilsland L. G., Greensmith L., Kingsman S. M. et al. (2005). Silencing mutant SOD1 using RNAi protects against neurodegeneration and extends survival in an ALS model. Nat. Med. 11, 429-433.

Raoul C., Abbas-Terki T., Bensadoun J. C., Guillot S., Haase G., Szulc J., Henderson C. E., and Aebischer P. (2005). Lentiviral-mediated silencing of SOD1 through RNA interference retards disease onset and progression in a mouse model of ALS. Nat. Med. 11, 423-428.

Group T.H.D.C.R. (1993). A novel gene containing a trinucleotide repeat that is expanded and unstable on Huntington's disease chromosomes. Cell. 72, 971-983.

Caplen N. J., Taylor J. P., Statham V. S., Tanaka F., Fire A., and Morgan R. A. (2002). Rescue of polyglutamine-mediated cytotoxicity by double-stranded RNA-mediated RNA interference. Hum Mol. Genet. 11, 175-184.

Schwarz D. S., Ding H., Kennington L., Moore J. T., Schelter J., Burchard J., Linsley P. S., Aronin N., Xu Z., and Zamore P. D. (2006). Designing siRNA That Distinguish between Genes That Differ by a Single Nucleotide. PLoS Genet. 2, 1307-1318.

Ding H., Schwarz D. S., Keene A., Affar el B., Fenton L., Xia X., Shi Y., Zamore P. D., and Xu Z. (2003). Selective silencing by RNAi of a dominant allele that causes amyotrophic lateral sclerosis. Aging Cell. 2, 209-217.

Dahlgren C., Zhang H. Y., Du Q., Grahn M., Norstedt G., Wahlestedt C., and Liang Z. (2008). Analysis of siRNA specificity on targets with double-nucleotide mismatches. Nucleic Acids Res.

Du Q., Thonberg H., Wang J., Wahlestedt C., and Liang Z. (2005). A systematic analysis of the silencing effects of an active siRNA at all single-nucleotide mismatched target sites. Nucleic Acids Res. 33, 1671-1677.

Miller V. M., Gouvion C. M., Davidson B. L., and Paulson H. L. (2004). Targeting Alzheimer's disease genes with RNA interference: an efficient strategy for silencing mutant alleles. Nucleic Acids Res. 32, 661-668.

Auerbach W., Hurlbert M. S., Hilditch-Maguire P., Wadghiri Y. Z., Wheeler V. C., Cohen S. I., Joyner A. L., MacDonald M. E., and Turnbull D. H. (2001). The HD mutation causes progressive lethal neurological disease in mice expressing reduced levels of huntingtin. Hum Mol. Genet. 10, 2515-2523.

Cattaneo E., Zuccato C., and Tartari M. (2005). Normal huntingtin function: an alternative approach to Huntington's disease. Nat Rev Neurosci. 6, 919-930.

Dragatsis I., Levine M. S., and Zeitlin S. (2000). Inactivation of Hdh in the brain and testis results in progressive neurodegeneration and sterility in mice. Nat. Genet. 26, 300-306.

Dykxhoorn D. M., Schlehuber L. D., London I. M., and Lieberman J. (2006). Determinants of specific RNA interference-mediated silencing of human beta-globin alleles differing by a single nucleotide polymorphism. Proc Natl Acad Sci USA. 103, 5953-5958.

Riva A., and Kohane I. S. (2004). A SNP-centric database for the investigation of the human genome. BMC Bioinformatics. 5, 33.

Riva A., and Kohane I. S. (2002). SNPper: retrieval and analysis of human SNPs. Bioinformatics. 18, 1681-1685.

Liu W., Kennington L. A., Rosas H. D., Hersch S., Cha J. H., Zamore P. D., and Aronin N. (2008). Linking SNPs to CAG repeat length in Huntington's disease patients. Nat Methods. 5, 951-953.

van Bilsen P. H., Jaspers L., Lombardi M. S., Odekerken J. C., Burright E. N., and Kaemmerer W. F. (2008). Identification and allele-specific silencing of the mutant huntingtin allele in Huntington's disease patient-derived fibroblasts. Hum Gene Ther. 19, 710-719.

Ohnishi Y., Tamura Y., Yoshida M., Tokunaga K., and Hohjoh H. (2008). Enhancement of allele discrimination by introduction of nucleotide mismatches into siRNA in allele-specific gene silencing by RNAi. PLoS ONE. 3, e2248.

Barrett J. C., Fry B., Mailer J., and Daly M. J. (2005). Haploview: analysis and visualization of LD and haplotype maps. Bioinformatics. 21, 263-265.

DiFiglia M., Sapp E., Chase K., Schwarz C., Meloni A., Young C., Martin E., Vonsattel J. P., Carraway R., Reeves S. A. et al. (1995). Huntingtin is a cytoplasmic protein associated with vesicles in human and rat brain neurons. Neuron. 14, 1075-1081.

Livak K. J., and Schmittgen T. D. (2001). Analysis of relative gene expression data using real-time quantitative PCR and the 2(-Delta Delta C(T)) Method. Methods. 25, 402-408.

DiFiglia M., Sena-Esteves M., Chase K., Sapp E., Pfister E., Sass M., Yoder J., Reeves P., Pandey R. K., Rajeev K. G. et al. (2007). Therapeutic silencing of mutant huntingtin with siRNA attenuates striatal and cortical neuropathology and behavioral deficits. Proc Natl Acad Sci USA. 104, 17204-17209.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of silencing mutant huntingtin (htt) mRNA in a HD patient population, comprising administering to said patient population an effective amount of a first RNA silencing agent targeting a HD-associated htt single nucleotide polymorphism (SNP) in combination with one or more RNA silencing agents targeting one or more other htt SNPs, such that RNA silencing of said mRNA occurs, wherein the HD-associated htt SNP is the U isoform of rs362307, and wherein at least one other htt SNP has a frequency of heterozygosity of at least 20% or more in a sample population.

2. The method of claim 1, wherein the other htt SNPs are as set forth in Table 2.

3. The method of claim 1, wherein the htt SNP having a frequency of heterozygosity of at least 20% or more in a sample population is selected from the group consisting of rs4690074, rs362336, rs362331, rs362273, rs362272, rs362306, rs362268, and rs362267.

4. The method of claim 2, wherein the patient population is of US or Western European origin.

5. A method of silencing mutant htt mRNA in 70% or more HD patients in a HD patient population, comprising administering to said HD patient population a plurality of RNA silencing agents, wherein a first RNA silencing agent targets the U isoform of HD-associated SNP RS362307, a second RNA silencing agent targets a htt single nucleotide polymorphism (SNP) having a frequency of heterozygosity of at least 20% or more in a sample HD patient population, and a third RNA silencing agent targets a third htt SNP, such that RNA silencing of said mRNA occurs in 70% or more patients in the HD patient population.

6. The method of claim 1 or claim 5, further comprising identifying the sequence of the nucleotide located at one or more htt SNPs in the mutant htt mRNA of the HD patients in the HD patient population.

7. The method of claim 5, wherein the RNA silencing agents target SNP1, SNP2, and SNP3 as set forth in Table 2.

8. The method of claim 5, wherein the second RNA silencing agent targets rs362273.

9. The method of claim 1 or claim 5, wherein the RNA silencing agent is selected from the group consisting of a siRNA, a shRNA, or a vector encoding a shRNA.

10. The method of claim 1 or claim 5, wherein a nucleotide complementary to the SNP in the mutant htt mRNA is located at position 10 relative to the 5'end of the antisense strand of the RNA silencing agent.

11. The method of claim 10, wherein the RNA silencing agent further comprises a mismatch with respect to both the mutant htt mRNA and the wild-type htt mRNA at one or more positions located within the seed sequence of the RNA silencing agent.

12. The method of claim 11, wherein said one or more positions are selected from the group consisting of position 2, position 3, position 4, position 5, position 6, and position 7 relative to the 5' end of the antisense strand of the RNA silencing agent.

13. The method of claim 12, wherein said position is position 5.

14. The method of claim 12, wherein said position is position 6.

15. The method of claim 5, wherein the guide strand of the first RNA silencing agent comprises SEQ ID NO:220, wherein the guide strand of the second RNA silencing agent comprises SEQ ID NO:210 or SEQ ID NO:211, and wherein the guide strand of the third RNA silencing agent comprises SEQ ID NO:230 or SEQ ID NO:233.

16. The method of claim 5, wherein the guide strand of the first RNA silencing agent comprises SEQ ID NO:219, wherein the guide strand of the second RNA silencing agent comprises SEQ ID NO:210 or SEQ ID NO:211, and wherein the guide strand of the third RNA silencing agent comprises SEQ ID NO:230 or SEQ ID NO:233.

17. The method of claim 1, wherein the other htt SNP is RS362273.

18. The method of claim 5, wherein the second RNA silencing agent targets a htt SNP selected from the group consisting of rs4690074, rs362336, rs362331, rs362273, rs362272, rs362306, rs362268, and rs362267.

19. The method of claim 17, further comprising administering to said patient population an effective amount of an RNA silencing agent targeting rs363125.

20. The method of claim 8, wherein the third RNA silencing agent targets rs363125.

21. The method of claim 1 or claim 5, wherein the RNA silencing agent targeting the U isoform of rs362307 contains a guide strand comprising SEQ ID NO:219 or SEQ ID NO:220.

* * * * *

SEQUENCE LISTING

```
<160> NUMBER OF SEQ ID NOS: 233

<210> SEQ ID NO 1
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
gggacaguac uucaacgcga g                                                 21

<210> SEQ ID NO 2
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
agcguugaag uacugucccc a                                                 21

<210> SEQ ID NO 3
<211> LENGTH: 41
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 3
guuaagagau ggggacagua cuucaacgcu agaagaacac a                41

<210> SEQ ID NO 4
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
gggacaguaa uucaacgcga g                                     21

<210> SEQ ID NO 5
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
agcguugaau uacugucccc a                                     21

<210> SEQ ID NO 6
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6
ggaagucugu gcccuugucc c                                     21

<210> SEQ ID NO 7
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
uacaagggca cagacuucca a                                     21

<210> SEQ ID NO 8
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
ggaagucugu gcccuugcuc c                                     21

<210> SEQ ID NO 9
<211> LENGTH: 21
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
cgcaagggca cagacuucca a                                            21

<210> SEQ ID NO 10
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
ggaagucugu gcccuuauuc c                                            21

<210> SEQ ID NO 11
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
cauaagggca cagacuucca a                                            21

<210> SEQ ID NO 12
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
cugugcccuu gugcccugcc u                                            21

<210> SEQ ID NO 13
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
ucagggcaca agggcacaga c                                            21

<210> SEQ ID NO 14
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14
ggaagucugu gcccugguuc c                                            21
```

```
<210> SEQ ID NO 15
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
caccagggca cagacuucca a                                              21

<210> SEQ ID NO 16
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16
ggaagucugu gcccguguuc c                                              21

<210> SEQ ID NO 17
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
cacacgggca cagacuucca a                                              21

<210> SEQ ID NO 18
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 18
ggaagucugc gccauuguuc c                                              21

<210> SEQ ID NO 19
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19
cacaauggcg cagacuucca a                                              21

<210> SEQ ID NO 20
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

```
      Synthetic oligonucleotide"

<400> SEQUENCE: 20
ggaagucugu gccauuguuc c                                          21

<210> SEQ ID NO 21
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
cacaauggca cagacuucca a                                          21

<210> SEQ ID NO 22
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22
ggaagucugu gcacuuguuc c                                          21

<210> SEQ ID NO 23
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23
cacaagugca cagacuucca a                                          21

<210> SEQ ID NO 24
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24
guaauucaac gcuagaagca c                                          21

<210> SEQ ID NO 25
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
ucuucuagcg uugaauuacu g                                          21

<210> SEQ ID NO 26
<211> LENGTH: 21
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
guacuucaac gcuagaagca c                                              21

<210> SEQ ID NO 27
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
ucuucuagcg uugaaguacu g                                              21

<210> SEQ ID NO 28
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28
gcugcugcua cagagcaacc c                                              21

<210> SEQ ID NO 29
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 29
uuugcucugu agcagcagcu u                                              21

<210> SEQ ID NO 30
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 30
gcugcugcug cagagcaacc c                                              21

<210> SEQ ID NO 31
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 31
```
uuugcucugc agcagcagcu u                                             21

<210> SEQ ID NO 32
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 32
gggacaguaa uucaacgcga g                                             21

<210> SEQ ID NO 33
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 33
agcguugaau uacuguccccc a                                            21

<210> SEQ ID NO 34
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 34
gggacaguac uucaacgcga g                                             21

<210> SEQ ID NO 35
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 35
agcguugaag uacugucccc a                                             21

<210> SEQ ID NO 36
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 36
gcugcugcua cagaucagcc c                                             21

<210> SEQ ID NO 37
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 37
ucugaucugu agcagcagcu u                                              21

<210> SEQ ID NO 38
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 38
gcugcugcua cagaucgacc c                                              21

<210> SEQ ID NO 39
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39
uucgaucugu agcagcagcu u                                              21

<210> SEQ ID NO 40
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40
gcugcugcua cagauaaacc c                                              21

<210> SEQ ID NO 41
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41
uuuuaucugu agcagcagcu u                                              21

<210> SEQ ID NO 42
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 42
gcugcugcua cagagcaacc c                                              21

<210> SEQ ID NO 43

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 43
uuugcucugu agcagcagcu u                                              21

<210> SEQ ID NO 44
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 44
gcugcugcua caggucaacc c                                              21

<210> SEQ ID NO 45
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 45
uuugaccugu agcagcagcu u                                              21

<210> SEQ ID NO 46
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 46
gcugcugcua caaaucaacc c                                              21

<210> SEQ ID NO 47
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 47
uuugauuugu agcagcagcu u                                              21

<210> SEQ ID NO 48
<211> LENGTH: 13672
<212> TYPE: DNA
<213> ORGANISM: Homo sapiens

<400> SEQUENCE: 48
ttgctgtgtg aggcagaacc tgcgggggca ggggcgggct ggttccctgg ccagccattg     60
gcagagtccg caggctaggg ctgtcaatca tgctggccgg cgtggccccg cctccgccgg    120
```

-continued

```
cgcggccccg cctccgccgg cgcacgtctg ggacgcaagg cgccgtgggg gctgccggga      180
cgggtccaag atggacggcc gctcaggttc tgcttttacc tgcggcccag agccccattc      240
attgccccgg tgctgagcgg cgccgcgagt cggcccgagg cctccgggga ctgccgtgcc      300
gggcgggaga ccgccatggc gaccctggaa aagctgatga aggccttcga gtccctcaag      360
tccttccagc agcagcagca gcagcagcag cagcagcagc agcagcagca gcagcagcag      420
cagcagcagc aacagccgcc accgccgccg ccgccgccgc cgcctcctca gcttcctcag      480
ccgccgccgc aggcacagcc gctgctgcct cagccgcagc cgcccccgcc gccgccccg       540 ccgccacccg gccggctgt ggctgaggag ccgctgcacc gaccaaagaa agaactttca       600
gctaccaaga aagaccgtgt gaatcattgt ctgacaatat gtgaaaacat agtggcacag      660
tctgtcagaa attctccaga atttcagaaa cttctgggca tcgctatgga acttttctg      720 ctgtgcagtg atgacgcaga gtcagatgtc aggatggtgg ctgacgaatg cctcaacaaa      780
gttatcaaag cttttgatgga ttctaatctt ccaaggttac agctcgagct ctataaggaa      840
attaaaaaga atggtgcccc tcggagtttg cgtgctgccc tgtggaggtt tgctgagctg      900
gctcacctgg ttcggcctca gaaatgcagg ccttacctgg tgaaccttct gccgtgcctg      960
actcgaacaa gcaagagacc cgaagaatca gtccaggaga ccttggctgc agctgttccc     1020
aaaattatgg cttcttttgg caattttgca aatgacaatg aaattaaggt tttgttaaag     1080
gccttcatag cgaacctgaa gtcaagctcc cccaccattc ggcggacagc ggctggatca     1140
gcagtgagca tctgccagca ctcaagaagg acacaatatt tctatagttg gctactaaat     1200
gtgctcttag gcttactcgt tcctgtcgag gatgaacact ccactctgct gattcttggc     1260
gtgctgctca ccctgaggta tttggtgccc ttgctgcagc agcaggtcaa ggacacaagc     1320
ctgaaaggca gcttcggagt gacaaggaaa gaaatggaag tctctccttc tgcagagcag     1380
cttgtccagg tttatgaact gacgttacat catacacagc accaagacca caatgttgtg     1440
accggagccc tggagctgtt gcagcagctc ttcagaacgc ctccacccga gcttctgcaa     1500
accctgaccg cagtcggggg cattgggcag ctcaccgctg ctaaggagga gtctggtggc     1560
cgaagccgta gtgggagtat tgtggaactt atagctggag ggggttcctc atgcagccct     1620 gtccttttcaa gaaaacaaaa aggcaaagtg ctcttaggag aagaagaagc cttggaggat     1680
gactctgaat cgagatcgga tgtcagcagc tctgccttaa cagcctcagt gaaggatgag     1740
atcagtggag agctggctgc ttcttcaggg gtttccactc cagggtcagc aggtcatgac     1800
atcatcacag aacagccacg gtcacagcac acactgcagg cggactcagt ggatctggcc     1860
agctgtgact tgacaagctc tgccactgat ggggatgagg aggatatctt gagccacagc     1920
tccagccagg tcagcgccgt cccatctgac cctgccatgg acctgaatga tgggacccag     1980
gcctcgtcgc ccatcagcga cagctcccag accaccaccg aagggcctga ttcagctgtt     2040
accccttcag acagttctga aattgtgtta gacggtaccg acaaccagta tttgggcctg     2100
cagattggac agccccagga tgaagatgag gaagccacag gtattcttcc tgatgaagcc     2160
tcggaggcct tcaggaactc ttccatggcc cttcaacagg cacatttatt gaaaaacatg     2220
agtcactgca ggcagccttc tgacagcagt gttgataaat ttgtgttgag agatgaagct     2280
actgaaccgg gtgatcaaga aaacaagcct gccgcatca aggtgacat tggacagtcc      2340 actgatgatg actctgcacc tcttgtccat tgtgtccgcc ttttatctgc ttcgtttttg     2400
ctaacagggg gaaaaaatgt gctggttccg gacagggatg tgagggtcag cgtgaaggcc     2460
```

```
ctggccctca gctgtgtggg agcagctgtg gccctccacc cggaatcttt cttcagcaaa    2520
ctctataaag ttcctcttga caccacggaa taccctgagg aacagtatgt ctcagacatc    2580
ttgaactaca tcgatcatgg agacccacag gttcgaggag ccactgccat tctctgtggg    2640
accctcatct gctccatcct cagcaggtcc cgcttccacg tgggagattg gatgggcacc    2700
attagaaccc tcacaggaaa tacattttct ttggcggatt gcattccttt gctgcggaaa    2760
acactgaagg atgagtcttc tgttacttgc aagttagctt gtacagctgt gaggaactgt    2820
gtcatgagtc tctgcagcag cagctacagt gagttaggac tgcagctgat catcgatgtg    2880
ctgactctga ggaacagttc ctattggctg gtgaggacag agcttctgga aacccttgca    2940
gagattgact tcaggctggt gagcttttg gaggcaaaag cagaaaactt acacagaggg    3000
gctcatcatt atacagggct tttaaaactg caagaacgag tgctcaataa tgttgtcatc    3060
catttgcttg gagatgaaga ccccagggtg cgacatgttg ccgcagcatc actaattagg    3120
cttgtcccaa agctgtttta taatgtgac caaggacaag ctgatccagt agtggccgtg    3180
gcaagagatc aaagcagtgt ttacctgaaa cttctcatgc atgagacgca gcctccatct    3240
catttctccg tcagcacaat aaccagaata tatagaggct ataacctact accaagcata    3300
acagacgtca ctatgaaaaa taacctttca agagttattg cagcagtttc tcatgaacta    3360
atcacatcaa ccaccagagc actcacattt ggatgctgtg aagctttgtg tcttctttcc    3420
actgccttcc cagtttgcat ttggagttta ggttggcact gtggagtgcc tccactgagt    3480
gcctcagatg agtctaggaa gagctgtacc gttgggatgg ccacaatgat tctgaccctg    3540
ctctcgtcag cttggttccc attggatctc tcagcccatc aagatgcttt gattttggcc    3600
ggaaacttgc ttgcagccag tgctcccaaa tctctgagaa gttcatgggc ctctgaagaa    3660
gaagccaacc cagcagccac caagcaagag gaggtctggc cagccctggg ggaccgggcc    3720
ctggtgccca tggtggagca gctcttctct cacctgctga aggtgattaa catttgtgcc    3780
cacgtcctgg atgacgtggc tcctggaccc gcaataaagg cagccttgcc ttctctaaca    3840 aaccccctt ctctaagtcc catccgacga aggggaagg agaagaacc aggagaacaa    3900 gcatctgtac cgttgagtcc caagaaaggc agtgaggcca gtgcagcttc tagacaatct    3960 gataccctcag gtcctgttac aacaagtaaa tcctcatcac tggggagttt ctatcatctt    4020
ccttcatacc tcaaactgca tgatgtcctg aaagctacac acgctaacta caaggtcacg    4080
ctggatcttc agaacagcac ggaaaagttt ggagggtttc tccgctcagc cttggatgtt    4140
ctttctcaga tactagagct ggccacactg caggacattg ggaagtgtgt tgaagagatc    4200
ctaggatacc tgaaatcctg ctttagtcga gaaccaatga tggcaactgt ttgtgttcaa    4260
caattgttga agactctctt tggcacaaac ttggcctccc agtttgatgg cttatcttcc    4320
aaccccagca agtcacaagg ccgagcacag cgccttggct cctccagtgt gaggccaggc    4380
ttgtaccact actgcttcat ggccccgtac acccacttca cccaggccct cgctgacgcc    4440
agcctgagga acatggtgca ggcggagcag gagaacgaca cctcgggatg gtttgatgtc    4500
ctccagaaag tgtctaccca gttgaagaca aacctcacga gtgtcacaaa gaaccgtgca    4560
gataagaatg ctattcataa tcacattcgt ttgtttgaac ctcttgttat aaaagcttta    4620
aaacagtaca cgactacaac atgtgtgcag ttacagaagc aggttttaga tttgctggcg    4680
cagctggttc agttacgggt taattactgt cttctggatt cagatcaggt gtttattggc    4740
tttgtattga aacagtttga atacattgaa gtgggccagt tcagggaatc agaggcaatc    4800
attccaaaca tctttttctt cttggtatta ctatcttatg aacgctatca ttcaaaacag    4860
```

```
atcattggaa ttcctaaaat cattcagctc tgtgatggca tcatggccag tggaaggaag   4920
gctgtgacac atgccatacc ggctctgcag cccatagtcc acgacctctt tgtattaaga   4980
ggaacaaata aagctgatgc aggaaaagag cttgaaaccc aaaaagaggt ggtggtgtca   5040
atgttactga gactcatcca gtaccatcag gtgttggaga tgttcattct tgtcctgcag   5100
cagtgccaca aggagaatga agacaagtgg aagcgactgt ctcgacagat agctgacatc   5160
atcctcccaa tgttagccaa acagcagatg cacattgact ctcatgaagc ccttggagtg   5220
ttaaatacat tatttgagat tttggcccct tcctccctcc gtccggtaga catgctttta   5280
cggagtatgt tcgtcactcc aaacacaatg gcgtccgtga gcactgttca actgtggata   5340
tcgggaattc tggccatttt gagggttctg atttcccagt caactgaaga tattgttctt   5400
tctcgtattc aggagctctc cttctctccg tatttaatct cctgtacagt aattaatagg   5460
ttaagagatg ggacagtac ttcaacgcta aagaacaca gtgaaggaa acaaataaag   5520
aatttgccag aagaaacatt ttcaaggttt ctattacaac tggttggtat tcttttagaa   5580
gacattgtta caaaacagct gaaggtggaa atgagtgagc agcaacatac tttctattgc   5640
caggaactag gcacactgct aatgtgtctg atccacatct tcaagtctgg aatgttccgg   5700
agaatcacag cagctgccac taggctgttc cgcagtgatg gctgtggcgg cagtttctac   5760
accctggaca gcttgaactt gcgggctcgt tccatgatca ccaccaccc ggccctggtg   5820
ctgctctggt gtcagatact gctgcttgtc aaccacaccg actaccgctg gtgggcagaa   5880
gtgcagcaga ccccgaaaag acacagtctg tccagcacaa agttacttag tccccagatg   5940
tctggagaag aggaggattc tgacttggca gccaaacttg gaatgtgcaa tagagaaata   6000
gtacgaagag gggctctcat tctcttctgt gattatgtct gtcagaacct ccatgactcc   6060
gagcacttaa cgtggctcat tgtaaatcac attcaagatc tgatcagcct ttcccacgag   6120
cctccagtac aggacttcat cagtgccgtt catcggaact ctgctgccag cggcctgttc   6180
atccaggcaa ttcagtctcg ttgtgaaaac cttttcaactc caaccatgct gaagaaaact   6240
cttcagtgct tggaggggat ccatctcagc cagtcgggag ctgtgctcac gctgtatgtg   6300
gacaggcttc tgtgcacccc tttccgtgtg ctggctcgca tggtcgacat ccttgcttgt   6360
cgccgggtag aaatgcttct ggctgcaaat ttacagagca gcatggccca gttgccaatg   6420
gaagaactca cagaatcca ggaatacctt cagagcagcg ggctcgctca gagacaccaa   6480
aggctctatt ccctgctgga caggtttcgt ctctccacca tgcaagactc acttagtccc   6540
tctcctccag tctcttccca cccgctggac ggggatgggc acgtgtcact ggaaacagtg   6600
agtccggaca aagactggta cgttcatctt gtcaaatccc agtgttggac caggtcagat   6660
tctgcactgc tggaaggtgc agagctggtg aatcggattc ctgctgaaga tatgaatgcc   6720
ttcatgatga actcggagtt caacctaagc ctgctagctc catgcttaag cctagggatg   6780
agtgaaattt ctggtggcca aagagtgcc cttttttgaag cagcccgtga ggtgactctg   6840
gcccgtgtga gcggcaccgt gcagcagctc cctgctgtcc atcatgtctt ccagcccgag   6900
ctgcctgcag agccggcggc ctactggagc aagttgaatg atctgttttgg ggatgctgca   6960
ctgtatcagt ccctgcccac tctggcccgg gccctggcac agtacctggt ggtggtctcc   7020
aaactgccca gtcatttgca ccttcctcct gagaaagaga aggacattgt gaaattcgtg   7080
gtggcaaccc ttgaggccct gtcctggcat ttgatccatg agcagatccc gctgagtctg   7140
gatctccagg cagggctgga ctgctgctgc ctggccctgc agctgcctgg cctctggagc   7200
```

```
gtggtctcct ccacagagtt tgtgacccac gcctgctccc tcatctactg tgtgcacttc      7260
atcctggagg ccgttgcagt gcagcctgga gagcagcttc ttagtccaga aagaaggaca      7320
aataccccaa aagccatcag cgaggaggag gaggaagtag atccaaacac acagaatcct      7380
aagtatatca ctgcagcctg tgagatggtg gcagaaatgg tggagtctct gcagtcggtg      7440
ttggccttgg gtcataaaag gaatagcggc gtgccggcgt ttctcacgcc attgctcagg      7500
aacatcatca tcagcctggc ccgcctgccc cttgtcaaca gctacacacg tgtgccccca      7560
ctggtgtgga agcttggatg gtcacccaaa ccgggagggg attttggcac agcattccct      7620
gagatccccg tggagttcct ccaggaaaag gaagtcttta aggagttcat ctaccgcatc      7680
aacacactag gctggaccag tcgtactcag tttgaagaaa cttgggccac cctccttggt      7740
gtcctggtga cgcagcccct cgtgatggag caggaggaga gcccaccaga agaagacaca      7800
gagaggaccc agatcaacgt cctggccgtg caggccatca cctcactggt gctcagtgca      7860
atgactgtgc ctgtggccgg caacccagct gtaagctgct tggagcagca gccccggaac      7920
aagcctctga aagctctcga caccaggttt ggggaggaagc tgagcattat cagagggatt      7980
gtggagcaag agattcaagc aatggtttca aagagagaga atattgccac ccatcattta      8040
tatcaggcat gggatcctgt cccttctctg tctccggcta ctacaggtgc cctcatcagc      8100
cacgagaagc tgctgctaca gatcaaccc gagcgggagc tggggagcat gagctacaaa      8160
ctcggccagt gtccataca ctccgtgtgg ctggggaaca gcatcacacc cctgagggag      8220
gaggaatggg acgaggaaga ggaggaggag gccgacgccc ctgcaccttc gtcaccaccc      8280
acgtctccag tcaactccag gaaacaccgg gctggagttg acatccactc ctgttcgcag      8340 ttttttgcttg agttgtacag ccgctggatc ctgccgtcca gctcagccag gaggaccccg      8400
gccatcctga tcagtgaggt ggtcagatcc cttctagtgg tctcagactt gttcaccgag      8460
cgcaaccagt ttgagctgat gtatgtgacg ctgacagaac tgcgaagggt gcaccctttca      8520 gaagacgaga tcctcgctca gtacctggtg cctgccacct gcaaggcagc tgccgtcctt      8580
gggatggaca aggccgtggc ggagcctgtc agccgcctgc tggagagcac gctcaggagc      8640
agccacctgc ccagcagggt tggagccctg cacggcgtcc tctatgtgct ggagtgcgac      8700
ctgctggacg acactgccaa gcagctcatc ccggtcatca gcgactatct cctctccaac      8760
ctgaaaggga tcgcccactg cgtgaacatt cacagccagc agcacgtact ggtcatgtgt      8820
gccactgcgt tttacctcat tgagaactat cctctggacg tagggccgga attttcagca      8880
tcaataatac agatgtgtgg ggtgatgctg tctggaagtg aggagtccac cccctccatc      8940
atttaccact gtgccctcag aggcctggag cgcctcctgc tctctgagca gctctcccgc      9000
ctggatgcag aatcgctggt caagctgagt gtggacagag tgaacgtgca cagcccgcac      9060
cgggccatgg cggctctggg cctgatgctc acctgcatgt acacaggaaa ggagaaagtc      9120
agtccgggta gaacttcaga ccctaatcct gcagcccccg cagcgagtc agtgattgtt      9180 gctatggagc gggtatctgt tcttttgat aggatcagga aaggctttcc ttgtgaagcc      9240
agagtggtgg ccaggatcct gccccagttt ctagacgact tcttcccacc ccaggacatc      9300
atgaacaaag tcatcggaga gtttctgtcc aaccagcagc atacccccca gttcatggcc      9360
accgtggtgt ataaggtgtt tcagactctg cacagcaccg gcagtcgtc catggtccgg      9420 gactgggtca tgctgtccct ctccaacttc acgcagaggg ccccggtcgc catggccacg      9480
tggagcctct cctgcttctt tgtcagcgcg tccaccagcc cgtgggtcgc ggcgatcctc      9540
ccacatgtca tcagcaggat gggcaagctg gagcaggtgg acgtgaacct tttctgcctg      9600
```

```
gtcgccacag acttctacag acaccagata gaggaggagc tcgaccgcag ggccttccag    9660
tctgtgcttg aggtggttgc agccccagga agcccatatc accggctgct gacttgttta    9720
cgaaatgtcc acaaggtcac cacctgctga gcgccatggt gggagagact gtgaggcggc    9780
agctggggcc ggagcctttg gaagtctgtg cccttgtgcc ctgcctccac cgagccagct    9840
tggtccctat gggcttccgc acatgccgcg ggcggccagg caacgtgcgt gtctctgcca    9900
tgtggcagaa gtgctctttg tggcagtggc caggcaggga gtgtctgcag tcctggtggg    9960
gctgagcctg aggccttcca gaaagcagga gcagctgtgc tgcaccccat gtgggtgacc    10020
aggtcctttc tcctgatagt cacctgctgg ttgttgccag gttgcagctg ctcttgcatc    10080
tgggccagaa gtcctccctc ctgcaggctg gctgttggcc cctctgctgt cctgcagtag    10140
aaggtgccgt gagcaggctt tgggaacact ggcctgggtc tccctggtgg ggtgtgcatg    10200
ccacgccccg tgtctggatg cacagatgcc atggcctgtg ctgggccagt ggctggggt    10260 gctagacacc cggcaccatt ctcccttctc tcttttcttc tcaggattta aaatttaatt    10320
atatcagtaa agagattaat tttaacgaac tctttctatg cccgtgtaaa gtatgtgaat    10380
cgcaaggcct gtgctgcatg cgacagcgtc cggggtggtg dacagggccc ccggccacgc    10440
tccctctcct gtagccactg gcatagccct cctgagcacc cgctgacatt tccgttgtac    10500
atgttcctgt ttatgcattc acaaggtgac tgggatgtag agaggcgtta gtgggcaggt    10560
ggccacagca ggactgagga caggccccca ttatcctagg ggtgcgctca actgcagccc    10620
ctcctcctcg ggcacagacg actgtcgttc tccacccacc agtcagggac agcagcctcc    10680
ctgtcactca gctgagaagg ccagccctcc ctggctgtga gcagcctcca ctgtgtccag    10740
agacatgggc ctcccactcc tgttccttgc tagccctggg gtggcgtctg cctaggagct    10800
ggctggcagg tgttgggacc tgctgctcca tggatgcatg ccctaagagt gtcactgagc    10860
tgtgttttgt ctgagcctct ctcggtcaac agcaaagctt ggtgtcttgg cactgttagt    10920
gacagagccc agcatcccct ctgccccgt tccagctgac atcttgcacg gtgacccctt    10980
ttagtcagga gagtgcagat ctgtgctcat cggagactgc cccacggccc tgtcagagcc    11040
gccactccta tccccaggac aggtccctgg accagcctcc tgtttgcagg cccagaggag    11100
ccaagtcatt aaaatggaag tggattctgg atggccgggc tgctgctgat gtaggagctg    11160
gatttgggag ctctgcttgc cgactggctg tgagacgagg caggggctct gcttcctcag    11220
ccctagaggc gagccaggca aggttggcga ctgtcatgtg gcttggtttg gtcatgcccg    11280
tcgatgtttt gggtattgaa tgtggtaagt ggaggaaatg ttggaactct gtgcaggtgc    11340
tgccttgaga ccccaagct tccacctgtc cctctcctat gtggcagctg gggagcagct    11400
gagatgtgga cttgtatgct gcccacatac gtgaggggga gctgaaaggg agccctgct    11460 caaagggagc cctcctctg agcagcctct gccaggcctg tatgaggctt tccccaccag    11520
ctcccaacag aggcctcccc cagccaggac cacctcgtcc tcgtggcggg gcagcaggag    11580
cggtagaaag gggtccgatg tttgaggagg cccttaaggg aagctactga attataacac    11640
gtaagaaaat caccattctt ccgtattggt tgggggctcc tgtttctcat cctagctttt    11700
tcctggaaaa gcccgctaga aggtttggga acgagggaa agttctcaga actgttgctg    11760
ctccccaccc gcctcccgcc tccccgcag gttatgtcag cagctctgag acagcagtat    11820
cacaggccaa atgttgttcc tggctagatg tttacatttg taagaaataa cactgtgaat    11880
gtaaaacaga gccattccct tggaatgcat atcgctgggc tcaacataga gtttgtcttc    11940
```

```
ctcttgttta cgacgtgatc taaaccagtc cttagcaagg ggctcagaac accccgctct   12000
ggcagtaggt gtcccccacc cccaaagacc tgcctgtgtg ctccggagat gaatatgagc   12060
tcattagtaa aaatgacttc acccacgcat atacataaag tatccatgca tgtgcatata   12120
gacacatcta taattttaca cacacacctc tcaagacgga gatgcatggc ctctaagagt   12180
gcccgtgtcg gttcttcctg gaagttgact ttccttagac ccgccaggtc aagttagccg   12240
cgtgacggac atccaggcgt gggacgtggt cagggcaggg ctcattcatt gcccactagg   12300
atcccactgg cgaagatggt ctccatatca gctctctgca aagggagga agactttatc    12360
atgttcctaa aaatctgtgg caagcaccca tcgtattatc caaattttgt tgcaaatgtg   12420
attaatttgg ttgtcaagtt ttggggggtgg gctgtgggga gattgctttt gttttcctgc  12480
tggtaatatc gggaaagatt ttaatgaaac cagggtagaa ttgtttggca atgcactgaa   12540
gcgtgtttct ttcccaaaat gtgcctccct tccgctgcgg gcccagctga gtctatgtag   12600
gtgatgtttc cagctgccaa gtgctctttg ttactgtcca ccctcatttc tgccagcgca   12660
tgtgtccttt caaggggaaa atgtgaagct gaaccccctc cagacaccca gaatgtagca   12720
tctgagaagg ccctgtgccc taaaggacac ccctcgcccc catcttcatg gagggggtca   12780
tttcagagcc ctcggagcca atgaacagct cctcctcttg gagctgagat gagccccacg   12840
tggagctcgg gacggatagt agacagcaat aactcggtgt gtggccgcct ggcaggtgga   12900
acttcctccc gttgcgggggt ggagtgaggt tagttctgtg tgtctggtgg gtggagtcag   12960
gcttctcttg ctacctgtga gcatccttcc cagcagacat cctcatcggg ctttgtccct   13020
cccccgcttc ctccctctgc ggggaggacc cgggaccaca gctgctggcc agggtagact   13080
tggagctgtc ctccagaggg gtcacgtgta ggagtgagaa gaggaagat cttgagagct    13140
gctgagggac cttggagagc tcaggatggc tcagacgagg acactcgctt gccgggcctg   13200
gccctcctgg gaaggaggga gctgctcaga atgccgcatg acaactgaag gcaacctgga   13260
aggttcaggg cccgctcttc ccccatgtgc ctgtcacgct ctggtgcagt caaaggaacg   13320
ccttcccctc agttgtttct aagagcagag tctcccgctg caatctgggt ggtaactgcc   13380
agccttggag gatcgtggcc aacgtggacc tgcctacgga gggtgggctc tgacccaagt   13440
ggggcctcct tgcccaggtc tcactgcttt gcaccgtggt cagagggact gtcagctgag   13500
cttgagctcc cctggagcca gcagggctgt gatgggcgag tcccggagcc ccacccagac   13560
ctgaatgctt ctgagagcaa agggaaggac tgacgagaga tgtatattta attttttaac   13620
tgctgcaaac attgtacatc caaattaaag ggaaaaaatg gaaaccatca at             13672
```

<210> SEQ ID NO 49
<211> LENGTH: 3144
<212> TYPE: PRT
<213> ORGANISM: Homo sapiens

<400> SEQUENCE: 49

Met Ala Thr Leu Glu Lys Leu Met Lys Ala Phe Glu Ser Leu Lys Ser
1               5                   10                  15

Phe Gln Gln Gln Gln Gln Gln Gln Gln Gln Gln Gln Gln Gln Gln Gln
            20                  25                  30

Gln Gln Gln Gln Gln Gln Gln Pro Pro Pro Pro Pro Pro Pro Pro Pro
        35                  40                  45

Pro Pro Pro Gln Leu Pro Gln Pro Pro Pro Gln Ala Gln Pro Leu Leu
    50                  55                  60

Pro Gln Pro Gln Pro Pro Pro Pro Pro Pro Pro Pro Pro Gly Pro

-continued

```
                65                  70                  75                  80
        Ala Val Ala Glu Glu Pro Leu His Arg Pro Lys Lys Glu Leu Ser Ala
                            85                  90                  95

Thr Lys Lys Asp Arg Val Asn His Cys Leu Thr Ile Cys Glu Asn Ile
                        100                 105                 110

Val Ala Gln Ser Val Arg Asn Ser Pro Glu Phe Gln Lys Leu Leu Gly
                        115                 120                 125

Ile Ala Met Glu Leu Phe Leu Leu Cys Ser Asp Asp Ala Glu Ser Asp
                    130                 135                 140

Val Arg Met Val Ala Asp Glu Cys Leu Asn Lys Val Ile Lys Ala Leu
        145                 150                 155                 160

Met Asp Ser Asn Leu Pro Arg Leu Gln Leu Glu Leu Tyr Lys Glu Ile
                        165                 170                 175

Lys Lys Asn Gly Ala Pro Arg Ser Leu Arg Ala Ala Leu Trp Arg Phe
                        180                 185                 190

Ala Glu Leu Ala His Leu Val Arg Pro Gln Lys Cys Arg Pro Tyr Leu
                        195                 200                 205

Val Asn Leu Leu Pro Cys Leu Thr Arg Thr Ser Lys Arg Pro Glu Glu
                    210                 215                 220

Ser Val Gln Glu Thr Leu Ala Ala Ala Val Pro Lys Ile Met Ala Ser
        225                 230                 235                 240

Phe Gly Asn Phe Ala Asn Asp Asn Glu Ile Lys Val Leu Leu Lys Ala
                        245                 250                 255

Phe Ile Ala Asn Leu Lys Ser Ser Ser Pro Thr Ile Arg Arg Thr Ala
                        260                 265                 270

Ala Gly Ser Ala Val Ser Ile Cys Gln His Ser Arg Arg Thr Gln Tyr
                    275                 280                 285

Phe Tyr Ser Trp Leu Leu Asn Val Leu Leu Gly Leu Leu Val Pro Val
                        290                 295                 300

Glu Asp Glu His Ser Thr Leu Leu Ile Leu Gly Val Leu Leu Thr Leu
        305                 310                 315                 320

Arg Tyr Leu Val Pro Leu Leu Gln Gln Gln Val Lys Asp Thr Ser Leu
                        325                 330                 335

Lys Gly Ser Phe Gly Val Thr Arg Lys Glu Met Glu Val Ser Pro Ser
                        340                 345                 350

Ala Glu Gln Leu Val Gln Val Tyr Glu Leu Thr Leu His His Thr Gln
                    355                 360                 365

His Gln Asp His Asn Val Val Thr Gly Ala Leu Glu Leu Leu Gln Gln
                    370                 375                 380

Leu Phe Arg Thr Pro Pro Pro Glu Leu Leu Gln Thr Leu Thr Ala Val
        385                 390                 395                 400

Gly Gly Ile Gly Gln Leu Thr Ala Ala Lys Glu Glu Ser Gly Gly Arg
                        405                 410                 415

Ser Arg Ser Gly Ser Ile Val Glu Leu Ile Ala Gly Gly Gly Ser Ser
                        420                 425                 430

Cys Ser Pro Val Leu Ser Arg Lys Gln Lys Gly Lys Val Leu Leu Gly
                    435                 440                 445

Glu Glu Glu Ala Leu Glu Asp Asp Ser Glu Ser Arg Ser Asp Val Ser
                    450                 455                 460

Ser Ser Ala Leu Thr Ala Ser Val Lys Asp Glu Ile Ser Gly Glu Leu
        465                 470                 475                 480

Ala Ala Ser Ser Gly Val Ser Thr Pro Gly Ser Ala Gly His Asp Ile
                        485                 490                 495
```

```
Ile Thr Glu Gln Pro Arg Ser Gln His Thr Leu Gln Ala Asp Ser Val
            500                 505                 510

Asp Leu Ala Ser Cys Asp Leu Thr Ser Ser Ala Thr Asp Gly Asp Glu
            515                 520                 525

Glu Asp Ile Leu Ser His Ser Ser Gln Val Ser Ala Val Pro Ser
            530                 535                 540

Asp Pro Ala Met Asp Leu Asn Asp Gly Thr Gln Ala Ser Ser Pro Ile
545                 550                 555                 560

Ser Asp Ser Ser Gln Thr Thr Thr Glu Gly Pro Asp Ser Ala Val Thr
                565                 570                 575

Pro Ser Asp Ser Ser Glu Ile Val Leu Asp Gly Thr Asp Asn Gln Tyr
            580                 585                 590

Leu Gly Leu Gln Ile Gly Gln Pro Gln Asp Glu Asp Glu Glu Ala Thr
            595                 600                 605

Gly Ile Leu Pro Asp Glu Ala Ser Glu Ala Phe Arg Asn Ser Ser Met
            610                 615                 620

Ala Leu Gln Gln Ala His Leu Leu Lys Asn Met Ser His Cys Arg Gln
625                 630                 635                 640

Pro Ser Asp Ser Ser Val Asp Lys Phe Val Leu Arg Asp Glu Ala Thr
                645                 650                 655

Glu Pro Gly Asp Gln Glu Asn Lys Pro Cys Arg Ile Lys Gly Asp Ile
            660                 665                 670

Gly Gln Ser Thr Asp Asp Ser Ala Pro Leu Val His Cys Val Arg
            675                 680                 685

Leu Leu Ser Ala Ser Phe Leu Leu Thr Gly Gly Lys Asn Val Leu Val
            690                 695                 700

Pro Asp Arg Asp Val Arg Val Ser Val Lys Ala Leu Ala Leu Ser Cys
705                 710                 715                 720

Val Gly Ala Ala Val Ala Leu His Pro Glu Ser Phe Phe Ser Lys Leu
                725                 730                 735

Tyr Lys Val Pro Leu Asp Thr Thr Glu Tyr Pro Glu Glu Gln Tyr Val
            740                 745                 750

Ser Asp Ile Leu Asn Tyr Ile Asp His Gly Asp Pro Gln Val Arg Gly
            755                 760                 765

Ala Thr Ala Ile Leu Cys Gly Thr Leu Ile Cys Ser Ile Leu Ser Arg
            770                 775                 780

Ser Arg Phe His Val Gly Asp Trp Met Gly Thr Ile Arg Thr Leu Thr
785                 790                 795                 800

Gly Asn Thr Phe Ser Leu Ala Asp Cys Ile Pro Leu Leu Arg Lys Thr
                805                 810                 815

Leu Lys Asp Glu Ser Ser Val Thr Cys Lys Leu Ala Cys Thr Ala Val
            820                 825                 830

Arg Asn Cys Val Met Ser Leu Cys Ser Ser Tyr Ser Glu Leu Gly
            835                 840                 845

Leu Gln Leu Ile Ile Asp Val Leu Thr Leu Arg Asn Ser Ser Tyr Trp
            850                 855                 860

Leu Val Arg Thr Glu Leu Leu Glu Thr Leu Ala Glu Ile Asp Phe Arg
865                 870                 875                 880

Leu Val Ser Phe Leu Glu Ala Lys Ala Glu Asn Leu His Arg Gly Ala
                885                 890                 895

His His Tyr Thr Gly Leu Leu Lys Leu Gln Glu Arg Val Leu Asn Asn
            900                 905                 910
```

```
Val Val Ile His Leu Leu Gly Asp Glu Asp Pro Arg Val Arg His Val
        915                 920                 925

Ala Ala Ala Ser Leu Ile Arg Leu Val Pro Lys Leu Phe Tyr Lys Cys
        930                 935                 940

Asp Gln Gly Gln Ala Asp Pro Val Val Ala Val Ala Arg Asp Gln Ser
945                 950                 955                 960

Ser Val Tyr Leu Lys Leu Leu Met His Glu Thr Gln Pro Ser His
                965                 970                 975

Phe Ser Val Ser Thr Ile Thr Arg Ile Tyr Arg Gly Tyr Asn Leu Leu
        980                 985                 990

Pro Ser Ile Thr Asp Val Thr Met Glu Asn Asn Leu Ser Arg Val Ile
        995                 1000                1005

Ala Ala Val Ser His Glu Leu Ile Thr Ser Thr Thr Arg Ala Leu
        1010                1015                1020

Thr Phe Gly Cys Cys Glu Ala Leu Cys Leu Leu Ser Thr Ala Phe
        1025                1030                1035

Pro Val Cys Ile Trp Ser Leu Gly Trp His Cys Gly Val Pro Pro
        1040                1045                1050

Leu Ser Ala Ser Asp Glu Ser Arg Lys Ser Cys Thr Val Gly Met
        1055                1060                1065

Ala Thr Met Ile Leu Thr Leu Leu Ser Ser Ala Trp Phe Pro Leu
        1070                1075                1080

Asp Leu Ser Ala His Gln Asp Ala Leu Ile Leu Ala Gly Asn Leu
        1085                1090                1095

Leu Ala Ala Ser Ala Pro Lys Ser Leu Arg Ser Ser Trp Ala Ser
        1100                1105                1110

Glu Glu Glu Ala Asn Pro Ala Ala Thr Lys Gln Glu Glu Val Trp
        1115                1120                1125

Pro Ala Leu Gly Asp Arg Ala Leu Val Pro Met Val Glu Gln Leu
        1130                1135                1140

Phe Ser His Leu Leu Lys Val Ile Asn Ile Cys Ala His Val Leu
        1145                1150                1155

Asp Asp Val Ala Pro Gly Pro Ala Ile Lys Ala Ala Leu Pro Ser
        1160                1165                1170

Leu Thr Asn Pro Pro Ser Leu Ser Pro Ile Arg Arg Lys Gly Lys
        1175                1180                1185

Glu Lys Glu Pro Gly Glu Gln Ala Ser Val Pro Leu Ser Pro Lys
        1190                1195                1200

Lys Gly Ser Glu Ala Ser Ala Ala Ser Arg Gln Ser Asp Thr Ser
        1205                1210                1215

Gly Pro Val Thr Thr Ser Lys Ser Ser Ser Leu Gly Ser Phe Tyr
        1220                1225                1230

His Leu Pro Ser Tyr Leu Lys Leu His Asp Val Leu Lys Ala Thr
        1235                1240                1245

His Ala Asn Tyr Lys Val Thr Leu Asp Leu Gln Asn Ser Thr Glu
        1250                1255                1260

Lys Phe Gly Gly Phe Leu Arg Ser Ala Leu Asp Val Leu Ser Gln
        1265                1270                1275

Ile Leu Glu Leu Ala Thr Leu Gln Asp Ile Gly Lys Cys Val Glu
        1280                1285                1290

Glu Ile Leu Gly Tyr Leu Lys Ser Cys Phe Ser Arg Glu Pro Met
        1295                1300                1305

Met Ala Thr Val Cys Val Gln Gln Leu Leu Lys Thr Leu Phe Gly
```

```
                     1310                1315                1320
Thr Asn Leu Ala Ser Gln Phe Asp Gly Leu Ser Ser Asn Pro Ser
    1325                1330                1335
Lys Ser Gln Gly Arg Ala Gln Arg Leu Gly Ser Ser Ser Val Arg
    1340                1345                1350
Pro Gly Leu Tyr His Tyr Cys Phe Met Ala Pro Tyr Thr His Phe
    1355                1360                1365
Thr Gln Ala Leu Ala Asp Ala Ser Leu Arg Asn Met Val Gln Ala
    1370                1375                1380
Glu Gln Glu Asn Asp Thr Ser Gly Trp Phe Asp Val Leu Gln Lys
    1385                1390                1395
Val Ser Thr Gln Leu Lys Thr Asn Leu Thr Ser Val Thr Lys Asn
    1400                1405                1410
Arg Ala Asp Lys Asn Ala Ile His Asn His Ile Arg Leu Phe Glu
    1415                1420                1425
Pro Leu Val Ile Lys Ala Leu Lys Gln Tyr Thr Thr Thr Thr Cys
    1430                1435                1440
Val Gln Leu Gln Lys Gln Val Leu Asp Leu Leu Ala Gln Leu Val
    1445                1450                1455
Gln Leu Arg Val Asn Tyr Cys Leu Leu Asp Ser Asp Gln Val Phe
    1460                1465                1470
Ile Gly Phe Val Leu Lys Gln Phe Glu Tyr Ile Glu Val Gly Gln
    1475                1480                1485
Phe Arg Glu Ser Glu Ala Ile Ile Pro Asn Ile Phe Phe Phe Leu
    1490                1495                1500
Val Leu Leu Ser Tyr Glu Arg Tyr His Ser Lys Gln Ile Ile Gly
    1505                1510                1515
Ile Pro Lys Ile Ile Gln Leu Cys Asp Gly Ile Met Ala Ser Gly
    1520                1525                1530
Arg Lys Ala Val Thr His Ala Ile Pro Ala Leu Gln Pro Ile Val
    1535                1540                1545
His Asp Leu Phe Val Leu Arg Gly Thr Asn Lys Ala Asp Ala Gly
    1550                1555                1560
Lys Glu Leu Glu Thr Gln Lys Glu Val Val Val Ser Met Leu Leu
    1565                1570                1575
Arg Leu Ile Gln Tyr His Gln Val Leu Glu Met Phe Ile Leu Val
    1580                1585                1590
Leu Gln Gln Cys His Lys Glu Asn Glu Asp Lys Trp Lys Arg Leu
    1595                1600                1605
Ser Arg Gln Ile Ala Asp Ile Ile Leu Pro Met Leu Ala Lys Gln
    1610                1615                1620
Gln Met His Ile Asp Ser His Glu Ala Leu Gly Val Leu Asn Thr
    1625                1630                1635
Leu Phe Glu Ile Leu Ala Pro Ser Ser Leu Arg Pro Val Asp Met
    1640                1645                1650
Leu Leu Arg Ser Met Phe Val Thr Pro Asn Thr Met Ala Ser Val
    1655                1660                1665
Ser Thr Val Gln Leu Trp Ile Ser Gly Ile Leu Ala Ile Leu Arg
    1670                1675                1680
Val Leu Ile Ser Gln Ser Thr Glu Asp Ile Val Leu Ser Arg Ile
    1685                1690                1695
Gln Glu Leu Ser Phe Ser Pro Tyr Leu Ile Ser Cys Thr Val Ile
    1700                1705                1710
```

-continued

Asn Arg Leu Arg Asp Gly Asp Ser Thr Ser Thr Leu Glu Glu His
1715                1720                1725

Ser Glu Gly Lys Gln Ile Lys Asn Leu Pro Glu Glu Thr Phe Ser
1730                1735                1740

Arg Phe Leu Leu Gln Leu Val Gly Ile Leu Leu Glu Asp Ile Val
1745                1750                1755

Thr Lys Gln Leu Lys Val Glu Met Ser Glu Gln His Thr Phe
1760                1765                1770

Tyr Cys Gln Glu Leu Gly Thr Leu Leu Met Cys Leu Ile His Ile
1775                1780                1785

Phe Lys Ser Gly Met Phe Arg Arg Ile Thr Ala Ala Ala Thr Arg
1790                1795                1800

Leu Phe Arg Ser Asp Gly Cys Gly Gly Ser Phe Tyr Thr Leu Asp
1805                1810                1815

Ser Leu Asn Leu Arg Ala Arg Ser Met Ile Thr Thr His Pro Ala
1820                1825                1830

Leu Val Leu Leu Trp Cys Gln Ile Leu Leu Leu Val Asn His Thr
1835                1840                1845

Asp Tyr Arg Trp Trp Ala Glu Val Gln Gln Thr Pro Lys Arg His
1850                1855                1860

Ser Leu Ser Ser Thr Lys Leu Leu Ser Pro Gln Met Ser Gly Glu
1865                1870                1875

Glu Glu Asp Ser Asp Leu Ala Ala Lys Leu Gly Met Cys Asn Arg
1880                1885                1890

Glu Ile Val Arg Arg Gly Ala Leu Ile Leu Phe Cys Asp Tyr Val
1895                1900                1905

Cys Gln Asn Leu His Asp Ser Glu His Leu Thr Trp Leu Ile Val
1910                1915                1920

Asn His Ile Gln Asp Leu Ile Ser Leu Ser His Glu Pro Pro Val
1925                1930                1935

Gln Asp Phe Ile Ser Ala Val His Arg Asn Ser Ala Ala Ser Gly
1940                1945                1950

Leu Phe Ile Gln Ala Ile Gln Ser Arg Cys Glu Asn Leu Ser Thr
1955                1960                1965

Pro Thr Met Leu Lys Lys Thr Leu Gln Cys Leu Glu Gly Ile His
1970                1975                1980

Leu Ser Gln Ser Gly Ala Val Leu Thr Leu Tyr Val Asp Arg Leu
1985                1990                1995

Leu Cys Thr Pro Phe Arg Val Leu Ala Arg Met Val Asp Ile Leu
2000                2005                2010

Ala Cys Arg Arg Val Glu Met Leu Leu Ala Ala Asn Leu Gln Ser
2015                2020                2025

Ser Met Ala Gln Leu Pro Met Glu Glu Leu Asn Arg Ile Gln Glu
2030                2035                2040

Tyr Leu Gln Ser Ser Gly Leu Ala Gln Arg His Gln Arg Leu Tyr
2045                2050                2055

Ser Leu Leu Asp Arg Phe Arg Leu Ser Thr Met Gln Asp Ser Leu
2060                2065                2070

Ser Pro Ser Pro Pro Val Ser Ser His Pro Leu Asp Gly Asp Gly
2075                2080                2085

His Val Ser Leu Glu Thr Val Ser Pro Asp Lys Asp Trp Tyr Val
2090                2095                2100

-continued

```
His Leu Val Lys Ser Gln Cys Trp Thr Arg Ser Asp Ser Ala Leu
    2105                2110                2115

Leu Glu Gly Ala Glu Leu Val Asn Arg Ile Pro Ala Glu Asp Met
    2120                2125                2130

Asn Ala Phe Met Met Asn Ser Glu Phe Asn Leu Ser Leu Leu Ala
    2135                2140                2145

Pro Cys Leu Ser Leu Gly Met Ser Glu Ile Ser Gly Gly Gln Lys
    2150                2155                2160

Ser Ala Leu Phe Glu Ala Ala Arg Glu Val Thr Leu Ala Arg Val
    2165                2170                2175

Ser Gly Thr Val Gln Gln Leu Pro Ala Val His His Val Phe Gln
    2180                2185                2190

Pro Glu Leu Pro Ala Glu Pro Ala Ala Tyr Trp Ser Lys Leu Asn
    2195                2200                2205

Asp Leu Phe Gly Asp Ala Ala Leu Tyr Gln Ser Leu Pro Thr Leu
    2210                2215                2220

Ala Arg Ala Leu Ala Gln Tyr Leu Val Val Val Ser Lys Leu Pro
    2225                2230                2235

Ser His Leu His Leu Pro Pro Glu Lys Glu Lys Asp Ile Val Lys
    2240                2245                2250

Phe Val Val Ala Thr Leu Glu Ala Leu Ser Trp His Leu Ile His
    2255                2260                2265

Glu Gln Ile Pro Leu Ser Leu Asp Leu Gln Ala Gly Leu Asp Cys
    2270                2275                2280

Cys Cys Leu Ala Leu Gln Leu Pro Gly Leu Trp Ser Val Val Ser
    2285                2290                2295

Ser Thr Glu Phe Val Thr His Ala Cys Ser Leu Ile Tyr Cys Val
    2300                2305                2310

His Phe Ile Leu Glu Ala Val Ala Val Gln Pro Gly Glu Gln Leu
    2315                2320                2325

Leu Ser Pro Glu Arg Arg Thr Asn Thr Pro Lys Ala Ile Ser Glu
    2330                2335                2340

Glu Glu Glu Glu Val Asp Pro Asn Thr Gln Asn Pro Lys Tyr Ile
    2345                2350                2355

Thr Ala Ala Cys Glu Met Val Ala Glu Met Val Glu Ser Leu Gln
    2360                2365                2370

Ser Val Leu Ala Leu Gly His Lys Arg Asn Ser Gly Val Pro Ala
    2375                2380                2385

Phe Leu Thr Pro Leu Leu Arg Asn Ile Ile Ile Ser Leu Ala Arg
    2390                2395                2400

Leu Pro Leu Val Asn Ser Tyr Thr Arg Val Pro Pro Leu Val Trp
    2405                2410                2415

Lys Leu Gly Trp Ser Pro Lys Pro Gly Gly Asp Phe Gly Thr Ala
    2420                2425                2430

Phe Pro Glu Ile Pro Val Glu Phe Leu Gln Glu Lys Glu Val Phe
    2435                2440                2445

Lys Glu Phe Ile Tyr Arg Ile Asn Thr Leu Gly Trp Thr Ser Arg
    2450                2455                2460

Thr Gln Phe Glu Glu Thr Trp Ala Thr Leu Leu Gly Val Leu Val
    2465                2470                2475

Thr Gln Pro Leu Val Met Glu Gln Glu Glu Ser Pro Pro Glu Glu
    2480                2485                2490

Asp Thr Glu Arg Thr Gln Ile Asn Val Leu Ala Val Gln Ala Ile
```

-continued

```
            2495                2500                2505
Thr Ser Leu Val Leu Ser Ala Met Thr Val Pro Val Ala Gly Asn
    2510                2515                2520

Pro Ala Val Ser Cys Leu Glu Gln Gln Pro Arg Asn Lys Pro Leu
    2525                2530                2535

Lys Ala Leu Asp Thr Arg Phe Gly Arg Lys Leu Ser Ile Ile Arg
    2540                2545                2550

Gly Ile Val Glu Gln Glu Ile Gln Ala Met Val Ser Lys Arg Glu
    2555                2560                2565

Asn Ile Ala Thr His His Leu Tyr Gln Ala Trp Asp Pro Val Pro
    2570                2575                2580

Ser Leu Ser Pro Ala Thr Thr Gly Ala Leu Ile Ser His Glu Lys
    2585                2590                2595

Leu Leu Leu Gln Ile Asn Pro Glu Arg Glu Leu Gly Ser Met Ser
    2600                2605                2610

Tyr Lys Leu Gly Gln Val Ser Ile His Ser Val Trp Leu Gly Asn
    2615                2620                2625

Ser Ile Thr Pro Leu Arg Glu Glu Trp Asp Glu Glu Glu
    2630                2635                2640

Glu Glu Ala Asp Ala Pro Ala Pro Ser Ser Pro Pro Thr Ser Pro
    2645                2650                2655

Val Asn Ser Arg Lys His Arg Ala Gly Val Asp Ile His Ser Cys
    2660                2665                2670

Ser Gln Phe Leu Leu Glu Leu Tyr Ser Arg Trp Ile Leu Pro Ser
    2675                2680                2685

Ser Ser Ala Arg Arg Thr Pro Ala Ile Leu Ile Ser Glu Val Val
    2690                2695                2700

Arg Ser Leu Leu Val Val Ser Asp Leu Phe Thr Glu Arg Asn Gln
    2705                2710                2715

Phe Glu Leu Met Tyr Val Thr Leu Thr Glu Leu Arg Arg Val His
    2720                2725                2730

Pro Ser Glu Asp Glu Ile Leu Ala Gln Tyr Leu Val Pro Ala Thr
    2735                2740                2745

Cys Lys Ala Ala Ala Val Leu Gly Met Asp Lys Ala Val Ala Glu
    2750                2755                2760

Pro Val Ser Arg Leu Leu Glu Ser Thr Leu Arg Ser Ser His Leu
    2765                2770                2775

Pro Ser Arg Val Gly Ala Leu His Gly Val Leu Tyr Val Leu Glu
    2780                2785                2790

Cys Asp Leu Leu Asp Asp Thr Ala Lys Gln Leu Ile Pro Val Ile
    2795                2800                2805

Ser Asp Tyr Leu Leu Ser Asn Leu Lys Gly Ile Ala His Cys Val
    2810                2815                2820

Asn Ile His Ser Gln Gln His Val Leu Val Met Cys Ala Thr Ala
    2825                2830                2835

Phe Tyr Leu Ile Glu Asn Tyr Pro Leu Asp Val Gly Pro Glu Phe
    2840                2845                2850

Ser Ala Ser Ile Ile Gln Met Cys Gly Val Met Leu Ser Gly Ser
    2855                2860                2865

Glu Glu Ser Thr Pro Ser Ile Ile Tyr His Cys Ala Leu Arg Gly
    2870                2875                2880

Leu Glu Arg Leu Leu Leu Ser Glu Gln Leu Ser Arg Leu Asp Ala
    2885                2890                2895
```

```
Glu Ser Leu Val Lys Leu Ser Val Asp Arg Val Asn Val His Ser
    2900            2905                2910
Pro His Arg Ala Met Ala Ala Leu Gly Leu Met Leu Thr Cys Met
    2915            2920                2925
Tyr Thr Gly Lys Glu Lys Val Ser Pro Gly Arg Thr Ser Asp Pro
    2930            2935                2940
Asn Pro Ala Ala Pro Asp Ser Glu Ser Val Ile Val Ala Met Glu
    2945            2950                2955
Arg Val Ser Val Leu Phe Asp Arg Ile Arg Lys Gly Phe Pro Cys
    2960            2965                2970
Glu Ala Arg Val Val Ala Arg Ile Leu Pro Gln Phe Leu Asp Asp
    2975            2980                2985
Phe Phe Pro Pro Gln Asp Ile Met Asn Lys Val Ile Gly Glu Phe
    2990            2995                3000
Leu Ser Asn Gln Gln Pro Tyr Pro Gln Phe Met Ala Thr Val Val
    3005            3010                3015
Tyr Lys Val Phe Gln Thr Leu His Ser Thr Gly Gln Ser Ser Met
    3020            3025                3030
Val Arg Asp Trp Val Met Leu Ser Leu Ser Asn Phe Thr Gln Arg
    3035            3040                3045
Ala Pro Val Ala Met Ala Thr Trp Ser Leu Ser Cys Phe Phe Val
    3050            3055                3060
Ser Ala Ser Thr Ser Pro Trp Val Ala Ala Ile Leu Pro His Val
    3065            3070                3075
Ile Ser Arg Met Gly Lys Leu Glu Gln Val Asp Val Asn Leu Phe
    3080            3085                3090
Cys Leu Val Ala Thr Asp Phe Tyr Arg His Gln Ile Glu Glu Glu
    3095            3100                3105
Leu Asp Arg Arg Ala Phe Gln Ser Val Leu Glu Val Val Ala Ala
    3110            3115                3120
Pro Gly Ser Pro Tyr His Arg Leu Leu Thr Cys Leu Arg Asn Val
    3125            3130                3135
His Lys Val Thr Thr Cys
    3140

<210> SEQ ID NO 50
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 50
tggagtgggt aattcaacac a                                              21

<210> SEQ ID NO 51
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 51
gccagaaata tgggaaaagg                                                20
```

<210> SEQ ID NO 52
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 52
agaattccat gcaggacacc     20

<210> SEQ ID NO 53
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 53
gcagacatcc tcagggactc     20

<210> SEQ ID NO 54
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 54
tgatgggatg tgtcttccat     20

<210> SEQ ID NO 55
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 55
ggtcaggagt tcgagaccag     20

<210> SEQ ID NO 56
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 56
atgcaaccct cttggtgact     20

<210> SEQ ID NO 57
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

-continued

```
      Synthetic primer"

<400> SEQUENCE: 57
cgacaaaaac caacatccag                                              20

<210> SEQ ID NO 58
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 58
tcagctgagt tttccccatc                                              20

<210> SEQ ID NO 59
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 59
gaagcactcc cacaggactc                                              20

<210> SEQ ID NO 60
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 60
ctgctcttga gtgtcccaaa                                              20

<210> SEQ ID NO 61
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 61
ccactcatat gcctccacct                                              20

<210> SEQ ID NO 62
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 62
ctctggaaag gaccttgctg                                              20

<210> SEQ ID NO 63
<211> LENGTH: 20
```

-continued

<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 63
attcacatgc agggcctaga                                              20

<210> SEQ ID NO 64
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 64
ttggtggaag tgatagggaa a                                            21

<210> SEQ ID NO 65
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 65
gttttggcaa ggaagatgga                                              20

<210> SEQ ID NO 66
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 66
tgcgatgtta agtgtttcct g                                            21

<210> SEQ ID NO 67
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 67
cctggttatc agattccagc a                                            21

<210> SEQ ID NO 68
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 68

```
gcatttactt aattttgaag tccttat                                        27
```

<210> SEQ ID NO 69
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 69

```
cgaatatgcc ccatttaagc                                                20
```

<210> SEQ ID NO 70
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 70

```
cgttattttg caagcctgtg                                                20
```

<210> SEQ ID NO 71
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 71

```
ctcccaaagt gctgggatta                                                20
```

<210> SEQ ID NO 72
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 72

```
gttggagggc ttgtctcttg                                                20
```

<210> SEQ ID NO 73
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 73

```
cagggatggg aaagcaataa                                                20
```

<210> SEQ ID NO 74
<211> LENGTH: 20
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic primer"

<400> SEQUENCE: 74
acctggctta agtgctgctc                                                    20

<210> SEQ ID NO 75
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 75
ctcggctagt gaaaaccaaa                                                    20

<210> SEQ ID NO 76
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 76
gttccatggc tgagcaattt                                                    20

<210> SEQ ID NO 77
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 77
gctgagagat ggatacatgg tg                                                 22

<210> SEQ ID NO 78
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 78
cttgccttgg accttgtgtt                                                    20

<210> SEQ ID NO 79
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 79
tgcatcaagt gatcccagaa                                                    20

<210> SEQ ID NO 80
```

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 80
caagctggcg gtaagtgttt                                                     20

<210> SEQ ID NO 81
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 81
tccctctctt tccattctcg                                                     20

<210> SEQ ID NO 82
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 82
aagtggtgtc cgctggtaac                                                     20

<210> SEQ ID NO 83
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 83
gcctaaagaa aggcatcagg                                                     20

<210> SEQ ID NO 84
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 84
cgtttcactt aaaagttgag actgc                                               25

<210> SEQ ID NO 85
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 85
```

-continued tttcttagca agcctcatgg a                                              21

<210> SEQ ID NO 86
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 86
ctttgtggtg tttgggtgtg                                                20

<210> SEQ ID NO 87
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 87
tcccacagct cctgtcacta                                                20

<210> SEQ ID NO 88
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 88
tgtgacatgc cttcctcttg                                                20

<210> SEQ ID NO 89
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 89
aaagggacaa gccatcactg                                                20

<210> SEQ ID NO 90
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 90
cagttcccca agcaatttgt                                                20

<210> SEQ ID NO 91
<211> LENGTH: 20
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic primer"

<400> SEQUENCE: 91
ccatccacat ggtcacattt                                                    20

<210> SEQ ID NO 92
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 92
tcagggtcca agaacaaaat g                                                  21

<210> SEQ ID NO 93
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 93
gcttcagacc aaaaggtggt                                                    20

<210> SEQ ID NO 94
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 94
tttccagtaa tctctttaaa acttgg                                             26

<210> SEQ ID NO 95
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 95
taaaagatgc agaggcccat                                                    20

<210> SEQ ID NO 96
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 96
ggccagtaac cgtgtgttct                                                    20
```

```
<210> SEQ ID NO 97
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 97
tcatggctaa ggcagagtca                                                    20

<210> SEQ ID NO 98
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 98
ggattcgtac aataacgggt ca                                                 22

<210> SEQ ID NO 99
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 99
ggagcttctg gtgtcctctg                                                    20

<210> SEQ ID NO 100
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 100
ttcacgctgt gagtctttgc                                                    20

<210> SEQ ID NO 101
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic
      primer"

<400> SEQUENCE: 101
ctctttcgtg cttccacca                                                     19

<210> SEQ ID NO 102
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

<400> SEQUENCE: 102 tgcttcccttt ttattcccat t                                         21

<210> SEQ ID NO 103
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 103
cctggaaagt ctcagctcca                                            20

<210> SEQ ID NO 104
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 104
tgcttgaagc ttttagttga agg                                        23

<210> SEQ ID NO 105
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 105
atgagggaaa catgcagacc                                            20

<210> SEQ ID NO 106
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 106
tgtgaaattt tattttcctt cctg                                       24

<210> SEQ ID NO 107
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 107
ttccatttaa agaaaacagc aaaa                                       24

<210> SEQ ID NO 108
<211> LENGTH: 20
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 108
tgatgtgtgc ttgctgtcaa                                                20

<210> SEQ ID NO 109
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 109
acacacatgc agagcctgag                                                20

<210> SEQ ID NO 110
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 110
gatgttgaga gcagttttcc aa                                             22

<210> SEQ ID NO 111
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 111
gcccaaacct ggttcaaagt                                                20

<210> SEQ ID NO 112
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 112
cgtctcttgg cagcagactt                                                20

<210> SEQ ID NO 113
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 113
tatgcaacaa caagccaagg                                                20
```

<210> SEQ ID NO 114
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 114
ggtgtacagg aagctgtcgt t                                             21

<210> SEQ ID NO 115
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 115
gccctaccca aactgactga                                               20

<210> SEQ ID NO 116
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 116
gcaattgggg gaaatttaat c                                             21

<210> SEQ ID NO 117
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 117
catcacgtga cttcccaaaa                                               20

<210> SEQ ID NO 118
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 118
tgtatacttg gcgtaagtgc ttt                                           23

<210> SEQ ID NO 119
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 119
actgggcaag gcagagttt                                                    19

<210> SEQ ID NO 120
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 120
ggaccgagat gaaagcaaag                                                   20

<210> SEQ ID NO 121
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 121
gccaaagctc aggttactgg                                                   20

<210> SEQ ID NO 122
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 122
ctcactgcca tccagaaaca                                                   20

<210> SEQ ID NO 123
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 123
tttagtttcg atggagcttg g                                                 21

<210> SEQ ID NO 124
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 124
ggcattaata cctggtctct tctt                                              24

<210> SEQ ID NO 125
<211> LENGTH: 20

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 125
tttaaggcag ggaaaactgc                                              20

<210> SEQ ID NO 126
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 126
attgccagtt gcagttttcc                                              20

<210> SEQ ID NO 127
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 127
aaaagccagc cacctgtttt                                              20

<210> SEQ ID NO 128
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 128
tgaactgtac acatcagttc atcc                                         24

<210> SEQ ID NO 129
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 129
taaacccacc tataaggcac atc                                          23

<210> SEQ ID NO 130
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 130
```
tgtattttcc tttaagaagc cact                                          24

<210> SEQ ID NO 131
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 131
acaggtgaca gaggcactca                                               20

<210> SEQ ID NO 132
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 132
agctccaggg atgtgaagtc                                               20

<210> SEQ ID NO 133
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 133
cagactggag tccccaacat                                               20

<210> SEQ ID NO 134
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 134
tgtttgttaa cctttaatgc tctga                                         25

<210> SEQ ID NO 135
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 135
tatactggcc ctggaatgct                                               20

<210> SEQ ID NO 136
<211> LENGTH: 20
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic primer"

<400> SEQUENCE: 136
gcttgactgc ctttcgaagt                                          20

<210> SEQ ID NO 137
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 137
tggaaaagtg actggactgg                                          20

<210> SEQ ID NO 138
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 138
gggcattctg tgactcggta                                          20

<210> SEQ ID NO 139
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 139
gataggaacc caccgttcat                                          20

<210> SEQ ID NO 140
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 140
ggctagtctg tctatccctt tca                                      23

<210> SEQ ID NO 141
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 141
tccaggagtc cacactcacc                                          20

<210> SEQ ID NO 142
```

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 142
cagctggttg taggtcatgc                                                    20

<210> SEQ ID NO 143
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 143
ggtcttctgc aaggaacgag                                                    20

<210> SEQ ID NO 144
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 144
gcttcctgct tcctcacagt                                                    20

<210> SEQ ID NO 145
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 145
ttgccaacac tgcaaaatgt                                                    20

<210> SEQ ID NO 146
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 146
acaggcttga gaagggttga                                                    20

<210> SEQ ID NO 147
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 147
```
agacctcagc aggctttgtc                                           20

<210> SEQ ID NO 148
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 148
gaggtggttg tgggtgtctt                                           20

<210> SEQ ID NO 149
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 149
cacctttggg tctgcatctc                                           20

<210> SEQ ID NO 150
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 150
cacggacagg tgctcactta                                           20

<210> SEQ ID NO 151
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 151
ggtgagcatg ccagtcttct                                           20

<210> SEQ ID NO 152
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 152
agtgacaaat ccccaagacc                                           20

<210> SEQ ID NO 153
<211> LENGTH: 20
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic primer"

<400> SEQUENCE: 153
gagcttttct cctgggtgtg                                              20

<210> SEQ ID NO 154
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 154
tagacggtag gcatgtgctg                                              20

<210> SEQ ID NO 155
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 155
gtgtggcctg tgtgtgtgtt                                              20

<210> SEQ ID NO 156
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 156
ggattctaac agcgcgattc                                              20

<210> SEQ ID NO 157
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 157
gttcgggtca actcttggaa                                              20

<210> SEQ ID NO 158
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 158
cggcctgctg tgtagtctct                                              20
```

```
<210> SEQ ID NO 159
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 159
tcttgcgtct cactgacctc                                              20

<210> SEQ ID NO 160
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 160
acatgctgtg aagccctctc                                              20

<210> SEQ ID NO 161
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 161
gtcgaggtcc cttgagtgag                                              20

<210> SEQ ID NO 162
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 162
cccctgtgta caaagcactg                                              20

<210> SEQ ID NO 163
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 163
gctgtggtgg ggaatcact                                               19

<210> SEQ ID NO 164
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

```
<400> SEQUENCE: 164
atttcacatc ggcattttcc                                              20

<210> SEQ ID NO 165
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 165
aactccacct ccaggctttc                                              20

<210> SEQ ID NO 166
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 166
gaaagcctgg aggtggagtt                                              20

<210> SEQ ID NO 167
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 167
acatgagcct cggtgttgac                                              20

<210> SEQ ID NO 168
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 168
gctctgctcg ctctccag                                                18

<210> SEQ ID NO 169
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 169
gcagagacac gcacgttg                                                18

<210> SEQ ID NO 170
<211> LENGTH: 20
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic primer"

<400> SEQUENCE: 170
tgaccaggtc ctttctcctg                                              20

<210> SEQ ID NO 171
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 171
ggccttgcga ttcacatact                                              20

<210> SEQ ID NO 172
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 172
atggatgcat gccctaagag                                              20

<210> SEQ ID NO 173
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 173
tctagggctg aggaagcaga                                              20

<210> SEQ ID NO 174
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 174
ctagaggtta agagatgggg acagtamttc aacgctagaa gaacacactc gagct        55

<210> SEQ ID NO 175
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 175
ctagagctcg agtgtgttct tctagcgttg aaktactgtc cccatctctt aacct        55
```

<210> SEQ ID NO 176
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 176
gcaagcugac ccugaaguua au                                    22

<210> SEQ ID NO 177
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 177
gaacuucagg gucagcuugc cg                                    22

<210> SEQ ID NO 178
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 178
tcgaagccac gagaagctgc tgctrcagat caaccccgag cggga           45

<210> SEQ ID NO 179
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 179
ggcctcccgc tcggggttga tctgyagcag cagcttctcg tggct           45

<210> SEQ ID NO 180
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 180
tcgaccggag cctttggaag tctgygccct tgtgccctgc ctcca           45

<210> SEQ ID NO 181
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 181
ggcctggagg cagggcacaa gggcrcagac ttccaaaggc tccgg    45

<210> SEQ ID NO 182
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 182
uucaucagcu uuuccagggu c    21

<210> SEQ ID NO 183
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic
      oligonucleotide"

<400> SEQUENCE: 183
cccuggaaaa gcugaugacg g    21

<210> SEQ ID NO 184
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 184
cgcagagtca gatgtcagga    20

<210> SEQ ID NO 185
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 185
gggtctcttg cttgttcgag    20

<210> SEQ ID NO 186
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 186
ggacttcgag caagagatgg    20

<210> SEQ ID NO 187
<211> LENGTH: 20

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 187
agcactgtgt tggcgtacag                                                   20

<210> SEQ ID NO 188
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 188
uacagacuuc caaaggcucc g                                                 21

<210> SEQ ID NO 189
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 189
ucacagacuu ccaaaggcuc c                                                 21

<210> SEQ ID NO 190
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 190
ugcacagacu uccaaaggcu c                                                 21

<210> SEQ ID NO 191
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 191
uggcacagac uuccaaaggc u                                                 21

<210> SEQ ID NO 192
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 192
```
ugggcacaga cuuccaaagg c          21

<210> SEQ ID NO 193
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 193
uagggcacag acuuccaaag g          21

<210> SEQ ID NO 194
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 194
uaagggcaca gacuuccaaa g          21

<210> SEQ ID NO 195
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 195
ucaagggcac agacuuccaa a          21

<210> SEQ ID NO 196
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 196
uggcacaagg gcacagacuu c          21

<210> SEQ ID NO 197
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 197
guagggcaca agggcacaga c          21

<210> SEQ ID NO 198
<211> LENGTH: 21
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 198
gccgggcaca agggcacaga c                                              21

<210> SEQ ID NO 199
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 199
gcauggcaca agggcacaga c                                              21

<210> SEQ ID NO 200
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 200
gcagugcaca agggcacaga c                                              21

<210> SEQ ID NO 201
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 201
gcaggucaca agggcacaga c                                              21

<210> SEQ ID NO 202
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 202
gcaggguaca agggcacaga c                                              21

<210> SEQ ID NO 203
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 203
gcagggcaca aggaacaga c                                               21

<210> SEQ ID NO 204
```

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 204
gcagggcaca aggguacaga c                                             21

<210> SEQ ID NO 205
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 205
gcagggcaca agggcauaga c                                             21

<210> SEQ ID NO 206
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 206
gcagggcaca agggcaaaga c                                             21

<210> SEQ ID NO 207
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 207
cagggcacaa gggcauagac u                                             21

<210> SEQ ID NO 208
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 208
agcguugaag uacugucccc a                                             21

<210> SEQ ID NO 209
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 209
```
agcguugaau uacugucccc a                                              21

<210> SEQ ID NO 210
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 210
ucuucuagcg uugaaguacu g                                              21

<210> SEQ ID NO 211
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 211
ucuucuagcg uugaauuacu g                                              21

<210> SEQ ID NO 212
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 212
cacaagggcg cagacuucca a                                              21

<210> SEQ ID NO 213
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 213
uacaagggca cagacuucca a                                              21

<210> SEQ ID NO 214
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 214
gcagggcaca agggcgcaga c                                              21

<210> SEQ ID NO 215
<211> LENGTH: 21
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 215
ucagggcaca agggcacaga c                                            21

<210> SEQ ID NO 216
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 216
cgcaagggca cagacuucca a                                            21

<210> SEQ ID NO 217
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 217
cauaagggca cagacuucca a                                            21

<210> SEQ ID NO 218
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 218
caccagggca cagacuucca a                                            21

<210> SEQ ID NO 219
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 219
cacacgggca cagacuucca a                                            21

<210> SEQ ID NO 220
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 220
cacaauggca cagacuucca a                                            21
```

```
<210> SEQ ID NO 221
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 221
cacaagugca cagacuucca a                                            21

<210> SEQ ID NO 222
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 222
cacaauggcg cagacuucca a                                            21

<210> SEQ ID NO 223
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 223
guugaucugu agcagcagcu u                                            21

<210> SEQ ID NO 224
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 224
guugaucugc agcagcagcu u                                            21

<210> SEQ ID NO 225
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 225
cucgggguug aucuguagca g                                            21

<210> SEQ ID NO 226
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 226 cucggggsuug aucugcagca g                                              21

<210> SEQ ID NO 227
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 227
ucugaucugu agcagcagcu u                                               21

<210> SEQ ID NO 228
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 228
uucgaucugu agcagcagcu u                                               21

<210> SEQ ID NO 229
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 229
uuuuaucugu agcagcagcu u                                               21

<210> SEQ ID NO 230
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 230
uuugcucugu agcagcagcu u                                               21

<210> SEQ ID NO 231
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 231
uuugaccugu agcagcagcu u                                               21

<210> SEQ ID NO 232
<211> LENGTH: 21
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 232
uuugauuugu agcagcagcu u                                              21

<210> SEQ ID NO 233
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 233
uuugcucugc agcagcagcu u                                              21
```